(12) United States Patent
Kawakami et al.

(10) Patent No.: US 8,686,628 B2
(45) Date of Patent: *Apr. 1, 2014

(54) ANTHRACENE DERIVATIVE

(75) Inventors: Sachiko Kawakami, Isehara (JP); Harue Nakashima, Atsugi (JP); Kumi Kojima, Machida (JP); Nobuharu Ohsawa, Zama (JP); Ryoji Nomura, Yamato (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/512,244

(22) Filed: Aug. 30, 2006

(65) Prior Publication Data

US 2007/0075632 A1 Apr. 5, 2007

(30) Foreign Application Priority Data

Sep. 2, 2005 (JP) ................................. 2005-254363

(51) Int. Cl.
*H05B 33/14* (2006.01)
*C07D 209/88* (2006.01)
*C07D 209/82* (2006.01)

(52) U.S. Cl.
USPC .......................................... 313/504; 548/444

(58) Field of Classification Search
None
See application file for complete search history.

(56) References Cited

U.S. PATENT DOCUMENTS

| | | | |
|---|---|---|---|
| 5,811,834 A | 9/1998 | Tamano et al. | |
| 6,730,419 B2 | 5/2004 | Kim et al. | |
| 6,767,654 B2 | 7/2004 | Tamao et al. | |
| 6,815,094 B2 | 11/2004 | Lee et al. | |
| 7,541,099 B2 | 6/2009 | Yamagata et al. | |
| 7,649,211 B2* | 1/2010 | Ohsawa | 257/103 |
| 7,985,974 B2* | 7/2011 | Nowatari et al. | 257/87 |
| 8,076,676 B2* | 12/2011 | Ohsawa | 257/79 |
| 8,151,150 B2* | 4/2012 | Lu | 714/719 |
| 2003/0064246 A1 | 4/2003 | Kim et al. | |
| 2003/0143430 A1 | 7/2003 | Kawamura et al. | |
| 2003/0152800 A1 | 8/2003 | Tamao et al. | |
| 2003/0215667 A1 | 11/2003 | Xie | |
| 2003/0215668 A1 | 11/2003 | Kondakov et al. | |
| 2004/0146746 A1 | 7/2004 | Lee et al. | |
| 2004/0161632 A1 | 8/2004 | Seo et al. | |
| 2004/0161633 A1 | 8/2004 | Seo et al. | |
| 2005/0064233 A1 | 3/2005 | Matsuura et al. | |
| 2005/0221124 A1 | 10/2005 | Hwang et al. | |
| 2006/0033421 A1 | 2/2006 | Matsuura et al. | |
| 2007/0267969 A1* | 11/2007 | Nakashima et al. | 313/504 |
| 2008/0006822 A1* | 1/2008 | Ohsawa | 257/40 |
| 2008/0231177 A1* | 9/2008 | Nomura et al. | 313/504 |
| 2008/0261075 A1* | 10/2008 | Seo et al. | 428/690 |
| 2009/0072725 A1* | 3/2009 | Suzuki et al. | 313/504 |
| 2009/0236590 A1* | 9/2009 | Ohsawa | 257/40 |
| 2009/0236980 A1* | 9/2009 | Ohsawa | 313/504 |
| 2010/0133573 A1* | 6/2010 | Nowatari et al. | 257/98 |

FOREIGN PATENT DOCUMENTS

| | | |
|---|---|---|
| CN | 1407053 | 4/2003 |
| EP | 0 786 926 | 7/1997 |
| JP | 09-268283 | 10/1997 |
| JP | 2003-146951 | 5/2003 |
| JP | 2004-087393 | 3/2004 |
| JP | 2004-087395 | 3/2004 |
| JP | 2004-103467 | 4/2004 |
| JP | 2004-210786 | 7/2004 |
| JP | 2005-047868 | 2/2005 |
| JP | 2005-206551 | 8/2005 |
| WO | WO 00/40586 | 7/2000 |
| WO | WO 2004/053018 | 6/2004 |

(Continued)

OTHER PUBLICATIONS

Hacks Chemical Dictionary, Fourth Edition, Julius Grant, 1972, p. 203.*

(Continued)

*Primary Examiner* — Sun Jae Yoo
(74) *Attorney, Agent, or Firm* — Eric J. Robinson; Robinson Intellectual Property Law Office, P.C.

(57) ABSTRACT

It is an object of the present invention to provide a novel material which has excellent light-emitting efficiency, a light-emitting element provided with the novel material, and a light-emitting device using the light-emitting element. The present invention provides an anthracene derivative represented by the following general formula (1)

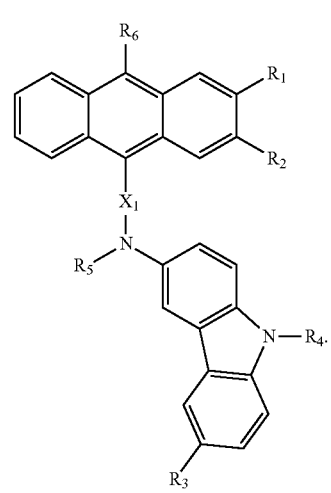

(1)

18 Claims, 34 Drawing Sheets

(56) References Cited

FOREIGN PATENT DOCUMENTS

| | | |
|---|---|---|
| WO | WO 2004/075603 | 9/2004 |
| WO | WO 2004/075604 | 9/2004 |
| WO | WO 2005/113531 | 12/2005 |
| WO | WO 2006/070907 | 7/2006 |
| WO | WO 2006/104221 | 10/2006 |

OTHER PUBLICATIONS

U.S. Appl. No. 12/404,924; 2009, Ohsawa.*
U.S. Appl. No. 12/404,991; 2009; Ohsawa.*
U.S. Appl. No. 12/206,252;2008; Suzuki et al.*
U.S. Appl. No. 12/048,516; 2008, Nomura et al.*
U.S. Appl. No. 11/946,484; 2007; Ohsawa.*
U.S. Appl. No. 11/807,267; 2007; Ohsawa.*
U.S. Appl. No. 12/627,147; 2009; Nowatari.*
International Search Report (Application No. PCT/JP2006/316819) dated Nov. 28, 2006.
Written Opinion (Application No. PCT/JP2006/316819) dated Nov. 28, 2006.
Search Report (Application No. 06796853.7) Dated Mar. 2, 2010.

* cited by examiner

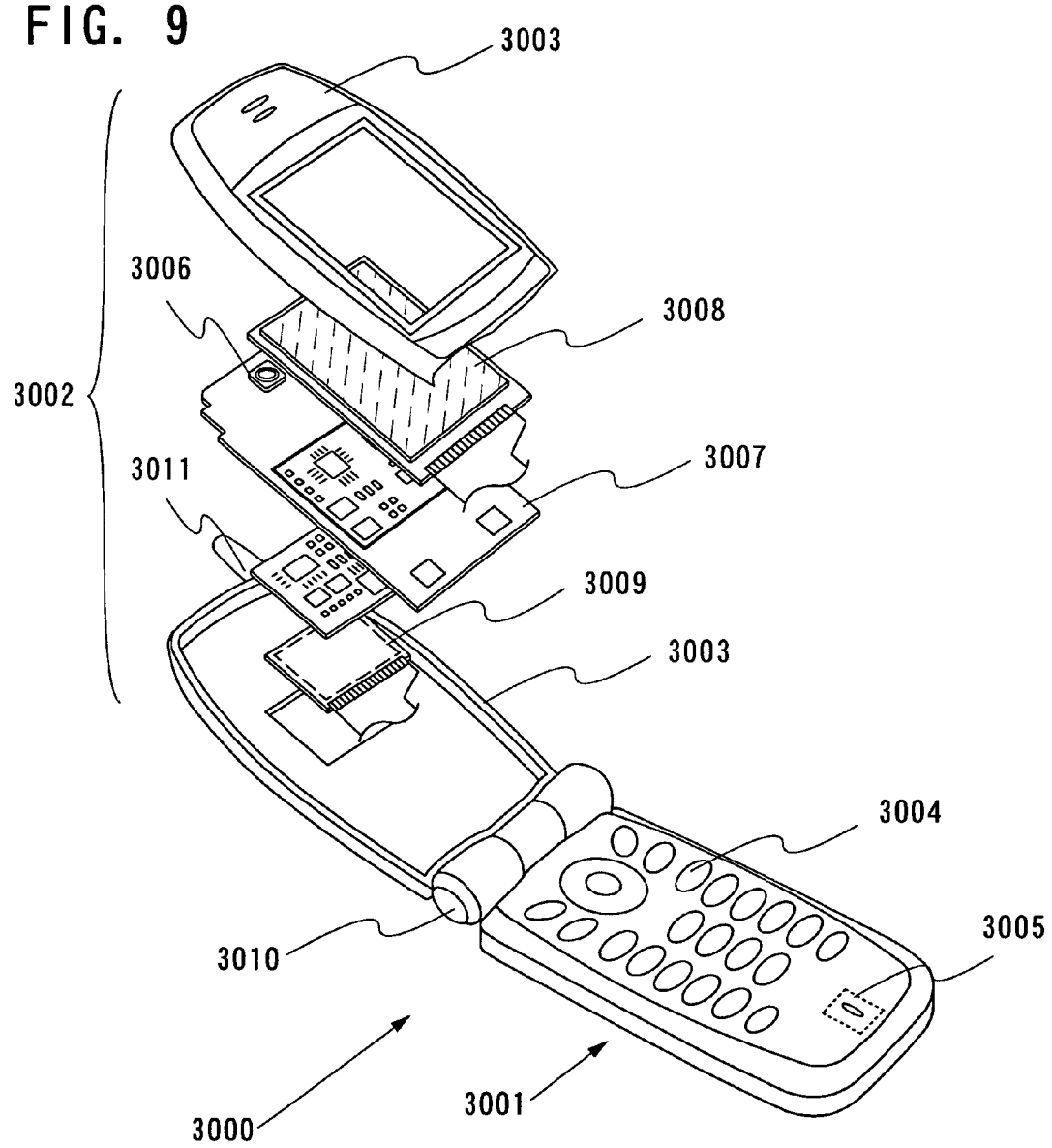

ANTHRACENE DERIVATIVE

TECHNICAL FIELD

The present invention relates to an anthracene derivative. In addition, the present invention relates to a light-emitting element containing an anthracene derivative. Further, the present invention relates to a light-emitting device having a light-emitting element containing an anthracene derivative.

BACKGROUND ART

A light-emitting element using a light-emitting material has advantages of thinness, lightness in weight, and so on, and is expected to be applied to a next-generation display. Further, since the light-emitting element is a self-light-emitting type, the light-emitting element is superior to a liquid crystal display (LCD) in high visibility without a problem such as a viewing angle.

A basic structure of a light-emitting element is a structure having a light-emitting layer between a pair of electrodes. Voltage is applied to such a light-emitting element, so that holes injected from an anode and electrons injected from a cathode are recombined in a light-emission center of the light-emitting layer to excite molecules; thus, light is emitted by emitting energy when the excited molecules returns to the ground state. Note that the excited state generated by the recombination includes a singlet-excited state and a triplet-excited state. The light emission can be obtained in either of the excited states. In particular, the light emission when the singlet-excited state returns to the ground state is referred to as fluorescence, and the light emission when the triplet-excited state returns to the ground state is referred to as phosphorescence.

By the way, in the case where a light-emitting element is incorporated as a display portion of a device using electromotive force from a battery, for example, an electronic device such as a mobile phone, a camera, or a portable music reproducing device, low power consumption is required in order to continually use the device including the display portion with the light-emitting element for a long time. Development of an efficient light-emitting element is required in order to achieve low power consumption; therefore, a light-emitting material having excellent light-emitting efficiency has been sought for, and many studies thereof have been done (Reference 1: International Publication No. 2000/040586 pamphlet).

DISCLOSURE OF INVENTION

The present invention has been made in view of the above-described situation. It is an object of the present invention to provide a novel material which has excellent light-emitting efficiency and high reliability, a light-emitting element containing the novel material, and a light-emitting device using the light-emitting element.

An aspect of the present invention is an anthracene derivative represented by the following general formula (1).

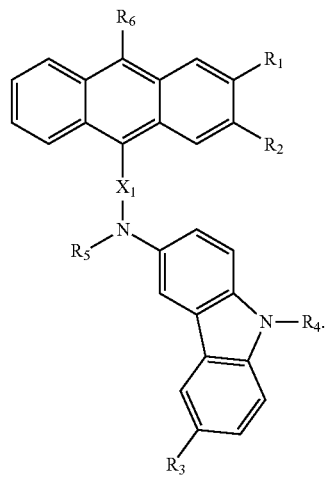

(1)

In the general formula (1), $R_1$ and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms. The aryl group may have a substituent or no substituent. $R_4$ represents either an alkyl group having 1 to 4 carbon atoms or an aryl group having 6 to 25 carbon atoms. The aryl group may have a substituent or no substituent. $R_5$ represents an aryl group having 6 to 25 carbon atoms. $R_6$ represents an aryl group having 6 to 25 carbon atoms. The aryl group may have a substituent or no substituent. Xi represents an arylene group having 6 to 25 carbon atoms. The arylene group may have a substituent or no substituent.

Another aspect of the present invention is an anthracene derivative represented by the following general formula (2).

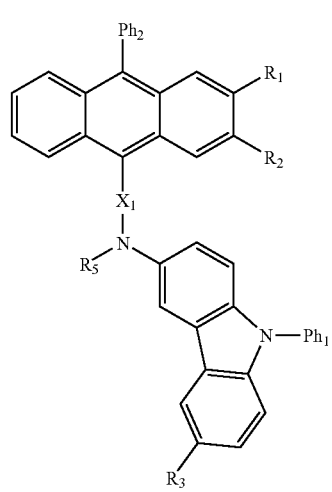

(2)

In the general formula (2), $R_1$ and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms. $R_5$ represents an aryl group having 6 to 25 carbon atoms. The aryl group may have a substituent or no substituent. $Ph_1$ and $Ph_2$ each represent a phenyl group. The phenyl group may have a substituent or no substituent. Xi represents an arylene group having 6 to 25 carbon atoms. The arylene group may have a substituent or no substituent.

Another aspect of the present invention is an anthracene derivative represented by the following general formula (3).

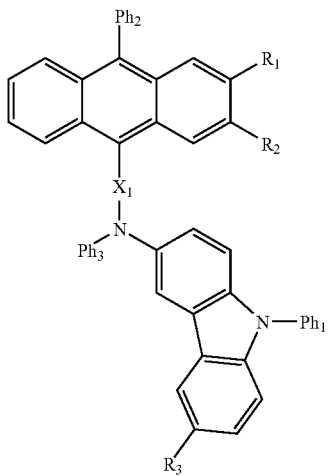

(3)

In the general formula (3), R, and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms. The aryl group may have a substituent or no substituent. $Ph_1$, $Ph_2$, and $Ph_3$ each represent a phenyl group. The phenyl group may have a substituent or no substituent. $X_1$ represents an arylene group having 6 to 25 carbon atoms. The arylene group may have a substituent or no substituent.

Another aspect of the present invention is an anthracene derivative represented by the following general formula (4).

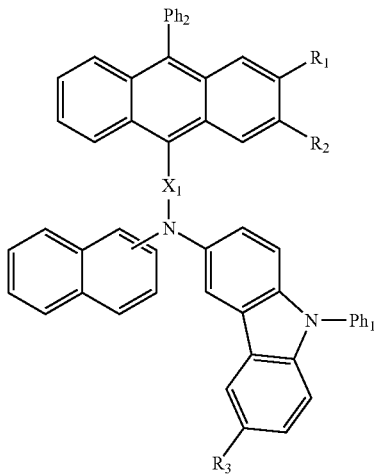

(4)

In the general formula (4), $R_1$ and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms. The aryl group may have a substituent or no substituent. $Ph_1$ and $Ph_2$ each represent a phenyl group. The phenyl group may have a substituent or no substituent. $X_1$ represents an arylene group having 6 to 25 carbon atoms. The arylene group may have a substituent or no substituent.

Another aspect of the present invention is an anthracene derivative represented by the following general formula (5).

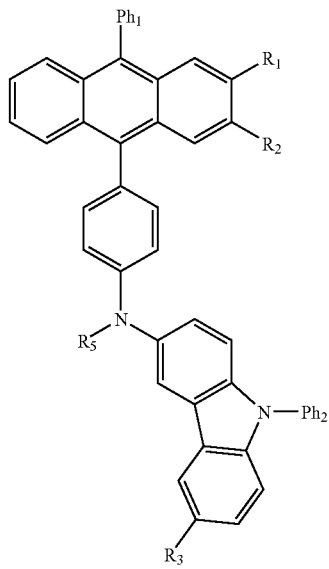

(5)

In the general formula (5), $R_1$ and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms. The aryl group may have a substituent or no substituent. $Ph_1$ and $Ph_2$ each represent a phenyl group. The phenyl group may have a substituent or no substituent.

Another aspect of the present invention is an anthracene derivative represented by the following general formula (6).

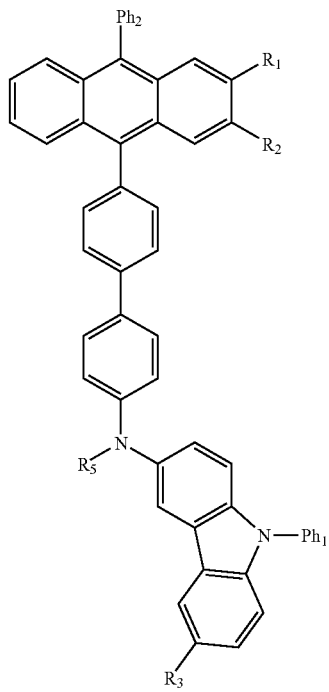

(6)

In the general formula (6), $R_1$ and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms.

The aryl group may have a substituent or no substituent. $Ph_1$ and $Ph_2$ each represent a phenyl group. The phenyl group may have a substituent or no substituent.

Another aspect of the present invention is an anthracene derivative represented by the following general formula (7).

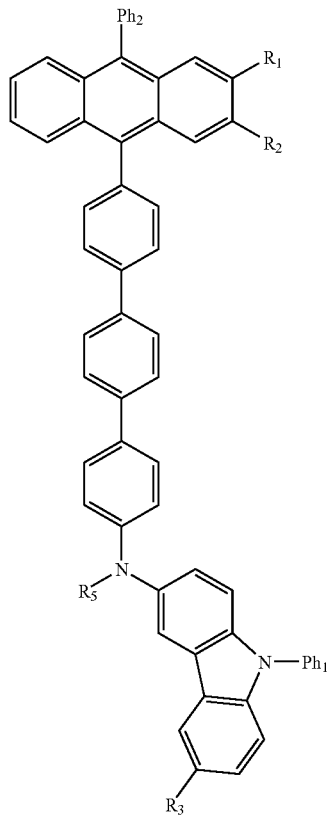

(7)

In the general formula (7), $R_1$ and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms. The aryl group may have a substituent or no substituent. $Ph_1$, $Ph_2$, and $Ph_3$ each represent a phenyl group. The phenyl group may have a substituent or no substituent.

Another aspect of the present invention is an anthracene derivative represented by the following general formula (8).

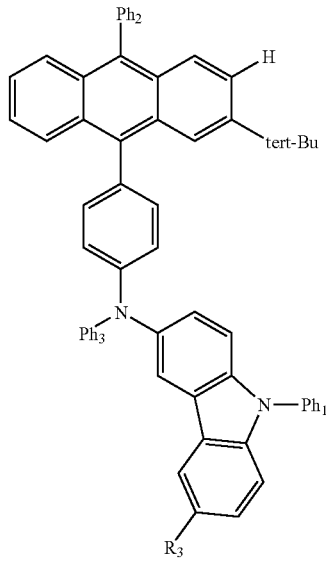

(8)

In the general formula (8), $R_3$ represents any one of hydrogen, an alkyl group having 1 to 4 carbon atoms or an aryl group having 6 to 25 carbon atoms. The aryl group may have a substituent or no substituent. $Ph_1$, $Ph_2$, and $Ph_3$ each represent a phenyl group. The phenyl group may have a substituent or no substituent.

Another aspect of the present invention is an anthracene derivative represented by the following general formula (9).

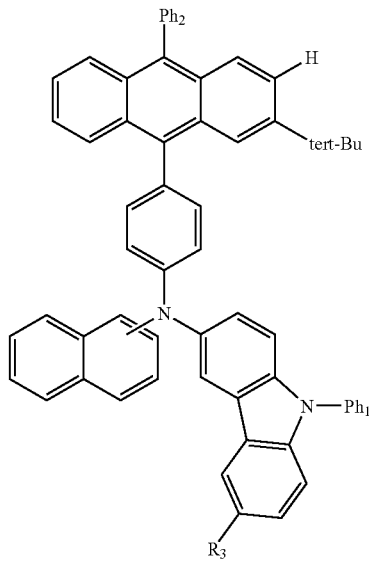

(9)

In the general formula (9), $R_3$ represents any one of hydrogen, an alkyl group having 1 to 4 carbon atoms or an aryl group having 6 to 25 carbon atoms. The aryl group may have a substituent or no substituent. $Ph_1$ and $Ph_2$ each represent a phenyl group. The phenyl group may have a substituent or no substituent.

Another aspect of the present invention is an anthracene derivative represented by the following general formula (10).

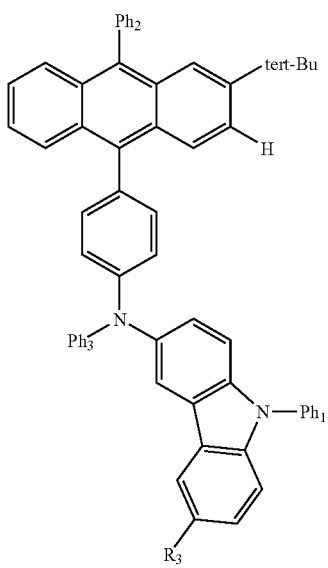

(10)

In the general formula (10), R₃ represents any one of hydrogen, an alkyl group having 1 to 4 carbon atoms or an aryl group having 6 to 25 carbon atoms. The aryl group may have a substituent or no substituent. Ph₁, Ph₂, and Ph₃ each represent a phenyl group. The phenyl group may have a substituent or no substituent.

Another aspect of the present invention is an anthracene derivative represented by the following general formula (11).

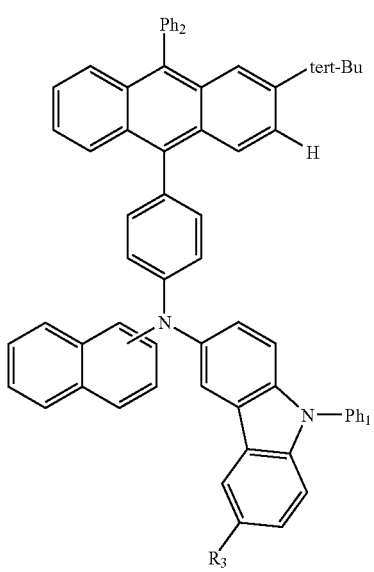

(11)

In the general formula (11), R₃ represents any one of hydrogen, an alkyl group having 1 to 4 carbon atoms or an aryl group having 6 to 25 carbon atoms. The aryl group may have a substituent or no substituent. Ph₁ and Ph₂ each represent a phenyl group. The phenyl group may have a substituent or no substituent.

Another aspect of the present invention is an anthracene derivative represented by the following general formula (12).

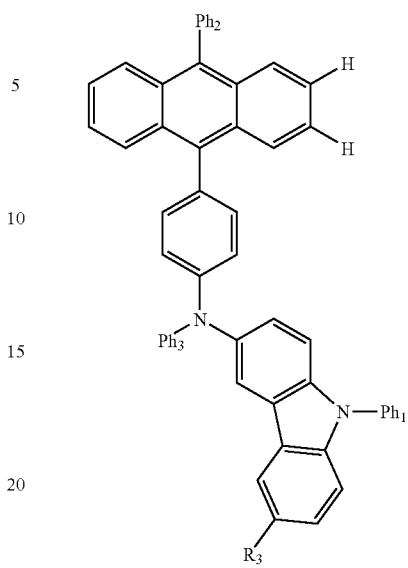

(12)

In the general formula (12), R₃ represents any one of hydrogen, an alkyl group having 1 to 4 carbon atoms or an aryl group having 6 to 25 carbon atoms. The aryl group may have a substituent or no substituent. Ph₁, Ph₂, and Ph₃ each represent a phenyl group. The phenyl group may have a substituent or no substituent.

Another aspect of the present invention is an anthracene derivative represented by the following general formula (13).

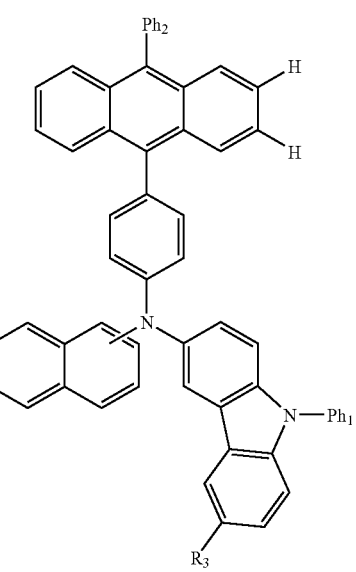

(13)

In the general formula (13), R₃ represents any one of hydrogen, an alkyl group having 1 to 4 carbon atoms or an aryl group having 6 to 25 carbon atoms. The aryl group may have a substituent or no substituent. Ph₁ and Ph₂ each represent a phenyl group. The phenyl group may have a substituent or no substituent.

Another aspect of the present invention is an anthracene derivative represented by the following general formula (14).

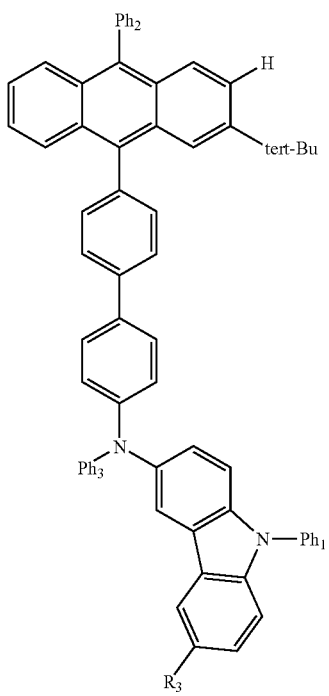

(14)

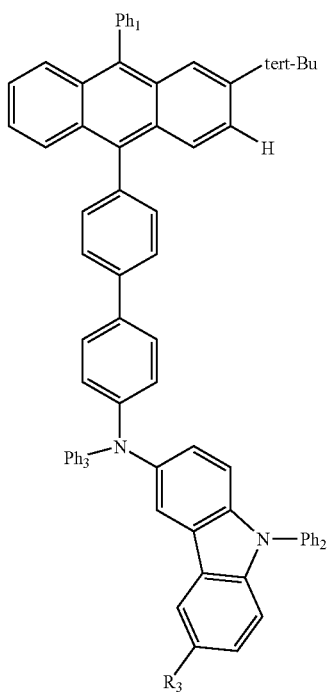

(15)

In the general formula (14), R₃ represents any one of hydrogen, an alkyl group having 1 to 4 carbon atoms or an aryl group having 6 to 25 carbon atoms. The aryl group may have a substituent or no substituent. Ph₁, Ph₂, and Ph₃ each represent a phenyl group. The phenyl group may have a substituent or no substituent.

Another aspect of the present invention is an anthracene derivative represented by the following general formula (15).

In the general formula (15), R₃ represents any one of hydrogen, an alkyl group having 1 to 4 carbon atoms or an aryl group having 6 to 25 carbon atoms. The aryl group may have a substituent or no substituent. Ph₁, Ph₂, and Ph₃ each represent a phenyl group. The phenyl group may have a substituent or no substituent.

Another aspect of the present invention is an anthracene derivative represented by the following general formula (16).

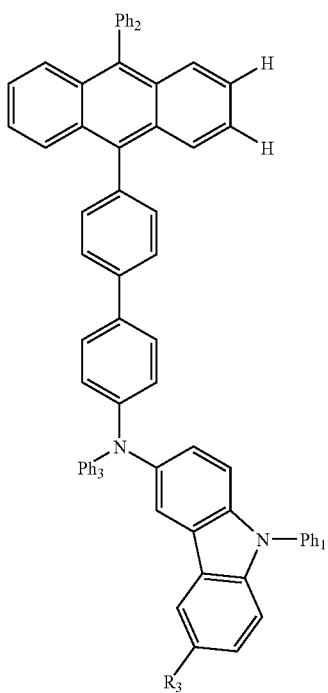

(16)

In the general formula (16), $R_3$ represents any one of hydrogen, an alkyl group having 1 to 4 carbon atoms or an aryl group having 6 to 25 carbon atoms. The aryl group may have a substituent or no substituent. $Ph_1$, $Ph_2$, and $Ph_3$ each represent a phenyl group. The phenyl group may have a substituent or no substituent.

Another aspect of the present invention is a light-emitting element that has a layer containing an anthracene derivative described in any one of the general formulas (1) to (16) between a pair of electrodes.

Another aspect of the present invention is a light-emitting element having a layer containing an anthracene derivative described in any one of the general formulas (1) to (16) and a host which is a substance having a higher energy gap than the anthracene derivative, and having a higher ionization potential than the anthracene derivative between a pair of electrodes.

Another aspect of the present invention is a light-emitting element having a layer containing an anthracene derivative described in any one of the general formulas (1) to (16) and a light-emitting substance having a smaller energy gap than the anthracene derivative, and having a smaller ionization potential than the anthracene derivative between a pair of electrodes.

Another aspect of the present invention is a light-emitting device using a light-emitting element containing an anthracene derivative described in any one of the general formulas (1) to (16).

Another aspect of the present invention is an electronic device including a light-emitting element containing an anthracene derivative described in any one of the general formulas (1) to (16).

An anthracene derivative of the present invention is an anthracene derivative from which light emission can be obtained with excellent light-emitting efficiency.

The anthracene derivative of the present invention is a light-emitting substance from which light emission can be obtained with excellent light-emitting efficiency.

In addition, the anthracene derivative of the present invention can be used as a host material of the light-emitting layer.

By containing the anthracene derivative of the present invention, a light-emitting element having high external quantum efficiency can be obtained. Accordingly, a light-emitting element having excellent light-emitting efficiency can be obtained.

By containing the anthracene derivative of the present invention, the driving voltage of the light-emitting element can be decreased and a light-emitting element having excellent current efficiency and high power efficiency can be obtained.

By having a light-emitting element containing the anthracene derivative of the present invention, a light-emitting device having low power consumption and light emission with high luminance can be obtained.

BRIEF DESCRIPTION OF DRAWINGS

FIG. 9 shows an example of an electronic device of the present invention.

BEST MODE FOR CARRYING OUT THE INVENTION

Figure 1:
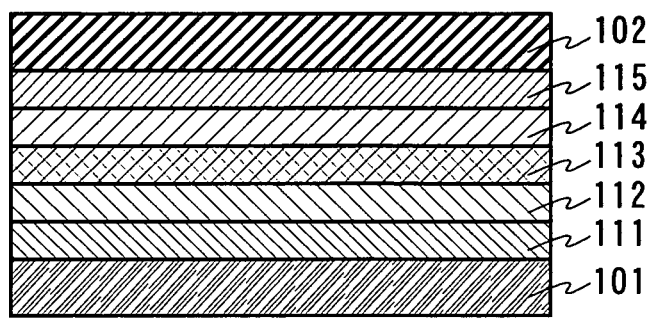
FIG. 1 shows an example of a light-emitting element of the present invention.

The present invention will be fully described by way of embodiment modes with reference to the accompanying drawings below. However, it is to be understood that various changes and modifications will be apparent to those skilled in the art. Therefore, unless such changes and modification depart from the scope of the present invention, they should be construed as being included therein. Note that the same reference numeral is used among different drawings to denote the same component in the structure of the present invention described below.

Embodiment Mode 1

In this embodiment mode, an anthracene derivative of the present invention is described.

Anthracene derivatives represented by structural formulas 17 to 72 are used as the anthracene derivative of the present invention. Note that the anthracene derivative of the present invention is not limited to the following structural formulas, and may have a structure different from the structures represented by the following structural formulas.

(17)

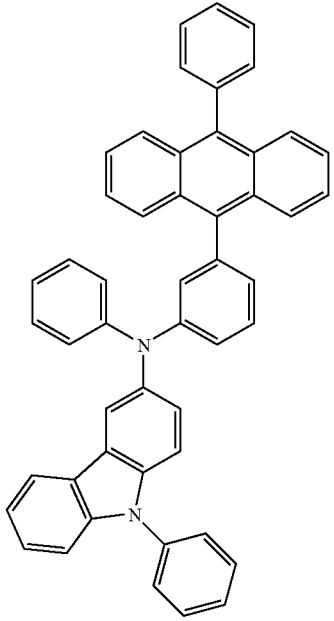

-continued (18)

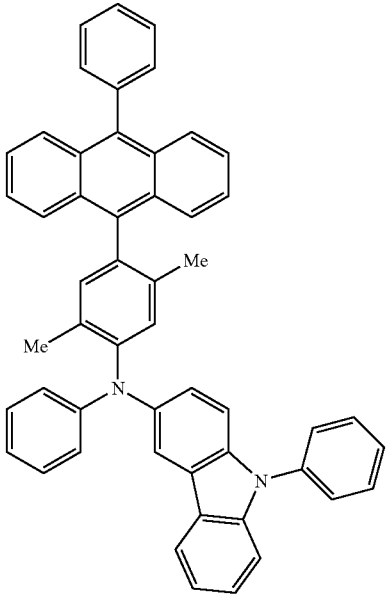

(19)

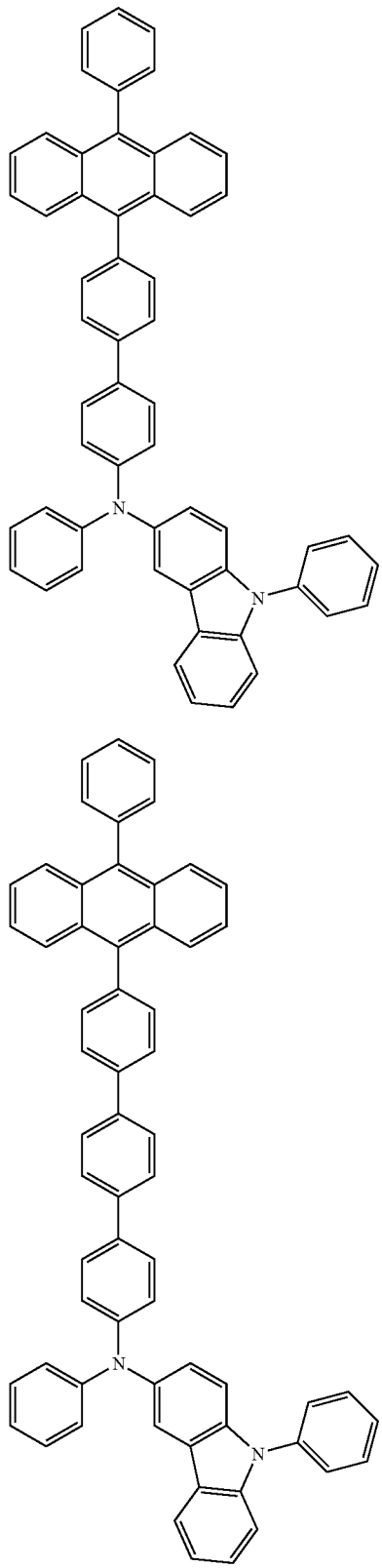
(20)
(21)
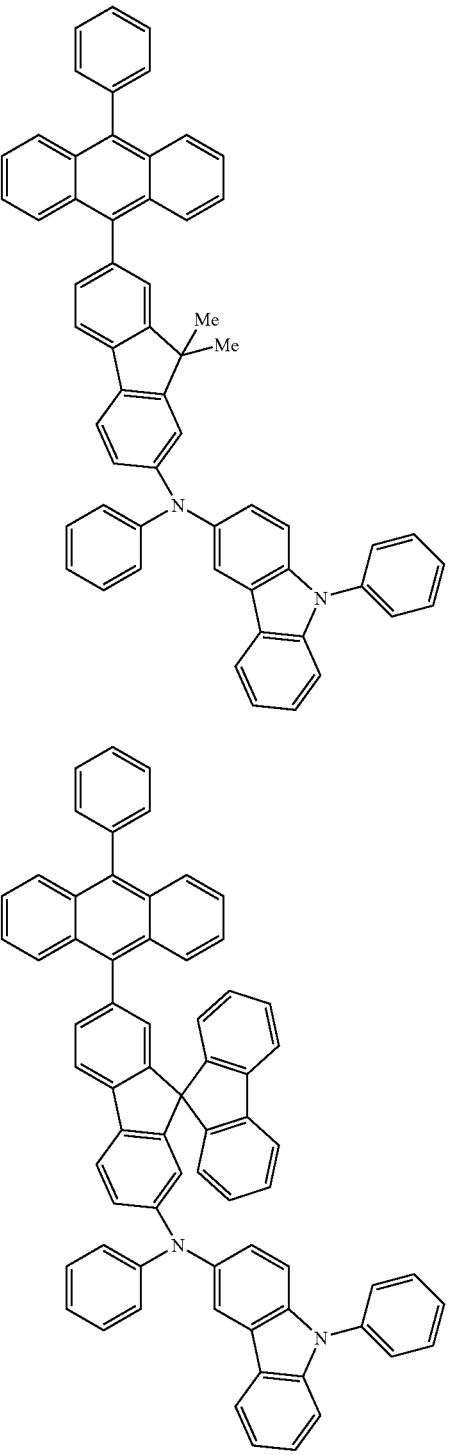
(22)
(23)

-continued
(24)
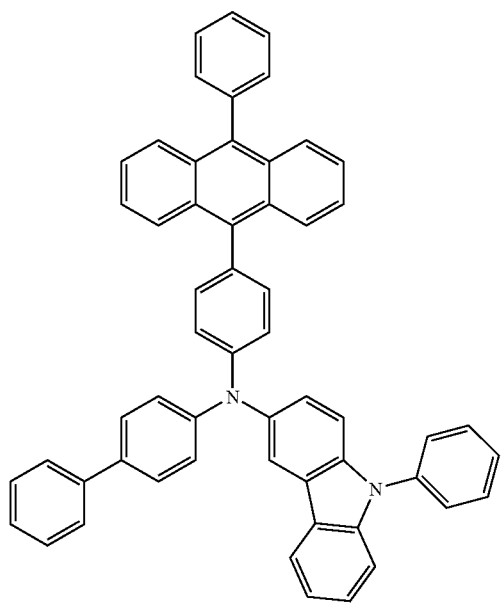
(25)
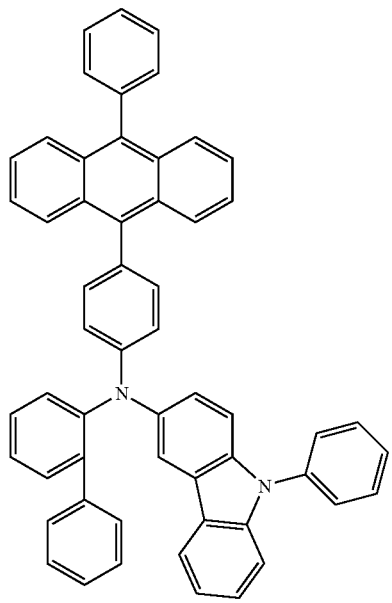
(26)
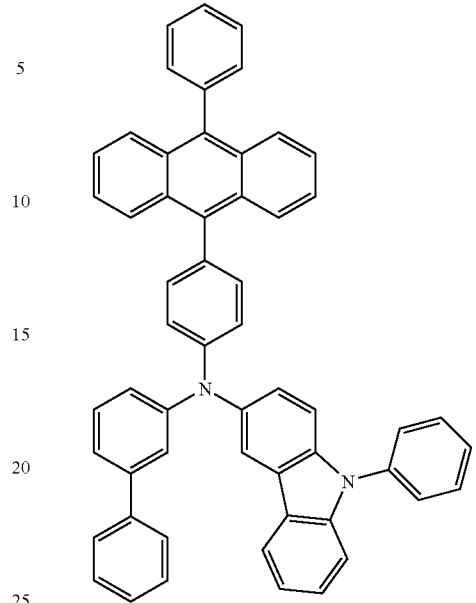
(27)
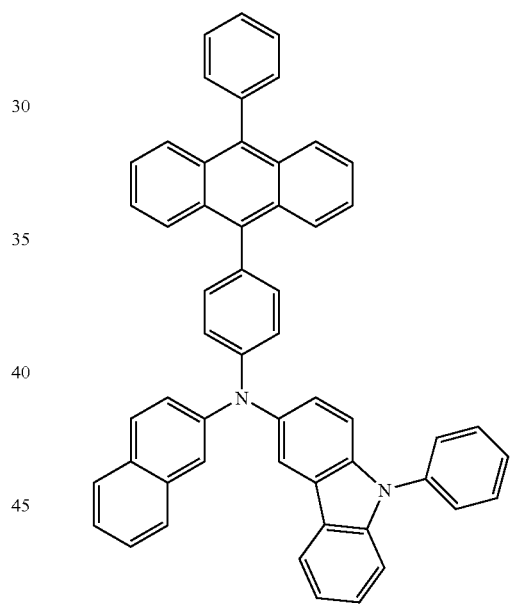

(28)
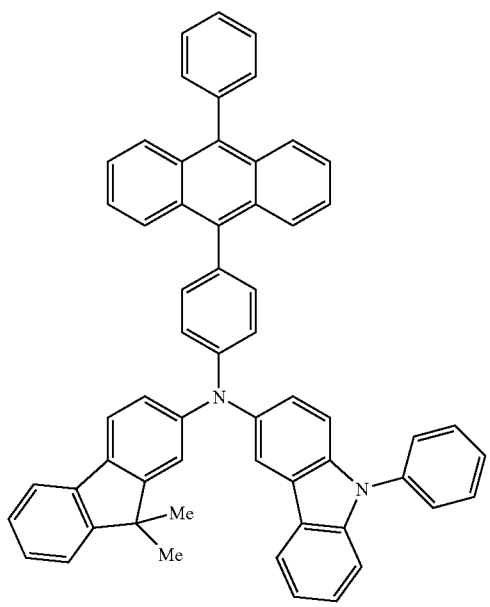
(29)
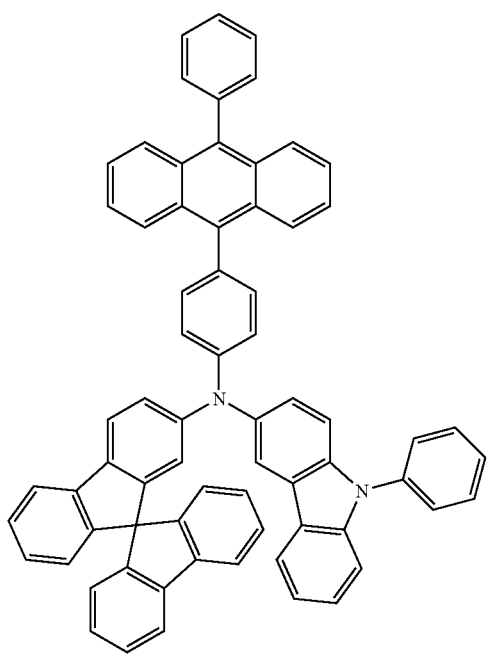
(30)
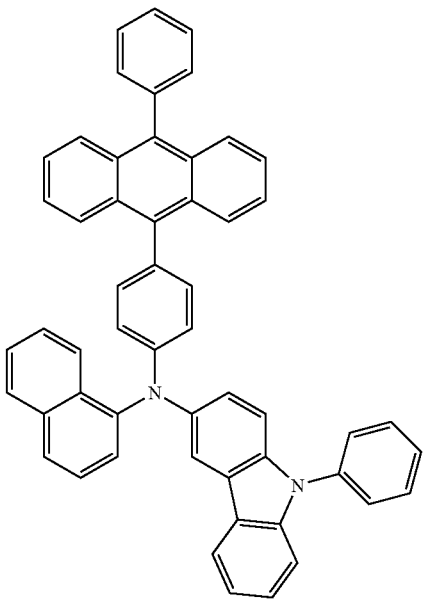
(31)
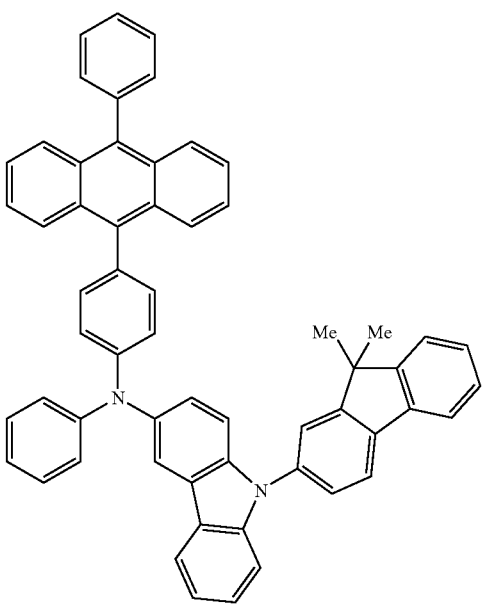

(32)
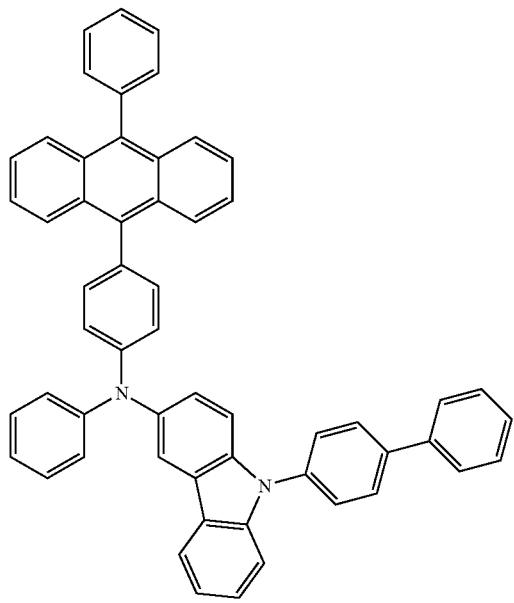
(33)
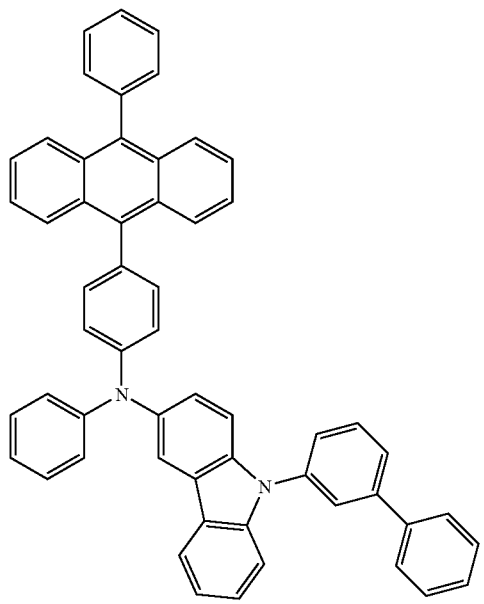
(34)
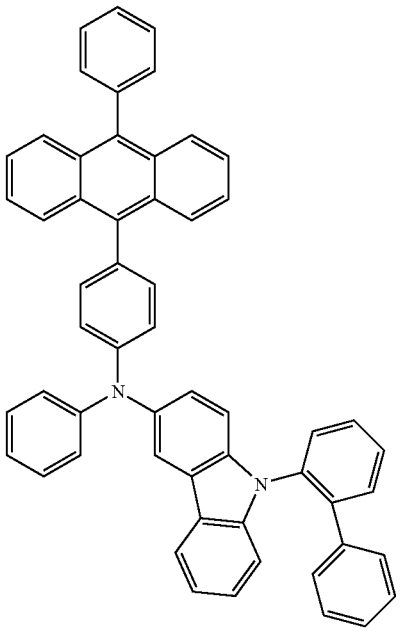
(35)
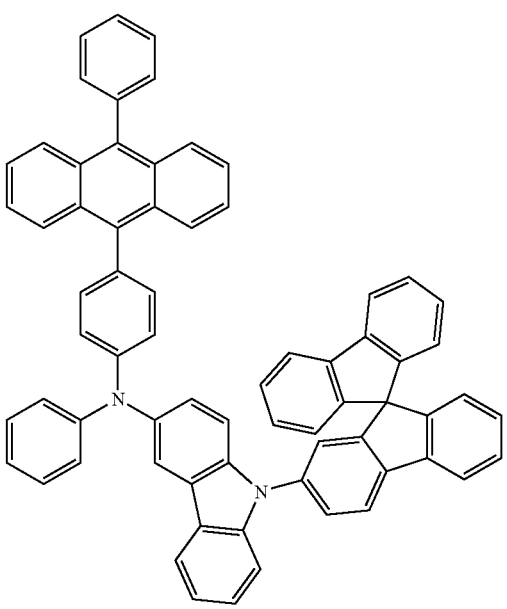

(36)
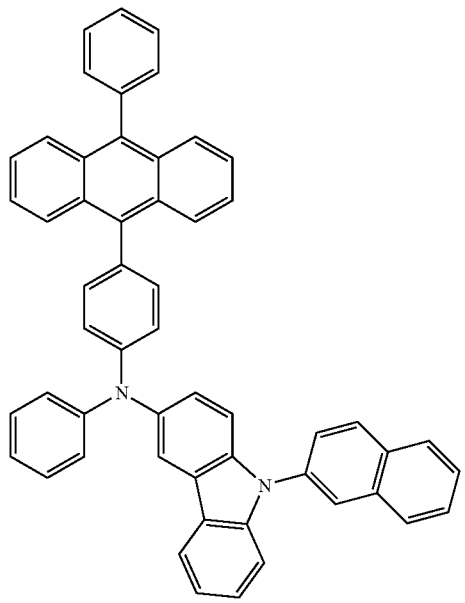
(37)
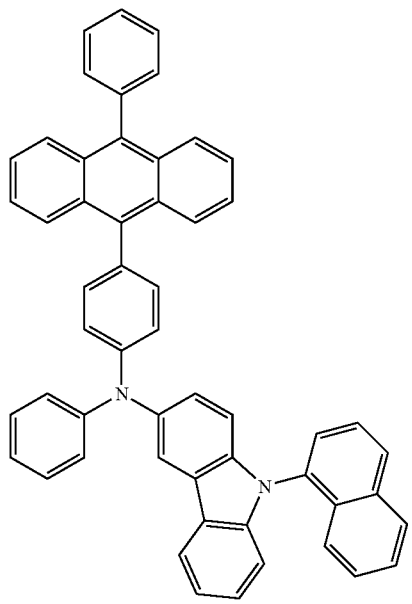
(38)
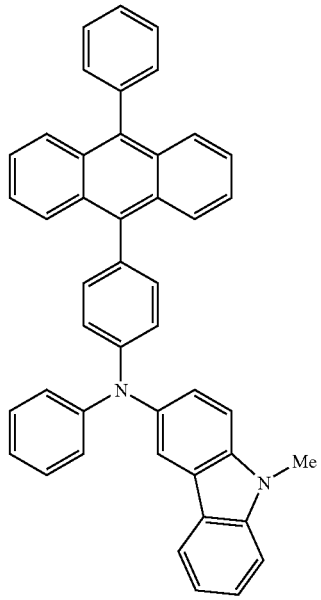
(39)
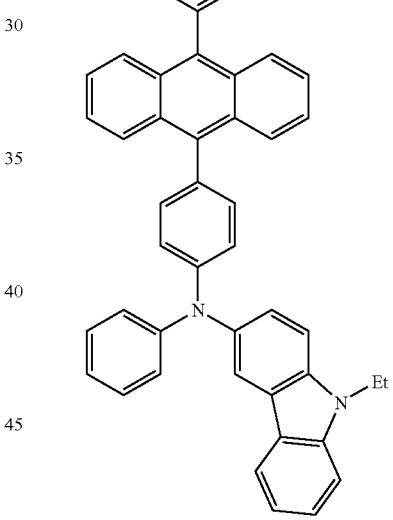

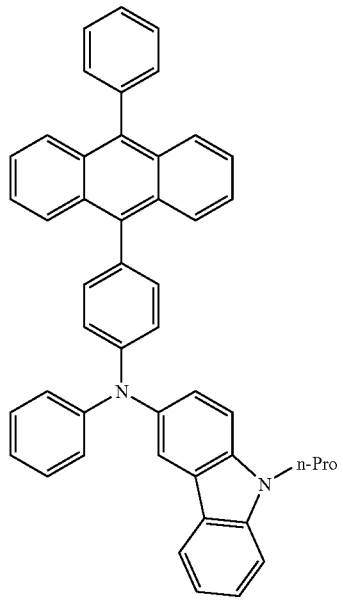
(40)
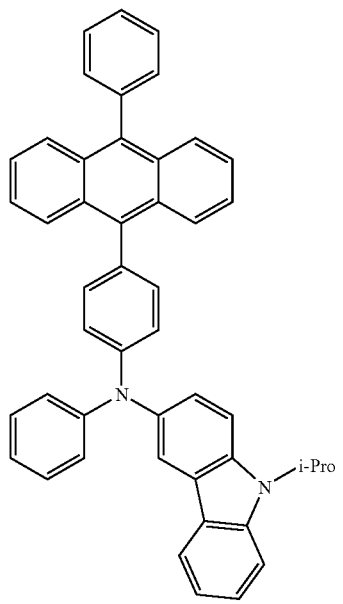
(41)
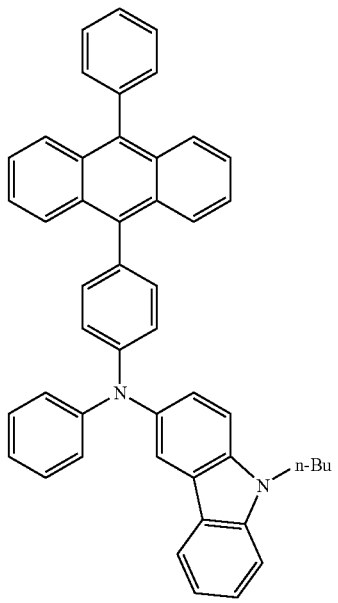
(42)
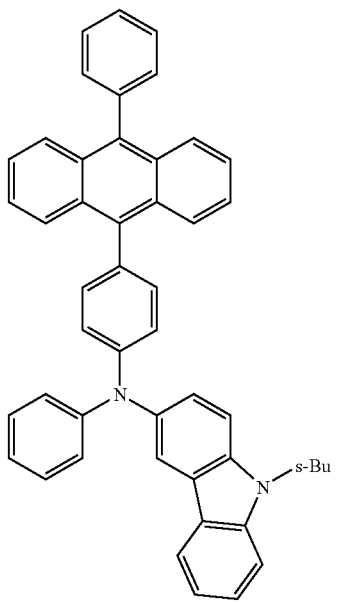
(43)

(44)
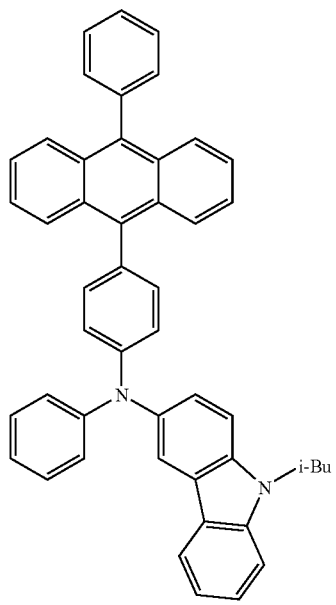
(45)
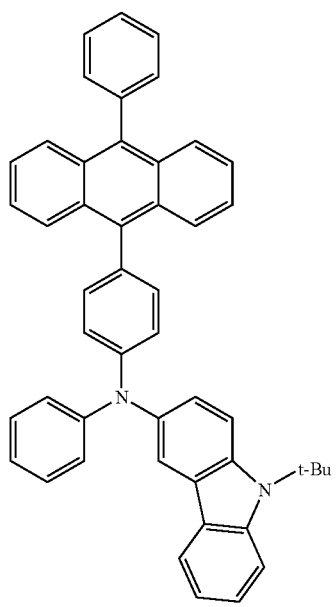
(46)
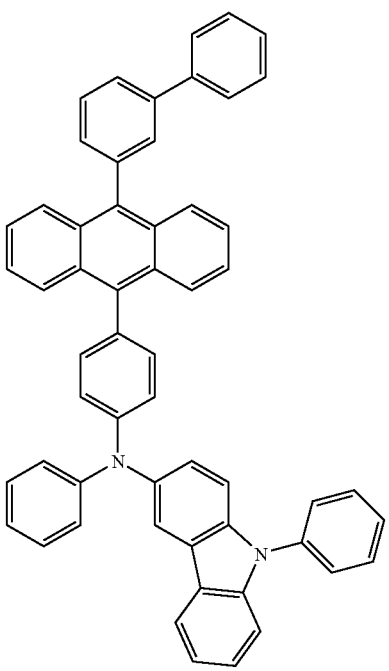
(47)
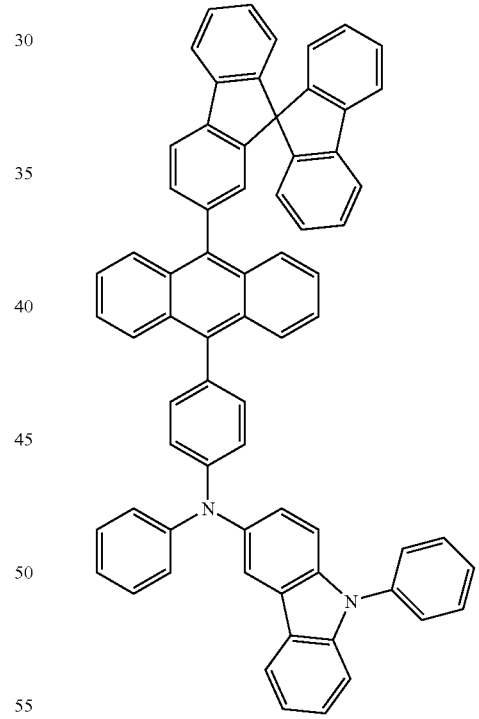

(48)
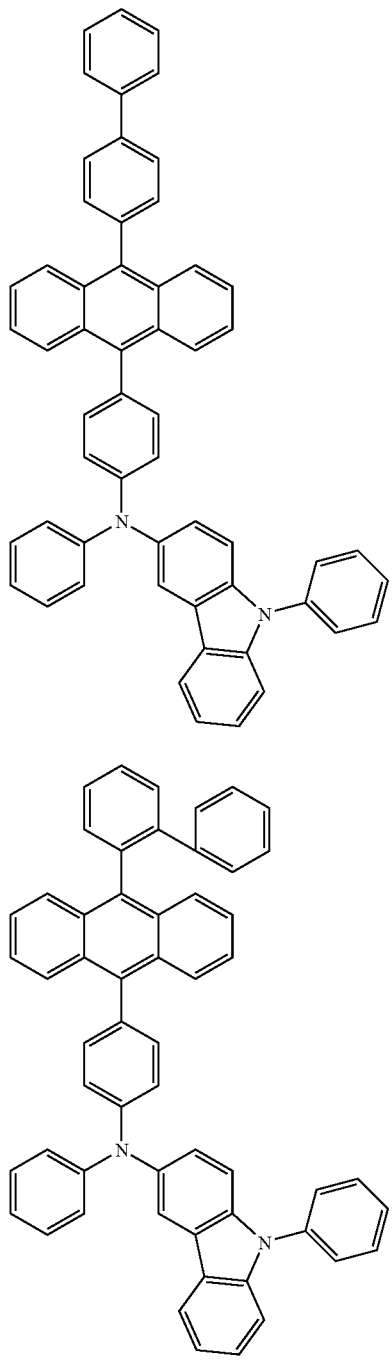
(49)
(50)
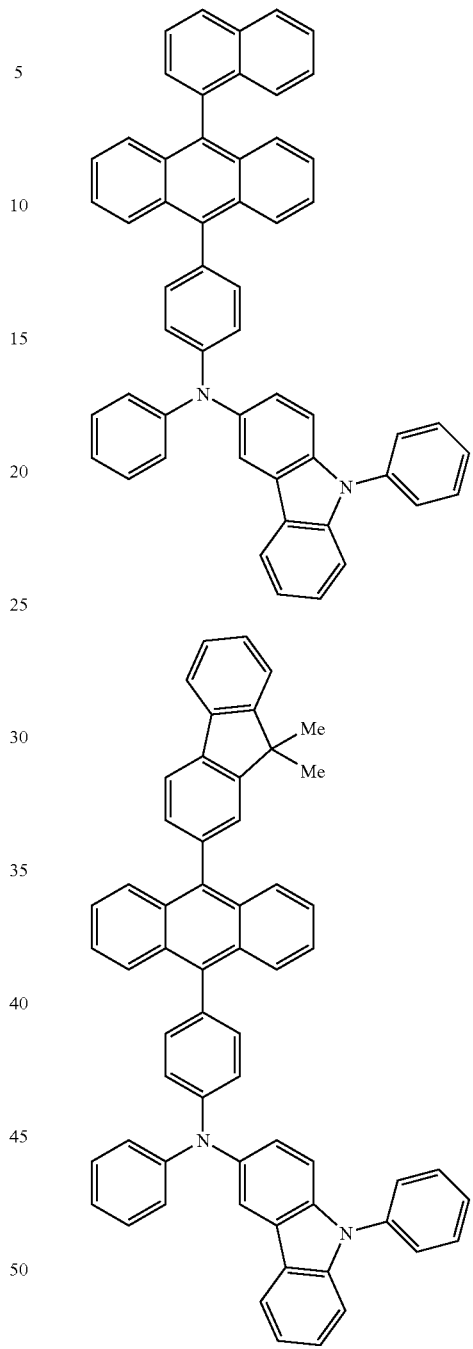
(51)

(52)
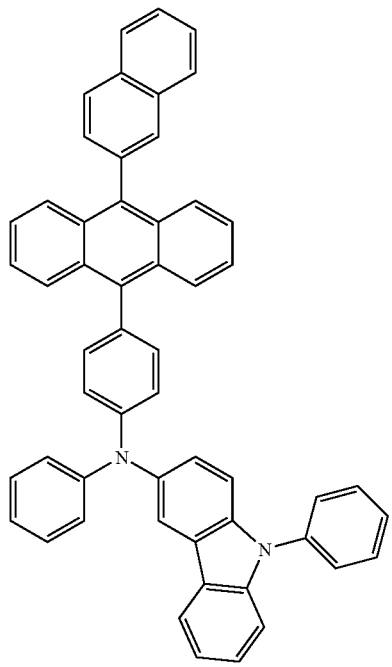
(53)
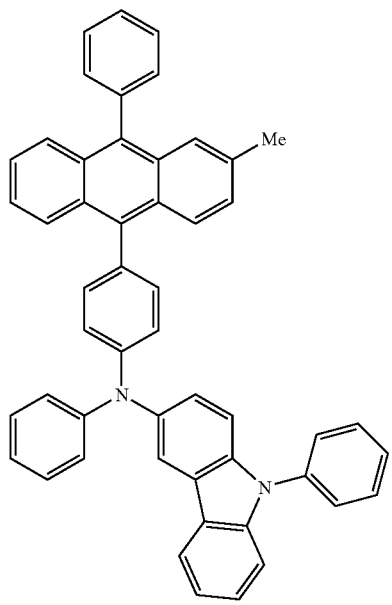
(54)
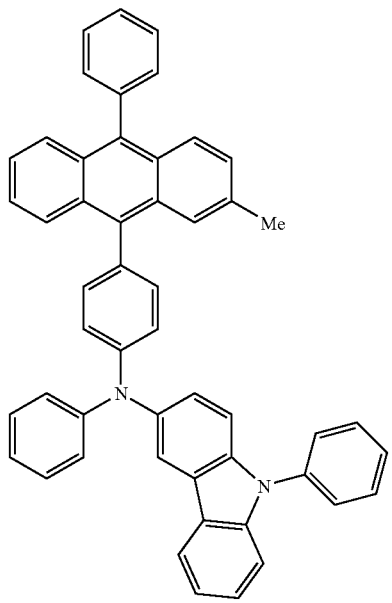
(55)
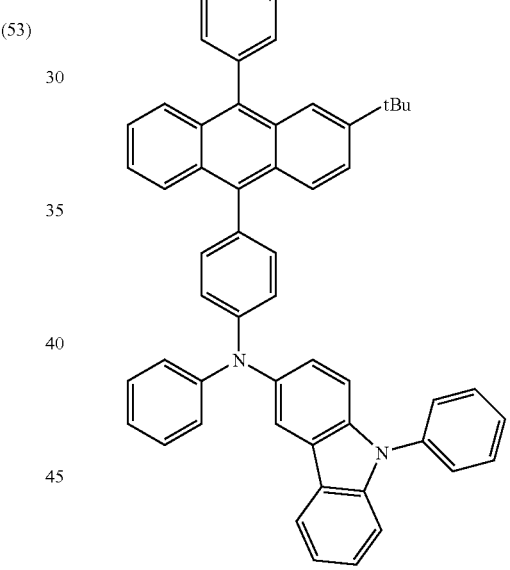

(56)
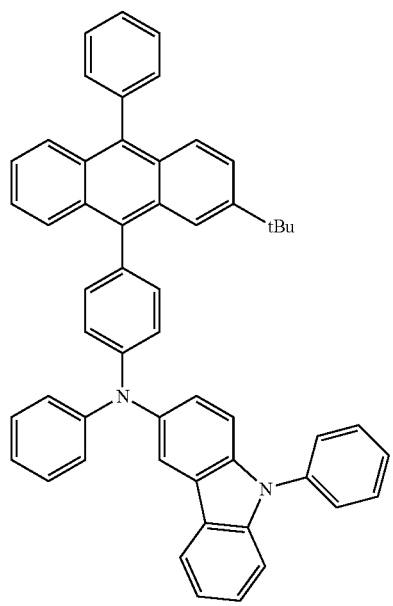
(57)
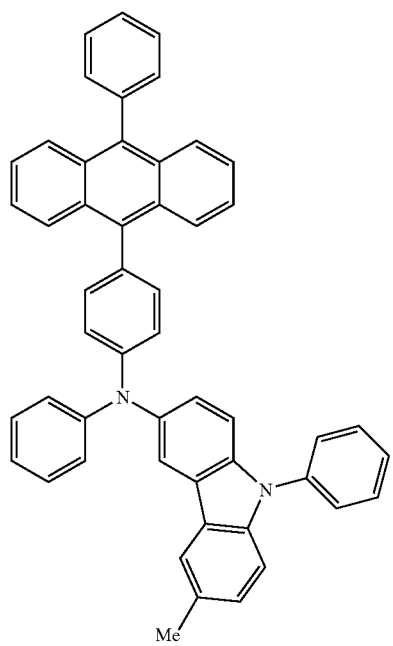
(58)
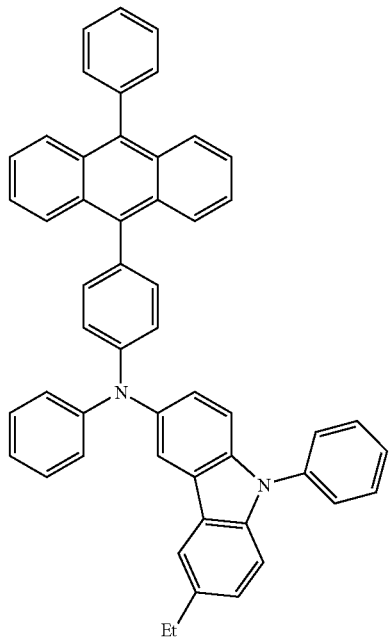
(59)
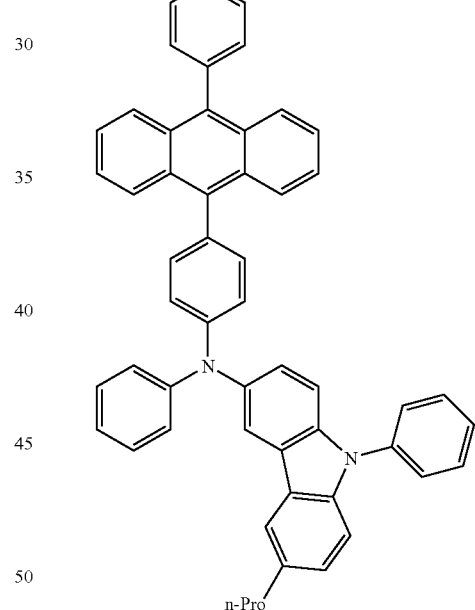

(60)
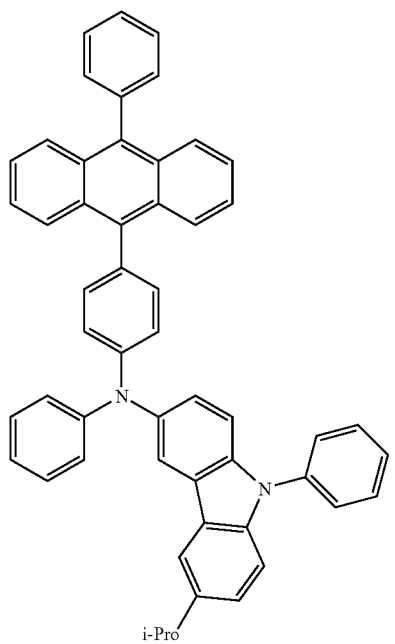
(61)
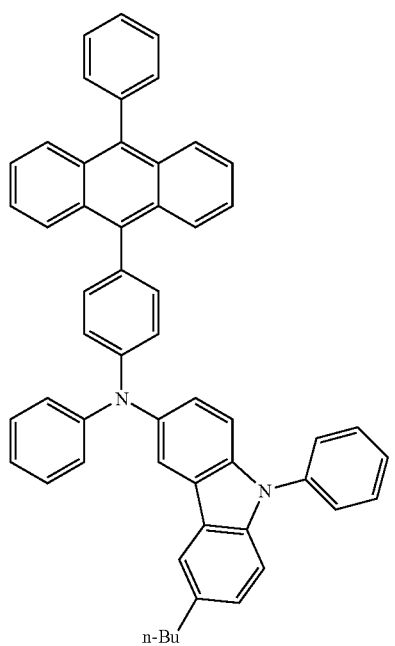
(62)
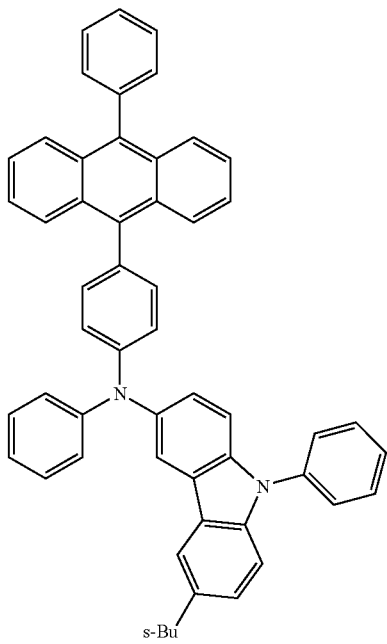
(63)
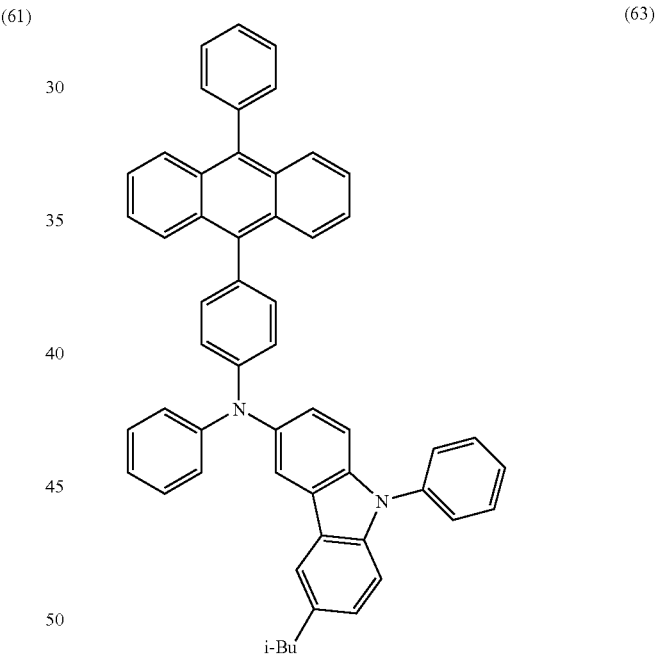

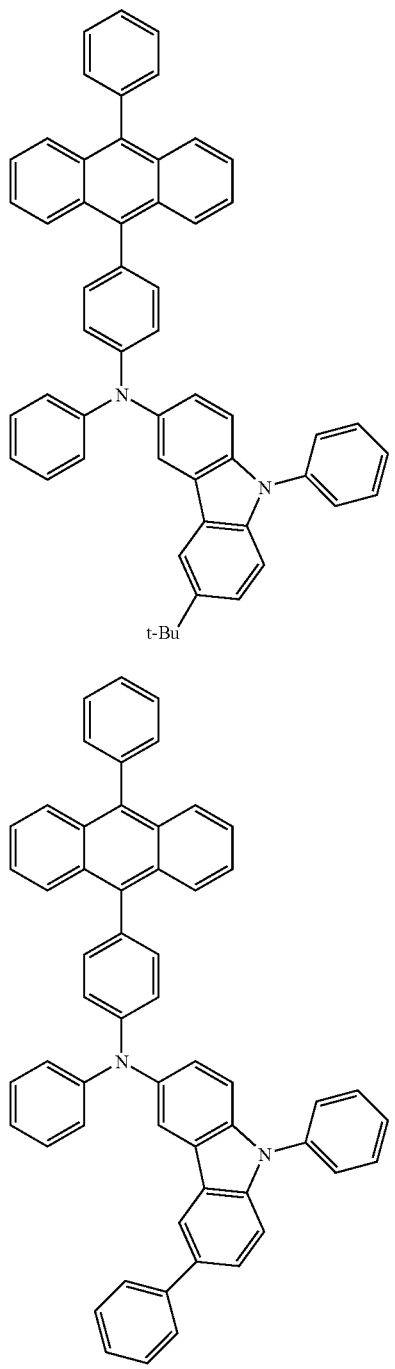
(64)
(65)
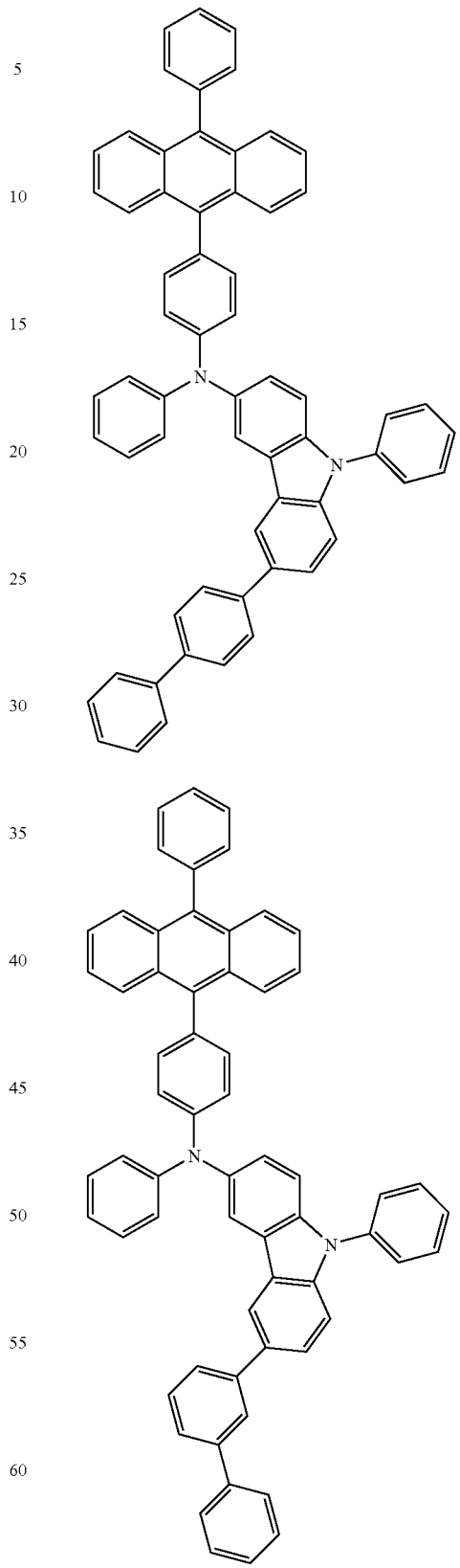
(66)
(67)

(68)
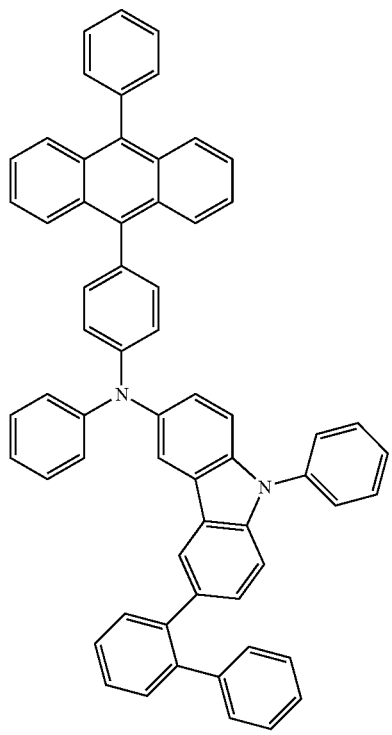
(69)
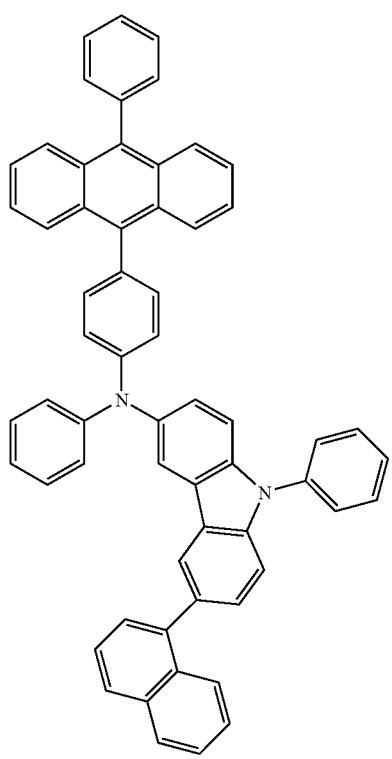
(70)
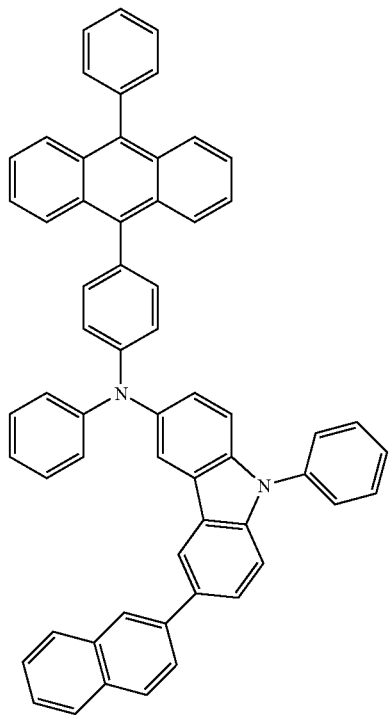
(71)
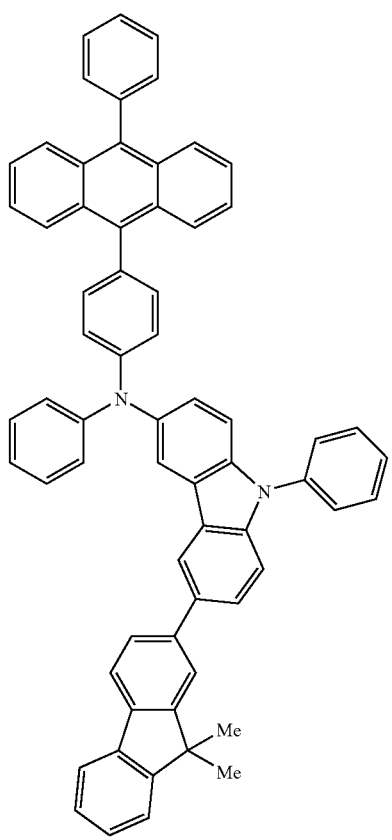

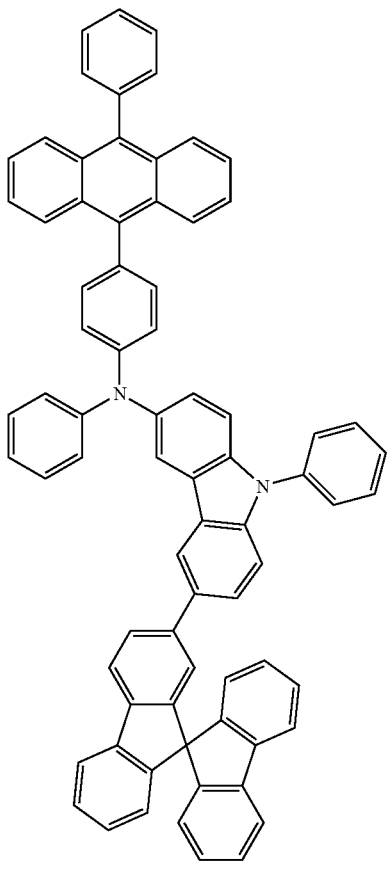

(72)

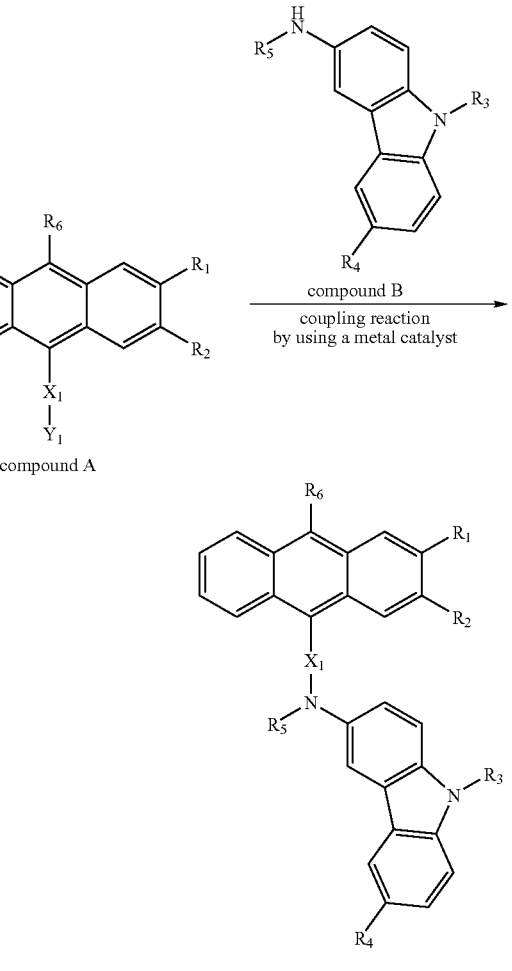

(a-1)

As represented by the following synthetic scheme (a-1), for example, the anthracene derivative of this embodiment mode can be obtained in such a manner that a compound A having an anthracene skeleton such as 9-aryl-10-(arylhalide)anthracene and a compound B having an N-aryl-N-(3-(9-alkyl)carbazolyl)amine skeleton or an N-aryl-N-(3-(9-aryl)carbazolyl)amine skeleton are synthesized by coupling reaction using a metal catalyst such as a palladium catalyst. Note that in the compound B, carbazole may have an aryl substituent or alkyl substituent, and a substitution site is not limited; however, the 6-position of the substitution site is preferable. In addition, a palladium catalyst is not limited particularly; however, bis(dibenzylideneacetone)palladium(0) (abbreviation: Pd(dba)$_2$) or palladium acetate(0) (abbreviation: Pd(OAc)$_2$) is preferable.

In the synthetic scheme (a-1), $R_1$ and $R_2$ each represent either hydrogen or an alkyl group having 1 to 4 carbon atoms. $R_3$ represents any one of hydrogen, an alkyl group having 1 to 4 carbon atoms or an aryl group having 6 to 25 carbon atoms. $R_4$ represents either an alkyl group having 1 to 4 carbon atoms or an aryl group having 6 to 25 carbon atoms. $R_5$ represents an aryl group having 6 to 25 carbon atoms. $R_6$ represents an aryl group having 6 to 25 carbon atoms. The aryl group may have a substituent or no substituent. $X_1$ represents an arylene group having 6 to 25 carbon atoms. The arylene group may have a substituent or no substituent. In addition, $Y_1$ represents halogen. Although there is no particular limitation of halogen, bromine or iodine is preferable.

In addition, the aforementioned compound A can be obtained by a method represented by the following synthetic scheme (a-2), for example. First, by synthesizing a compound C containing a 9-anthracene halide skeleton and arylboronic acid by coupling reaction using a metal catalyst such as a palladium catalyst, a compound D containing a 9-arylanthracene skeleton in which an aryl group is introduced into the 9-position is synthesized. Note that halogen in the compound C is preferably bromine or iodine. In addition, boronic acid in arylboronic acid may be protected with an alkyl group or the like. Note that although there is no particular limitation of a palladium catalyst, Pd(dba)$_2$ or Pd(OAc)$_2$ is preferable.

Next, by halogenating (bromination or iodination is preferable, and iodination is more preferable) the synthesized compound D, a compound E containing a 9-aryl-10-anthracene halide skeleton is synthesized. The compound A having a 9-aryl-10-(arylhalide)anthracene skeleton is obtained in such a manner that the synthesized compound E and aryl halide boronic acid are synthesized by coupling reaction using a metal catalyst such as a palladium catalyst. Note that boronic acid in aryl halide boronic acid may be protected with an alkyl group or the like. In addition, halogen is preferably bromine or iodine.

F; compared to a case of using bromine as a substituent. In addition, although there is no particular limitation of a palladium catalyst, $Pd(dba)_2$ or $Pd(OAc)_2$ is preferable.

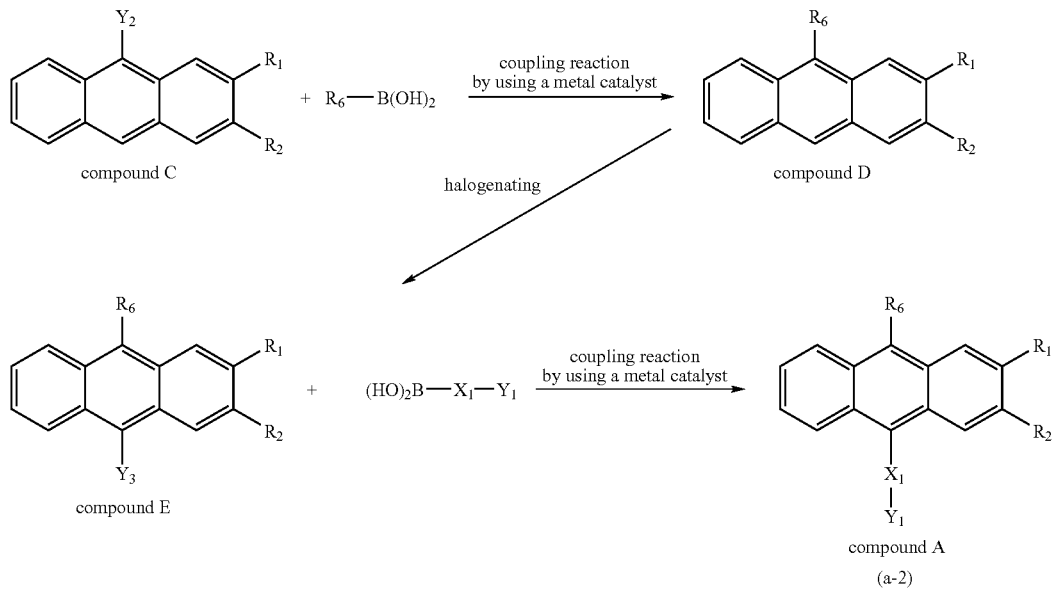

In the synthetic scheme (a-2), $R_1$ and $R_2$ each represent either hydrogen or an alkyl group having 1 to 4 carbon atoms. $R_6$ represents an aryl group having 6 to 25 carbon atoms. The aryl group may have a substituent or no substituent. $X_1$ represents an arylene group having 6 to 25 carbon atoms. The arylene group may have a substituent or no substituent. In addition, $Y_1$, $Y_2$ and $Y_3$ in the formula each represent halogen. Although there is no particular limitation of halogen, bromine or iodine is preferable. It is particularly preferable that $Y_3$ in the compound E be iodine and $Y_1$ in aryl halide boronic acid be bromine. In coupling reaction of the compound E with aryl halide boronic acid, when $Y_3$ is iodine and $Y_1$ is bromine, coupling reaction of iodine compound with boronic acid compound can be selectively performed. That is, since a side reaction such as homocoupling reaction of aryl halide boronic acid can be suppressed, generation of a by-product can be suppressed. Therefore, the compound A can be obtained in high yield, and the compound A can be easily obtained.

In addition, the compound B can be obtained by a method represented by the following synthetic scheme (a-3), for example. First, by halogenating (bromination or iodination is preferable, and iodination is more preferable) a compound F containing carbazole in a skeleton, hydrogen of the 3- or 6-position is substituted for a halogen substituent to synthesize a compound G. Then, the compound B having an N-aryl-N-(3-(9-alkyl)carbazolyl)amine skeleton or an N-aryl-N-(3-(9-aryl)carbazolyl)amine skeleton is obtained in such a manner that the synthesized compound G and aryl amine are synthesized by coupling reaction using a metal catalyst such as a palladium catalyst. Note that reaction time of the coupling reaction with aryl amine can be shortened in the case of using iodine as a substituent in halogenation of the compound

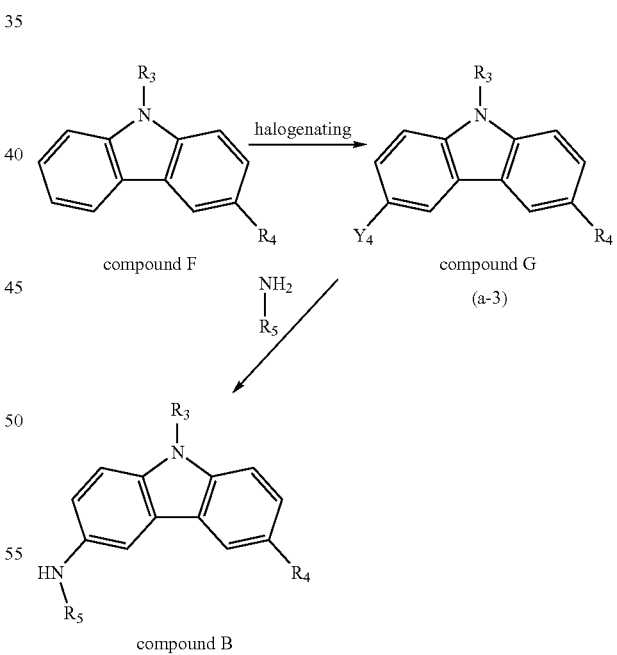

In the synthetic scheme (a-3), $R_3$ represents any one of hydrogen, an alkyl group having 1 to 4 carbon atoms or an aryl group having 6 to 25 carbon atoms. The aryl group may have a substituent or no substituent. $R_4$ represents either an alkyl group having 1 to 4 carbon atoms or an aryl group having 6 to 25 carbon atoms. The aryl group may have a substituent or no substituent. $R_5$ represents an aryl group having 6 to 25 carbon atoms. The aryl group may have a substituent or no substituent. In addition, $Y_4$ represents halogen. Although there is no particular limitation of halogen, bromine or iodine is preferable.

Note that a synthetic method of the anthracene derivative of the present invention is not limited to the aforementioned method, and another synthetic method may be used.

Embodiment Mode 2

In this embodiment mode, a light-emitting element using the anthracene derivative of the present invention is described.

FIG. 1 shows a schematic diagram of one example of an element structure of a light-emitting element of the present invention. A light-emitting element in this embodiment mode has a structure in which a light-emitting layer is interposed between a pair of electrodes (an anode and a cathode). Note that the element structure is not limited to this, and a well-known structure can be appropriately selected in accordance with its purpose.

FIG. 1 shows an example of a light-emitting element having a light-emitting layer 113 between a first electrode 101 and a second electrode 102. The light-emitting layer 113 includes the anthracene derivative of the present invention. In addition, either one of the first electrode 101 and the second electrode 102 becomes an anode, and the other thereof becomes a cathode. In the present invention, an anode indicates an electrode for injecting holes to a light-emitting layer, while a cathode indicates an electrode for injecting electrons to a light-emitting layer. Note that in this embodiment mode, the first electrode 101 is an anode and the second electrode 102 is a cathode.

In the light-emitting element of this embodiment mode, holes injected from the first electrode 101 side and electrons injected from the second electrode 102 side are recombined in the light-emitting layer 113, and the anthracene derivative of the present invention is in an excited state. The excited anthracene derivative of the present invention emits light in returning to a ground state. The anthracene derivative of the present invention serves as a light-emitting substance. Note that the light-emitting substance refers to a substance which has high quantum efficiency of light emission and exhibits a light emission with a desired emission wavelength when the light-emitting substance returns from an excited state to a ground state.

In addition, the light-emitting element of this embodiment mode has a structure in which a hole injecting layer 111 and a hole transporting layer 112 are sequentially stacked between the first electrode 101 and the light-emitting layer 113. In the present invention, the hole injecting layer 111 has a function of helping injection of holes from the first electrode 101 side to the hole transporting layer 112. By providing the hole injecting layer 111 in this manner, a difference in ionization potential between the first electrode 101 and the hole transporting layer 112 is reduced, and holes can be easily injected. As a result, a driving voltage of the light-emitting element can be reduced. In addition, the hole transporting layer 112 has a function of transporting holes injected from the first electrode 101 side to the light-emitting layer 113. As described above, by providing the hole transporting layer 112, a distance between the first electrode 101 and the light-emitting layer 113 can be increased. As a result, quenching of light due to metal contained in the first electrode 101 or the like can be prevented.

Further, the light-emitting element of this embodiment mode has a structure in which an electron transporting layer 114 and an electron injecting layer 115 are sequentially stacked between the light-emitting layer 113 and the second electrode 102. In the present invention, the electron transporting layer 114 has a function of transporting electrons injected from the second electrode 102 side to the light-emitting layer 113. In this manner, by providing the electron transporting layer 114, a distance between the second electrode 102 and the light-emitting layer 113 can be increased. As a result, quenching of light due to metal contained in the second electrode 102 or the like can be prevented. In addition, the electron injecting layer 115 has a function of helping injection of electrons from the second electrode 102 side to the electron transporting layer 114. By providing the electron injecting layer in this manner, a difference in electron affinity between the second electrode 102 and the electron transporting layer 114 is reduced, and electrons can be easily injected. As a result, a driving voltage of the light-emitting element can be reduced.

The first electrode 101, the second electrode 102, and each layer located between the first electrode 101 and the second electrode 102 are specifically described below.

As the anode (first electrode 101), a known material can be used, and metal, an alloy, a conductive compound, or a mixture thereof each having a high work function (specifically, 4.0 eV or more) is preferably used. Specifically, a transparent conductive layer containing a light transmitting conductive material may be used, and an indium oxide containing tungsten oxide, indium zinc oxide containing tungsten oxide, an indium oxide containing titanium oxide, indium tin oxide containing titanium oxide, or the like can be employed. Alternatively, indium tin oxide (ITO), indium zinc oxide (IZO), indium tin oxide added with silicon oxide (ITSO), or the like can be used. Further alternatively, an element selected from gold (Au), platinum (Pt), nickel (Ni), tungsten (W), chromium (Cr), zinc (Zn), tin (Sn), indium (In), molybdenum (Mo), iron (Fe), cobalt (Co), copper (Cu), or palladium (Pd), or an alloy material having the aforementioned element as a main component, for example, titanium nitride (TiN), titanium silicon nitride ($TiSi_xN_y$), tungsten silicide ($WSi_x$), tungsten nitride ($WN_x$), tungsten silicide nitride ($WSi_xN_y$), niobium nitride (NbN), or the like can be used. Note that the anode may be formed using single-layer film or a stacked-layer film of these materials by a method such as a sputtering method or an evaporation method. In addition, in a case of using a conductive material, a sol-gel method or the like may be employed.

In addition, an example of a composition ratio in each light-transmitting conductive material is described. For example, as for the composition ratio of indium oxide containing tungsten oxide, tungsten oxide may be 1.0 wt % and indium oxide may be 99.0 wt %. As for the composition ratio of indium zinc oxide containing tungsten oxide, tungsten oxide may be 1.0 wt %, zinc oxide may be 0.5 wt %, and indium oxide may be 98.5 wt %. As for the composition ratio of indium oxide containing titanium oxide, titanium oxide may be 1.0 to 5.0 wt % and indium oxide may be 99.0 to 95.0 wt %. As for the composition ratio of indium tin oxide (ITO), tin oxide may be 10.0 wt % and indium oxide may be 90.0 wt %. As for the composition ratio of indium zinc oxide (IZO), zinc oxide may be 10.7 wt % and indium oxide may be 89.3 wt %. Further, as for the composition ratio of indium tin oxide containing titanium oxide, titanium oxide may be 5.0 wt %, tin oxide may be 10.0 wt %, and indium oxide may be 85.0 wt %. Note that the composition ratios described above are just examples, and the composition ratio may be set appropriately.

A cathode (second electrode 102) can be formed using a known material. It is preferable to use metal, an alloy, a conductive compound, or a mixture thereof each having a low work function (specifically, 3.8 eV or less). Specifically, metal belonging to Group 1 or 2 of the periodic table, that is, alkali metal such as lithium (Li) and cesium (Cs), alkaline earth metal such as magnesium (Mg), calcium (Ca), and strontium (Sr), an alloy containing these substances (such as an alloy of Mg and Ag and an alloy of Al and Li), rare earth metal such as europium (Er) and ytterbium (Yb), an alloy containing these substances, and the like can be used. However, when using an electron injecting layer having a high electron injecting property, a material having a high work function, i.e., a material, which is generally used for an anode, can be used to form a cathode. For example, a cathode can be formed using metal or a conductive inorganic compound such as Al, Ag, or ITO. Note that the cathode may be formed using a single-layer film or stacked-layer films using the aforementioned material by a method such as a sputtering method or an evaporation method.

It is preferable that the hole injecting layer 111 be formed of a substance whose ionization potential is lower than that of a substance contained in the hole transporting layer 112 and whose ionization potential is higher than that of a substance contained in the first electrode 101, or a substance in which an energy band is bent when provided as a thin film with a thickness of 1 to 2 nm between the hole transporting layer 112 and the first electrode 101. As a specific example of a substance which can be used for forming the hole injecting layer 111, the following can be used: a phthalocyanine compound such as phthalocyanine (abbreviation: $H_2Pc$) or copper phthalocyanine (CuPc), a polymer compound such as poly(ethylene dioxythiophene)/poly(styrenesulfonate)solution (PEDOT/PSS), or the like. In other words, the hole injecting layer 111 can be formed by selecting a substance from hole transporting substances so that ionization potential in the hole injecting layer 111 is relatively lower than that in the hole transporting layer 112. Note that the hole transporting substance is a substance whose hole mobility is higher than electron mobility and whose value of a ratio of hole mobility with respect to electron mobility (=hole mobility/electron mobility) is preferably larger than 100. Further, it is preferable that the first electrode 101 be formed using a substance having a high work function such as indium tin oxide, in a case of providing the hole injecting layer 111.

It is preferable that the hole transporting layer 112 be formed using a hole transporting substance, especially a substance having a hole mobility of $1\times10^6$ $cm^2/Vs$ or more. As a specific example of a substance which can be used for forming the hole transporting layer 112, the following can be used: 4,4'-bis[N-(1-napthyl)-N-phenylamino]biphenyl (abbreviation: NPB), 4,4'-bis[N-(3-methylphenyl)-N-phenylamino]biphenyl (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis{N-[4-(NAN-di-m-tolylamino)phenyl]-N-phenylamino}biphenyl (abbreviation: DNTPD), 1,3,5-tris[N,N-di(m-tolyl)amino]benzene (abbreviation: m-MTDAB), 4,4',4''-tris(N-carbazolyl)triphenylamine (abbreviation: TCTA), phthalocyanine (abbreviation: $H_2Pc$), copper phthalocyanine (abbreviation: CuPc), vanadyl phthalocyanine (abbreviation: VOPc), 4,4'-bis[N-(4-biphenylyl)-N-phenylamino]biphenyl (abbreviation: BBPB), or the like. Note that it is more preferable that the hole transporting layer 112 be formed by selecting especially a substance whose energy gap is larger than that of a substance which is used as a host among hole transporting substances. In addition, the hole transporting layer 112 may have a multilayer structure in which two or more of the layers formed using the above-described substance are combined.

For the light-emitting layer 113, a single-layer film having only one kind of anthracene derivative among anthracene derivatives of the present invention described in Embodiment Mode 1 can be used. Alternatively, a layer containing, as its main component, a substance (referred to as a host) having a higher energy gap than each anthracene derivative and higher ionization potential than each anthracene derivative, in which one of the anthracene derivatives of the present invention described in Embodiment Mode 1 is dispersed, can be used. Accordingly, by dispersing the anthracene derivative of the present invention into the layer with the host as a main component, quenching of light from each anthracene derivative due to concentration of each anthracene derivative itself can be prevented. Note that the energy gap refers to energy gap between a LUMO level and a HOMO level.

More specifically, a substance used as a host preferably is a substance having an electron transporting property which is higher than a hole transporting property. As such a substance, for example, an anthracene derivative such as 2-tert-butyl-9,10-di(2-naphthyl)anthracene (abbreviation: t-BuDNA), 9-[4-(N-carbazolyl)]phenyl-10-phenylanthracene (abbreviation: CzPA), or diphenyl anthracene; a phenanthroline derivative such as bathocuproin (abbreviation: BCP); an oxadiazole derivative, or a triazine derivative can be used. One or two or more of these substances may be selected to be mixed so that the anthracene derivative of the present invention described in Embodiment Mode 1 is in a dispersion state. By making the light-emitting layer 113 have such a structure, holes can be efficiently trapped in the anthracene derivative of the present invention described in Embodiment Mode 1. As a result, a light-emitting element having favorable light emission efficiency can be obtained. Moreover, the electron transporting layer 114 is formed of a substance having a small energy gap in many cases, and excited energy easily moves from the light-emitting layer 113; however, by making the light-emitting layer 113 have the above-described structure, a recombination region (a light-emitting region) of holes and electrons in the light-emitting layer 113 is formed on the hole transporting layer 112 side, and the excited energy can be prevented from moving to the electron transporting layer 114. As a result, chromaticity can be prevented from deteriorating due to light emission generated in a different layer from the light-emitting layer 113. In the case where the light-emitting layer 113 is a layer in which a plurality of compounds is mixed (for example, a layer in which the anthracene derivative of the present invention is dispersed into the layer with the host as a main component), the light-emitting layer 113 may be formed by a co-evaporation method. Here, a co-evaporation method refers to an evaporation method by which raw materials are vaporized from a plurality of evaporation sources provided in one processing chamber and the vaporized raw materials are mixed in a gaseous state to be deposited on an object to be processed.

It is preferable that the electron transporting layer 114 be formed using an electron transporting substance, especially a substance having electron mobility of $1\times10^{-6}$ $cm^2/Vs$ or more. Note that the electron transporting substance is a substance whose electron mobility is higher than hole mobility and whose value of a ratio of electron mobility with respect to hole mobility (=electron mobility/hole mobility) is larger than 100. As a specific example of a substance which can be used for forming the electron transporting layer 114, the following can be used: 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation:

OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), 4,4-bis(5-methylbenzoxazol-2-yl)stilbene (abbreviation: BzOs), or the like as well as a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]-quinolinato)beryllium (abbreviation: BeBq$_2$), bis(2-methyl-8-quinolinolato)-4-phenylphenolato-aluminum (abbreviation: BAlq), bis[2-(2-hydroxyphenyl)benzoxazolate]zinc (abbreviation: Zn(BOX)$_2$), or bis[2-(2-hydroxyphenyl)benzothiazolate]zinc (abbreviation: Zn(BTZ)$_2$). Note that it is more preferable that the electron transporting layer 114 be formed by selecting especially a substance whose energy gap is larger than that of a substance which is used as a host among electron transporting substances. In addition, the electron transporting layer 114 may have a multilayer structure in which two or more of the layers formed using the above-described substance are combined.

The electron injecting layer 115 can be formed using a substance having relatively higher electron affinity than that of a substance used for forming the electron transporting layer 114, which is selected from substances that can be used for forming the electron transporting layer 114, such as BPhen, BCP, p-EtTAZ, TAZ, and BzOs. In addition, the electron injecting layer 115 may contain an inorganic substance such as alkali metal such as lithium (Li) or cesium (Cs); oxide of alkali metal such as lithium oxide (Li$_2$O), potassium oxide (K$_2$O), sodium oxide (Na$_2$O); oxide of alkaline earth metal such as calcium oxide (CaO) or magnesium oxide (MgO); fluoride of alkali metal such as lithium fluoride (LiF) or cesium fluoride (CsF); fluoride of alkaline earth metal such as calcium fluoride (CaF$_2$); or alkaline earth metal such as magnesium (Mg) or calcium (Ca). In addition, the electron injecting layer 115 may have a structure including the organic substance as described above or may have a structure including an inorganic substance such as fluoride of alkali metal such as LiF or fluoride of alkaline earth metal such as CaF$_2$. By providing the electron injecting layer 115 as a thin film having a thickness of 1 to 2 nm by using an inorganic substance such as fluoride of alkali metal such as LiF or fluoride of alkaline earth metal such as CaF$_2$, an energy band of the electron injecting layer 115 is bent, or tunnel current flows; accordingly, electrons are easily injected from the second electrode 102 side to the electron transporting layer 114.

A hole generating layer may be provided instead of the hole injecting layer 111 of this embodiment mode. Note that the hole generating layer generates holes. The hole generating layer can be formed by mixing at least one substance selected from hole transporting substances and a substance showing an electron accepting property with respect to the hole transporting substance. Here, as the hole transporting substance, the similar substance to the substance which can be used for forming the hole transporting layer 112 can be used. As the substance showing an electron accepting property, metal oxide such as molybdenum oxide, vanadium oxide, ruthenium oxide, or rhenium oxide can be used.

In addition, an electron generating layer may be provided instead of the electron injecting layer 115 of this embodiment mode. The electron generating layer generates electrons. The electron generating layer can be formed by mixing at least one substance selected from electron transporting substances and a substance showing an electron donating property with respect to the electron transporting substance. Here, as the electron transporting substance, the similar substance to the substance which can be used for forming the electron transporting layer 114 can be used. As the substance showing an electron donating property, a substance selected from alkali metal and alkaline earth metal, specifically lithium (Li), calcium (Ca), sodium (Na), potassium (K), magnesium (Mg), or the like can be used.

A method for manufacturing a light-emitting element of this embodiment mode as described above is not particularly limited. For example, a manufacturing method in which, after the first electrode 101 is formed, the hole injecting layer 111, the hole transporting layer 112, the light-emitting layer 113, the electron transporting layer 114, and the electron injecting layer 115 are sequentially stacked thereover and the second electrode 102 is formed finally, can be employed. Alternatively, a manufacturing method in which, after the second electrode 102 is formed, the electron injecting layer 115, the electron transporting layer 114, the light-emitting layer 113, the hole transporting layer 112, and the hole injecting layer 111 are sequentially stacked thereover and the first electrode 101 is formed finally, can be employed. Note that each of the hole injecting layer 111, the hole transporting layer 112, the light-emitting layer 113, the electron transporting layer 114, and the electron injecting layer 115 may be formed by any of an evaporation method, an ink jetting method, an application method, or the like. In addition, the first electrode 101 or the second electrode 102 may be formed by a sputtering method, an evaporation method, or the like.

The light-emitting element of the present invention having the above-described structure is manufactured by using the anthracene derivative with excellent light-emitting efficiency of the present invention; therefore, a light-emitting element with high efficiency can be obtained. In addition, a light-emitting element using the anthracene derivative of the present invention can be driven at low voltage for a long life. Therefore, the light-emitting element of the present invention can achieve very high power efficiency and low power consumption.

The light-emitting element of the present invention is manufactured by using a compound containing an anthracene skeleton and an amine skeleton such as the anthracene derivative of the present invention; therefore, there are a few changes in characteristics of the light-emitting element in accordance with a change of characteristics of a light-emitting substance due to repeated oxidation reactions, and stable light emission can be generated for a long time. In addition, the light-emitting element of the present invention is formed using the anthracene derivative of the present invention. Therefore, an element with very high external quantum efficiency can be obtained; accordingly, an element with high light-emitting efficiency can be obtained. Particularly, since an element can be driven at low voltage, an element with high current efficiency and high power efficiency can be obtained. Further, since the anthracene derivative of the present invention can generate blue light emission, a blue light-emitting element with high current efficiency and high power efficiency can be obtained.

Embodiment Mode 3

In this embodiment mode, a light-emitting element, which uses the anthracene derivative of the present invention as a host (a substance which is included in a light-emitting layer together with a light-emitting substance, and which makes the light-emitting substance in a dispersion state), is described with reference to FIG. 2. Note that description for components other than a light-emitting layer 213 is omitted since the light-emitting element has the same structure as that of Embodiment Mode 2.

Figure 2:
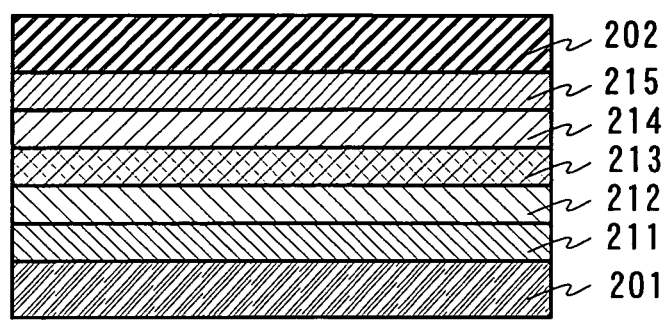
FIG. 2 shows an example of a light-emitting element of the present invention.

A light-emitting element shown in FIG. 2 of this embodiment mode has a light-emitting layer 213 between a first electrode 201 and a second electrode 202. In addition, a hole injecting layer 211 and a hole transporting layer 212 are provided between the first electrode 201 and the light-emitting layer 213, and an electron injecting layer 215 and an electron transporting layer 214 are provided between the second electrode 202 and the light-emitting layer 213. Note that the structure of the light-emitting element is not limited to this, and a well-known structure can be appropriately selected in accordance with its purpose.

In this embodiment mode, the light-emitting layer 213 includes the anthracene derivative described in Embodiment Mode 1, and a light-emitting substance having an energy gap smaller than that of the anthracene derivative of the present invention and having an ionization potential smaller than that of the anthracene derivative. In this case, the anthracene derivative of the present invention serves as a host. Either a fluorescent light-emitting material or a phosphorescent light-emitting material can be used as the light-emitting substrate; however, in a case of using a phosphorescent light-emitting material, it is required that a triplet level of the phosphorescent light-emitting material is lower than that of the anthracene derivative of the present invention. Specifically, a coumarin derivative, an oligophenylene derivative, an oxazole derivative, a stilbene derivative, a quinolone derivative, an acridone derivative, a pyrene derivative, a phenanthrene derivative, and the like can be employed. Note that the material which can be used as a light-emitting substance is not limited to this, and may be a light-emitting substance having an energy gap smaller than that of the anthracene derivative of the present invention and having an ionization potential smaller than that of the anthracene derivative. These light-emitting substances are included in a layer formed using the anthracene derivative of the present invention described in Embodiment Mode 1 so as to be dispersed. In this manner, by using a combination of these light-emitting substances and the anthracene derivative of the present invention serving as a host, a light-emitting element in which light from the host is difficult to be mixed and light caused by the light-emitting substance can be selectively emitted can be obtained.

In the case of forming a layer in which a plurality of compounds is mixed as in the light-emitting layer 213, a co-evaporation method may be used. Here, a co-evaporation method refers to an evaporation method by which raw materials are vaporized from a plurality of evaporation sources provided in one processing chamber and the vaporized raw materials are mixed in a gaseous state to be deposited on an object to be processed.

Embodiment Mode 4

Figure 3:
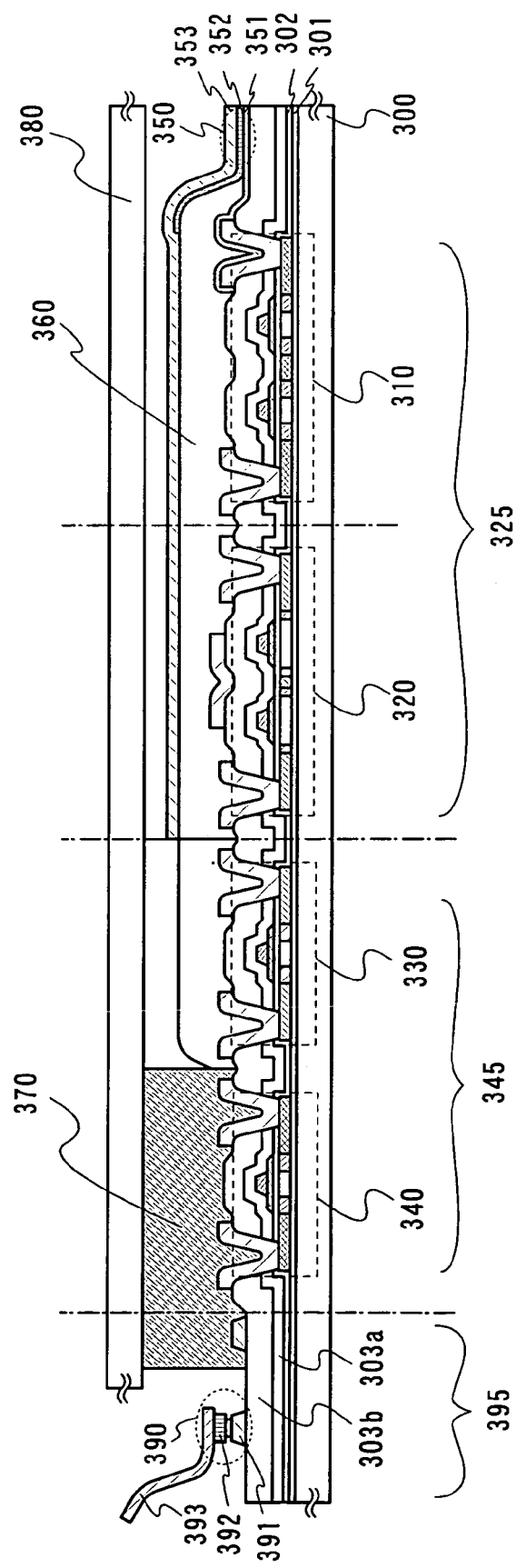
FIG. 3 is a cross-sectional view showing an example of a light-emitting device of the present invention.
Figure 4:
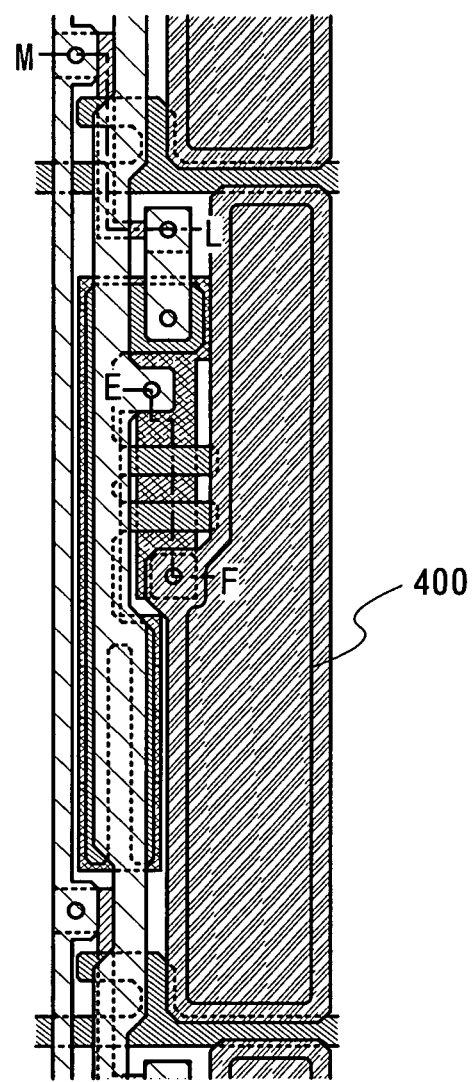
FIG. 4 is a top view showing an example of a pixel portion of a light-emitting device of the present invention.

In this embodiment mode, an example of a light-emitting device (EL light-emitting device) of the present invention is described with a manufacturing method, with reference to FIGS. 3 and 4. Note that in this embodiment mode, description is made of an example of an active matrix light-emitting device in which a pixel portion and a driver circuit portion are formed on the same substrate; however, the present invention is not limited to this, and may be applied to a passive light-emitting device.

First, over a substrate 300, a base insulating film 301 is formed. In the case where light emission is extracted with the substrate 300 side as a display surface, a glass substrate or a quartz substrate having a light-transmitting property may be used as the substrate 300. Alternatively, a light-transmitting plastic substrate having a heat resistant property which can resist processing temperature in a process may also be used. On the other hand, in the case where light emission is extracted with an opposite surface to the substrate 300 side as a display surface, a silicon substrate, a metal substrate, or a stainless steel substrate over which an insulating film is formed may also be used as well as the above substrates. Any substrate can be used as long as the substrate can endure at least generated heat in a process. A glass substrate is used as the substrate 300 in this embodiment mode. Note that the refractive index of a glass substrate is around 1.55.

As the base insulating film 301, an insulating film such as a silicon oxide film, a silicon nitride film, or a silicon oxynitride film is formed to have a single layer or a plurality of layer having two or more layers by a sputtering method, an LPCVD method, a plasma CVD method, or the like. In addition, the base insulating film is not required to be formed when an asperity of the substrate and impurity diffusion from the substrate do not cause a problem.

Next, a semiconductor layer is formed over the base insulating film 301. The semiconductor layer is formed as follows: an amorphous semiconductor film is formed by a sputtering method, an LPCVD method, a plasma CVD method, or the like, and then the amorphous semiconductor film is crystallized by a laser crystallization method, a thermal crystallization method, a thermal crystallization method using a catalytic element such as nickel, or the like to obtain a crystalline semiconductor film. Note that in the case where a thermal crystallization method using a catalytic element such as nickel is used, it is preferable to remove the catalytic element by gettering after crystallization. After that, the crystalline semiconductor film is processed into a desired shape by a photolithography method.

Next, a gate insulating film 302 covering the semiconductor layer is formed. As the gate insulating film 302, an insulating film containing silicon is formed by a plasma CVD method or a sputtering method. In addition, after a single layer structure or a stacked structure of an insulating film containing silicon is formed, surface nitriding treatment using plasma with a microwave may be performed to form the gate insulating film 302.

Next, a gate electrode is formed over the gate insulating film 302 The gate electrode may be formed using a conductive material such as refractory metal such as tungsten (W), chromium (Cr), tantalum (Ta), tantalum nitride (TaN) or molybdenum (Mo), or an alloy or a compound containing the refractory metal as a main component by a method such as a sputtering method or an evaporation method. In addition, a gate electrode may have a single-layer structure of these conductive materials or a plurality of layers having two or more layers.

Next, an impurity is added so as to form an impurity region having n-type conductivity or p-type conductivity in each semiconductor layer of transistors 310 to 340 formed in a pixel portion 325 and a driver circuit portion 345. The added impurity may be selected in accordance with each transistor appropriately.

Next, a first interlayer insulating film 303a and a first interlayer insulating film 303b are formed. The first interlayer insulating films 303a and 303b may be formed using an inorganic insulating film such as a silicon oxide film, a silicon nitride film or a silicon oxynitride film, an organic resin film, or a film containing siloxane, and these insulating films may be formed to have a single layer or a plurality of layers having two or more layers. Note that siloxane is a material including a skeleton structure formed by a bond of silicon (Si) and oxygen (O). As a substituent, an organic group containing at least hydrogen (e.g., an alkyl group or aromatic hydrocarbon) is used. A fluoro group may also be used as the substituent. Alternatively, as the substituent, both of an organic group containing at least hydrogen and a fluoro group may be used. In addition, in the case where an inorganic insulating film is formed, a sputtering method, an LPCVD method, a plasma CVD method, or the like may be used. In the case where an organic resin film or a film containing siloxane is formed, an application method may be used. The first interlayer insulating film has a two-layer stacked structure here; however, a single layer or three or more layers may be used as well.

Next, the first interlayer insulating films 303a and 303b are selectively etched, and contact holes reaching the semiconductor layer are formed. Then, source electrodes and drain electrodes reaching the semiconductor layer through the contact holes are formed. After metal films are stacked by a sputtering method, a metal stacked film is selectively etched by a photolithography method to form the source electrodes and the drain electrodes.

Through the above steps, a first transistor 310 and a second transistor 320 disposed in a pixel portion 325, and a third transistor 330 and a fourth transistor 340 disposed in a driver circuit portion 345 are formed. Note that in this embodiment mode, the first transistor 310 and the second transistor 320 have a multi-gate structure (a structure having a semiconductor layer including two or more channel formation regions connected in series and two or more gate electrodes for applying an electric field to each channel formation region) in order to reduce off current; however, the present invention is not limited to this, and a single gate structure may be used as well. In addition, the third transistor 330 and the fourth transistor 340 disposed in the driver circuit portion 345 have a single gate structure; however, the present invention is not limited to this, and a multi-gate structure may be used as well.

In addition, the first transistor 310, the third transistor 330, and the fourth transistor 340 have a structure including lightly doped drain regions (LDD regions) overlapped with the gate electrode with the gate insulating film 302 interposed therebetween; however, the present invention is not limited to this, and a structure without an LDD region may be used.

In addition, the second transistor 320 has a structure including lightly doped drain regions (LDD regions) which are not overlapped with the gate electrode with the gate insulating film 302 interposed therebetween; however, the present invention is not limited to this, and a structure without an LDD region may be used.

Note that in the driver circuit portion 345, the third transistor 330 is an n-channel transistor and the fourth transistor 340 is a p-channel transistor, and a CMOS circuit is formed by complementarily connecting the third transistor 330 and the fourth transistor 340, so that various kinds of circuits can be realized.

Then, a light-emitting element 350 is formed. First, a first electrode 351 (an anode or a cathode of an organic light-emitting element) is formed. Note that the first electrode 351 may be formed in the same manner as in Embodiment Mode 2 and Embodiment Mode 3, and the description is omitted.

Next, a partition layer 360 covering an edge portion of the first electrode 351 is formed. An insulating film using acrylic, siloxane, resist, silicon oxide, polyimide, or the like is formed by an application method, and the obtained insulating film may be formed in a desired shape by a photolithography method to form the partition layer 360.

Note that in FIG. 3, only the first interlayer insulating films 303a and 303b are formed between the light-emitting element 350 and respective transistors 310 to 340; however, a structure provided with a second interlayer insulating film as well as the first interlayer insulating films 303a and 303b may be used. In this case, the first electrode 351 is electrically connected to the first transistor 310 sandwiching the first interlayer insulating films 303a and 303b and the second interlayer insulating film.

Next, a layer 352, a second electrode 353 (a cathode or an anode of an organic light-emitting element) are formed sequentially. Note that the layer 352 includes a light-emitting layer containing the anthracene derivative of the present invention described in Embodiment Mode 2 or Embodiment Mode 3. In addition, the layer 352 may include a hole injecting layer, a hole transporting layer, an electron transporting layer, an electron injecting layer, or the like as well as the light-emitting layer. The layer 352 and the second electrode 353 may be formed in the same manner as in Embodiment Mode 2 and Embodiment Mode 3, and the description is omitted.

Through the above steps, the light-emitting element 350 including the first electrode 351, the layer 352, and the second electrode 353 is formed. Note that the light-emitting element 350 is isolated by the partition layer 360 from another light-emitting element which is adjacently provided.

Next, a sealing substrate 380 is attached with a sealant 370 to seal the light-emitting element 350. That is, the light-emitting device is sealed by a pair of substrates 300 and 380 by surrounding a periphery of a display region with the sealant 370. Note that in this embodiment mode, the sealant 370 is disposed to be overlapped with a terminal portion 395 and the driver circuit portion 345; however, the sealant 370 may be disposed to surround at least the periphery of the display region, and may be disposed only in the terminal portion. In addition, a region surrounded with the sealant 370 may be filled with a filler or a dry inert gas.

Finally, an FPC 393 is attached to a terminal electrode 391 by a known method with an anisotropic conductive layer 392 to form a terminal 390. Note that as for the terminal electrode 391, an electrode which is obtained by the same step as the first electrode 351 is preferably used as a top layer.

FIG. 4 is a top view of the pixel portion, and a cross-section taken along a chain line E-F in FIG. 4 corresponds to a cross-sectional structure of the first transistor 310 in the pixel portion of FIG. 3. In addition, a cross-section taken along a chain line M-L in FIG. 4 corresponds to a cross-sectional structure of the second transistor 320 in the pixel portion of FIG. 3. Note that a solid line denoted by reference numeral 400 in FIG. 4 indicates the periphery border of the partition layer 360. Note that FIGS. 3 and 4 are diagrams which show an example of a light-emitting device of the present invention, and a wire or the like may be changed appropriately depending on a layout.

In the light-emitting device, a light-emitting display surface of the light-emitting device may be provided on either one side or both sides. In the case where both of the first electrode 351 and the second electrode 353 are formed using a transparent conductive layer, light of the light-emitting element 350 is extracted through the substrate 300 and the sealing substrate 380 to both sides. In this case, for the sealing substrate 380 and the filler, a transparent material is preferably used.

In the case where the second electrode 353 is formed of a metal film and the first electrode 351 is formed of a transparent conductive layer, obtained is a structure in which light of the light-emitting element 350 is extracted through only the substrate 300 to one side, namely a bottom emission structure. In this case, for the sealing substrate 380 and the filler, a transparent material is not necessarily used.

In the case where the first electrode 351 is formed of a metal film and the second electrode 353 is formed of a transparent conductive layer, obtained is a structure in which light of the light-emitting element 350 is extracted through only the sealing substrate 380 to one side, namely a top emission structure. In this case, for the substrate 300, a transparent material is not necessarily used.

Materials for the first electrode 351 and the second electrode 353 are required to be selected considering work function. However, each of the first electrode 351 and the second electrode 353 can be either an anode or a cathode depending on a pixel structure. In the case where polarity of the first transistor 310 is a p-channel type, the first electrode 351 may be an anode and the second electrode 353 may be a cathode. In the case where polarity of the first transistor 310 is an n-channel type, the first electrode 351 may be a cathode and the second electrode 353 may be an anode.

Figure 5:
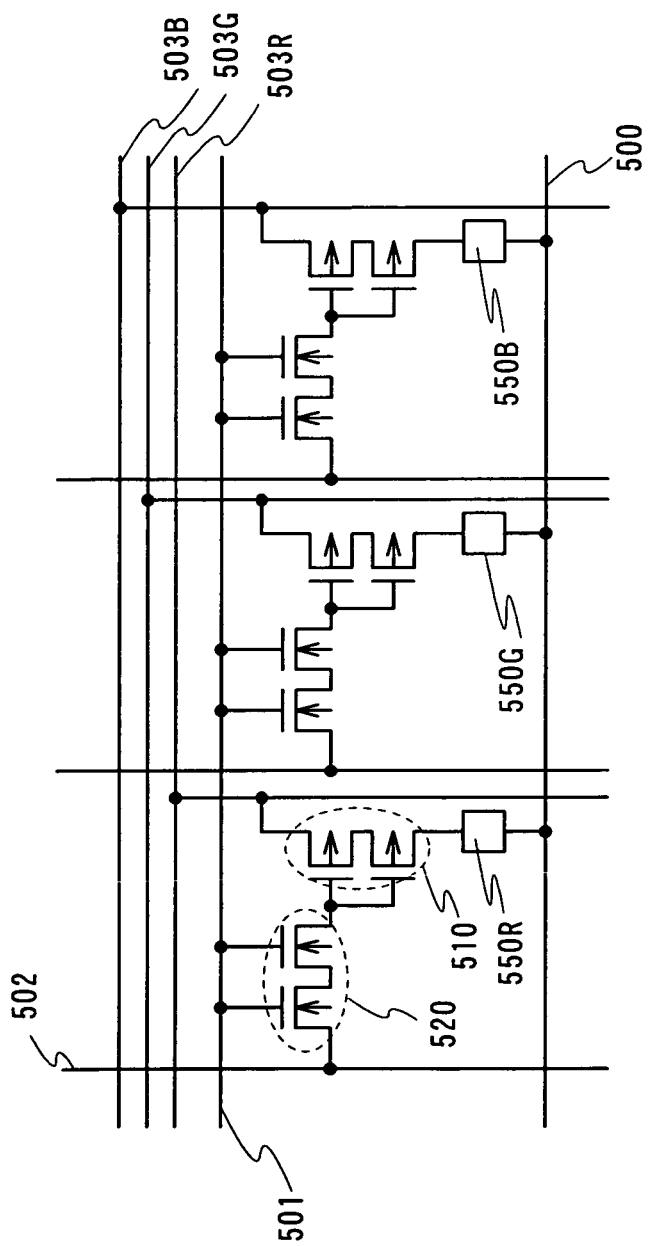
FIG. 5 shows an example of an equivalent circuit of a pixel portion of a light-emitting device of the present invention.

FIG. 5 is an equivalent circuit diagram of the pixel portion of this embodiment mode in the case of a full color display. A transistor 510 in FIG. 5 corresponds to the first transistor 310 in FIG. 3, and a transistor 520 corresponds to the second transistor 320 in FIG. 3. In a pixel for displaying a red color, a light-emitting element 550R emitting red light is connected to a drain region of the transistor 510, and a source region thereof is connected to an anode side power supply line (R) 503R. In addition, the light-emitting element 550R is connected to a cathode side power supply line 500. In a pixel for displaying a green color, a light-emitting element 550G emitting green light is connected to the drain region of the transistor 510, and the source region thereof is connected to an anode side power supply line (G) 503G In addition, in a pixel for displaying a blue color, a light-emitting element 550B emitting blue light is connected to the drain region of the transistor 510, and the source region thereof is connected to an anode side power supply line (B) 503B. Different voltage is applied to the pixels for emitting different colors in accordance with EL materials.

In addition, in the light-emitting device, a driving method for image display is not particularly limited, and for example, a dot sequential driving method, a line sequential driving method, an area sequential driving method or the like may be employed. Typically, the line sequential driving method is used, and besides, a time division gray scale driving method or an area gray scale driving method may be appropriately employed. Further, a video signal inputted to the source line of the light-emitting device may be either an analog signal or a digital signal, and in accordance with the video signal, the driver circuit and the like may be appropriately designed.

Further, in the case of the light-emitting device using a digital video signal, a video signal that is inputted into a pixel has either constant voltage (CV) or constant current (CC). As for the video signal with constant voltage (CV), there are cases where voltage of a signal that is applied to a light-emitting element is constant (CVCV) and where current of a signal that is applied to a light-emitting element is constant (CVCC). In addition, as for the video signal with constant current (CC), there are cases where voltage of a signal that is applied to a light-emitting element is constant (CCCV) and where current of a signal that is applied to a light-emitting element is constant (CCCC).

Further, in the light-emitting device, a protective circuit (e.g., a protective diode) for preventing electrostatic breakdown may also be provided.

As this embodiment mode, by having a light-emitting element containing the anthracene derivative of the present invention, a light-emitting device with low power consumption and light emission with high luminance can be obtained.

Embodiment Mode 5

In this embodiment mode, the example in which an FPC or a driving IC for driving is mounted on a light-emitting device (EL light-emitting device) of the present invention is described with reference to FIGS. 6A and 6B. Note that the structure included in the light-emitting element mounted on this light-emitting display panel is a structure similar to that shown in Embodiment Mode 2 or 3.

Figure 6A:
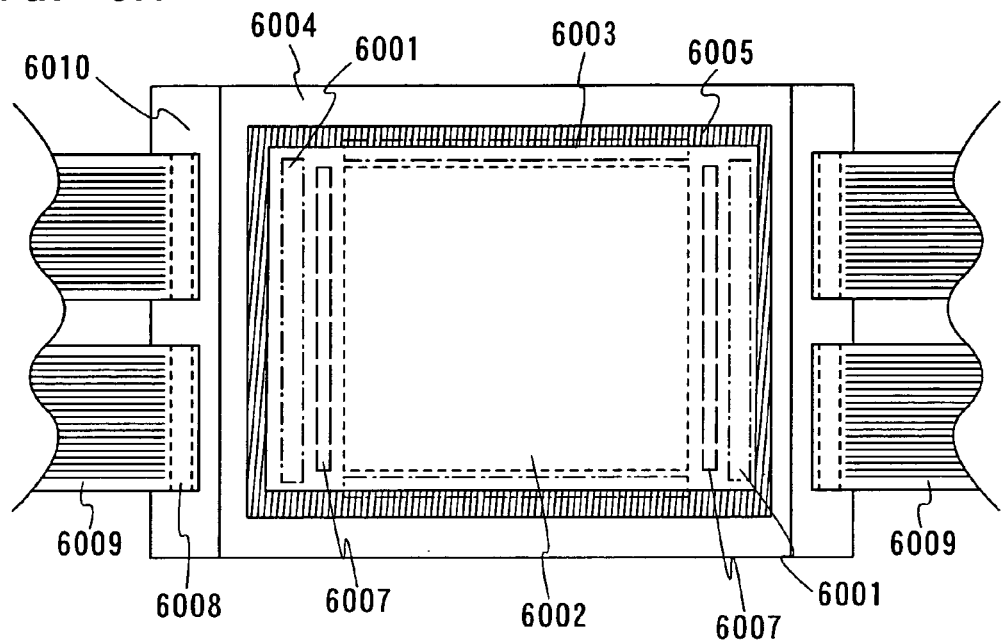
FIGS. 6A and 6B are top views showing an example of a light-emitting device of the present invention.

FIG. 6A shows an example of a top view of a light-emitting device in which FPCs 6009 are attached to four terminal portions 6008 respectively. Over a substrate 6010, a pixel portion 6002 including a light-emitting element and a thin film transistor (TFT), a gate driver circuit 6003 including a TFT, and a first driver circuit 6001 including a TFT are formed. An active layer of the TFTs are formed by using a semiconductor film having a crystal structure, and these circuits are formed over the same substrate. Accordingly, a light-emitting device (EL light-emitting device) that realizes system-on-panel can be manufactured.

Note that the substrate 6010 is covered with a protective film except for a contact portion, and a base layer containing a substance having a photocatalyst function is provided over the protective film.

In addition, two connection regions 6007 provided on both sides of a pixel portion are provided so that a second electrode (cathode) of a light-emitting element is in contact with a wire of a lower layer. A first electrode (anode) of the light-emitting element is electrically connected to the TFT provided in the pixel portion 6002.

A sealing substrate 6004 is fixed to the substrate 6010 with a sealant 6005 surrounding the pixel portion 6002 and the driver circuits 6001 and 6003, and a filler material surrounded by the sealant 6005. Filling may be performed with a filler material containing a transparent drying agent may also be employed. Further, a drying agent may also be provided in a region where the pixel portion does not overlap.

Note that in this embodiment mode, the sealant 6005 is disposed to be partially overlapped with the gate driver circuit 6003 including a TFT; however, the sealant 6005 may be disposed to surround the periphery of the display region. That is, the sealant 6005 may be disposed so as not to be overlapped with the gate driver circuit 6003.

Figure 6B:
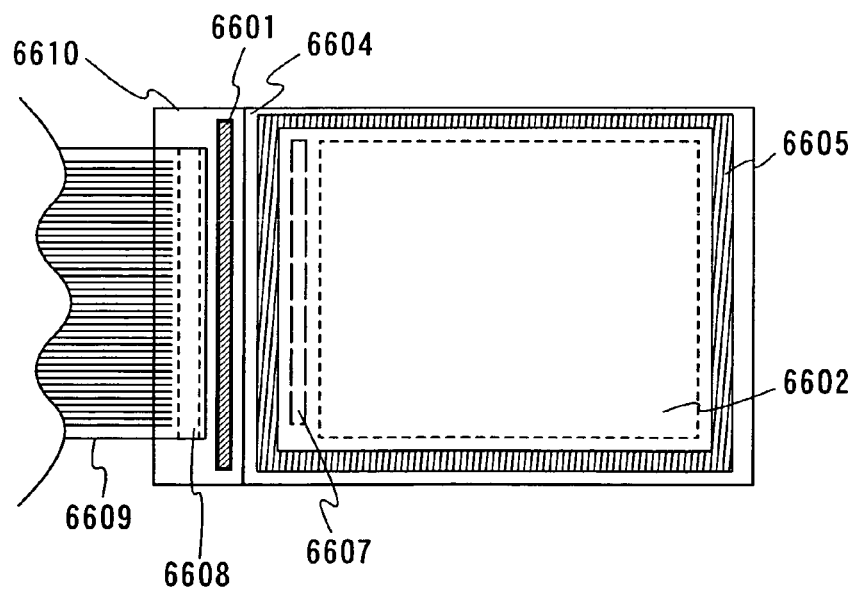

Further, the structure shown in FIG. 6A shows an example suitable for a light-emitting device having a relatively large size (e.g., a diagonal of 4.3 inches) whereas FIG. 6B shows an example employing a COG method suitable for a compact size with a narrower frame (e.g., a diagonal of 1.5 inches).

In FIG. 6B, a driver IC 6601 is mounted over a substrate 6610, and an FPC 6609 is mounted over a terminal portion 6608 disposed beyond the driver IC 6601. From an aspect of increasing productivity, a plurality of driver ICs 6601 are preferably formed over a rectangle substrate that is 300 to 1000 mm or more on one side. In other words, a plurality of circuit patterns, each of which has a driver circuit portion and an input/output terminal as one unit, is formed over the substrate and separated so that the driver ICs can be obtained separately. As for the length of the driver IC, the driver IC may be formed to have a rectangular shape having a longer side of 15 to 80 mm and a shorter side of 1 to 6 mm, considering length of one side of the pixel portion or pixel pitch, or may be formed so that the length of the longer side is a length corresponding to one side of a pixel region or a length obtained by adding one side of each driver circuit and one side of the pixel portion to each other.

For the outside dimension, the driver IC has an advantage over an IC chip in the length of the longer side. When a driver IC formed to have a longer side of 15 to 80 mm is used, the number of driver ICs to be required for mounting corresponding to the pixel portion is smaller than the case of using an IC chip, thereby improving the yield in manufacturing. In addition, when a driver IC is formed over a glass substrate, the productivity is not decreased because the driver IC is not limited to the shape of a host substrate. This is a great advantage as compared with a case of taking out IC chips from a circular silicon wafer.

In addition, a TAB method may also be employed and in that case, a plurality of tapes may be attached and driver ICs may be mounted on the tapes. As in the case of the COG method, a single driver IC may be mounted on a single tape; in this case, a metal piece or the like for fixing the driver IC may be attached together for enhancing strength.

A connection region 6607 provided between a pixel portion 6602 and the driver IC 6601 is provided so that a second electrode of a light-emitting element is in contact with a wire of a lower layer. A first electrode of the light-emitting element is electrically connected to the TFT provided in the pixel portion 6602.

In addition, a sealing substrate 6604 is fixed to the substrate 6610 with a sealant 6605 surrounding the pixel portion 6602, and a filler material surrounded by the sealant 6605.

In the case where an amorphous semiconductor film is used as an active layer of the TFT in the pixel portion, it is difficult to form the driver circuit over the same substrate, thus the structure of FIG. 6b is employed even for a large size.

Since the light-emitting device of the present invention as described above has the light-emitting element described in Embodiment Mode 2 or 3 as a light-emitting element for forming a pixel portion, high reliability and low power consumption can be achieved as well.

Embodiment Mode 6

Figure 7A:
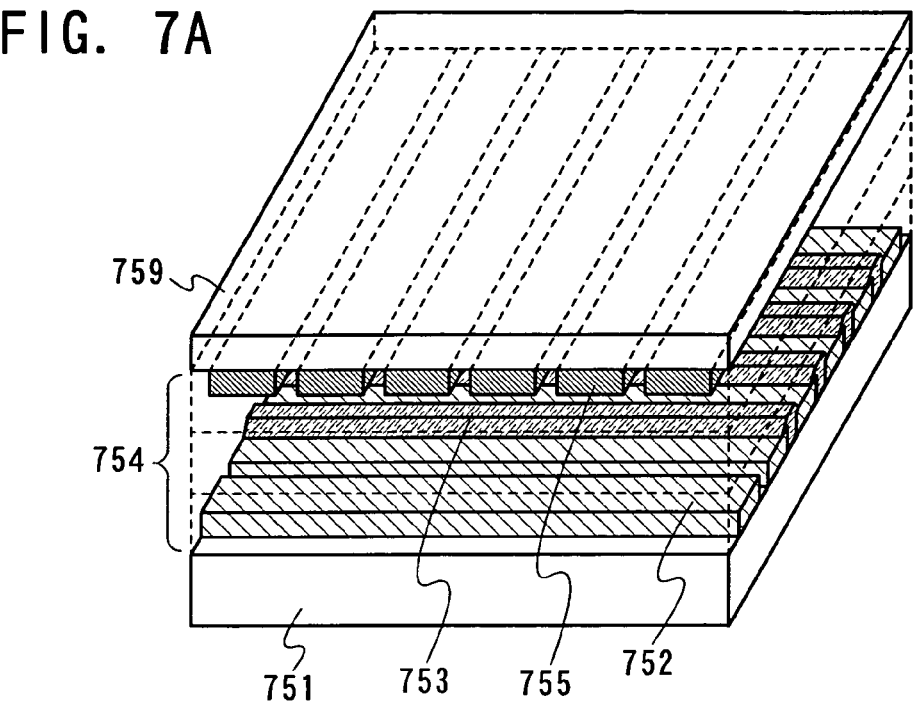
FIGS. 7A and 7B are diagrams showing an example of a light-emitting device of the present invention.
Figure 7B:
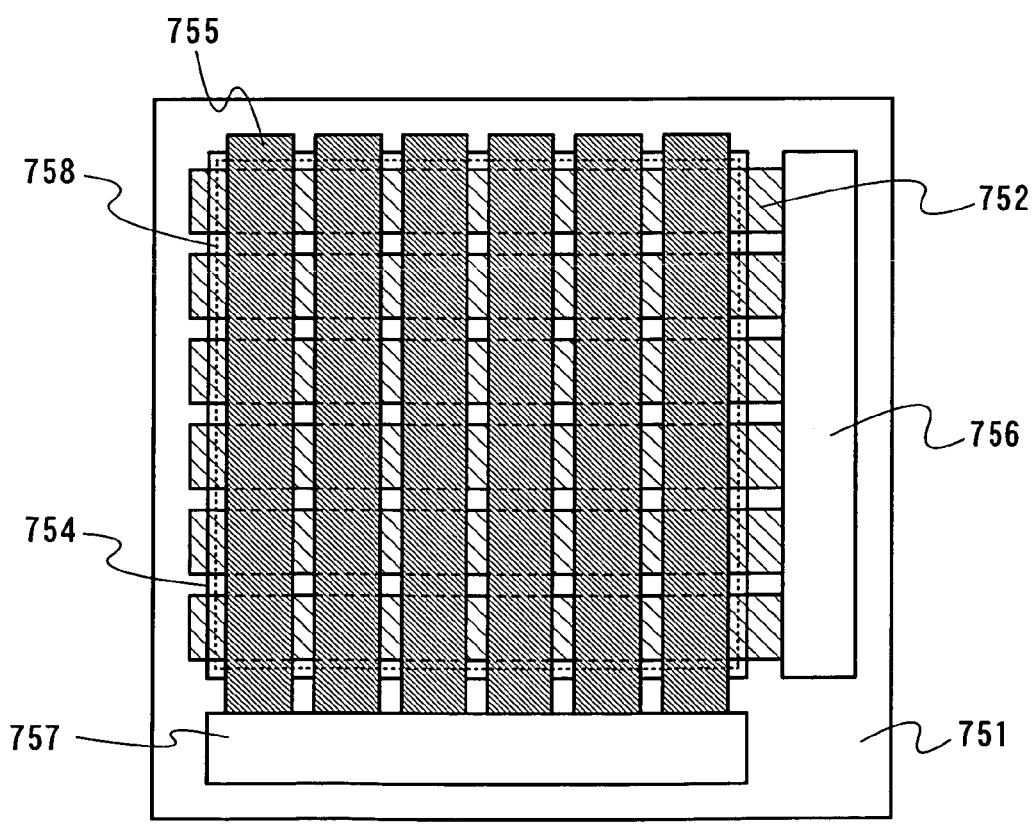

In this embodiment mode, an example of a passive light-emitting device is described with reference to FIGS. 7A and 7B. FIGS. 7A and 7B are a perspective view and a top view of a passive light-emitting device to which the present invention is applied, respectively. In particular, FIG. 7A is a perspective view of a portion surrounded by a dotted line 758 of FIG. 7B. In FIGS. 7A and 7B, the same portions are denoted by the same reference numerals. In FIG. 7A, a plurality of first electrodes 752 are provided in parallel over a substrate 751. Each of edge portions of the first electrodes 752 is covered with a partition layer 753. Note that, although a partition layer which covers the first electrode 752 on the most front side is not shown so that the positions of the first electrode 752 and the partition layer 753 that are provided over the first substrate 751 are easily recognized, an edge portion of the first electrode 752 on the most front side is actually covered with the partition layer. A plurality of second electrodes 755 are provided in parallel above the first electrode 752, so as to intersect with the plurality of the first electrodes 752. A layer 754 is provided between the first electrode 752 and the second electrode 755. The layer 754 includes a light-emitting layer containing the anthracene derivative of the present invention described in Embodiment Mode 2 or Embodiment Mode 3. In addition, the layer 754 may include a hole injecting layer, a hole transporting layer, an electron transporting layer, an electron injecting layer, or the like, in addition to the light-emitting layer. A second substrate 759 is provided over the second electrode 755.

As shown in FIG. 7B, the first electrode 752 is connected to a first driver circuit 756, and the second electrode 755 is connected to a second driver circuit 757. A portion where the first electrode 752 and the second electrode 755 are intersected with each other forms a light-emitting element of the present invention which is formed by interposing a light-emitting layer between electrodes. The light-emitting element of the present invention selected by a signal from the first driver circuit 756 and the second driver circuit 757 emits light. Light emission is extracted to outside through the first electrode 752 and/or the second electrode 755. Then, light emissions from a plurality of light-emitting elements are combined to display an image. Note that, although the partition layer 753 and the second substrate 759 are not shown in FIG. 7B so that the positions of the first electrode 752 and the second electrode 755 are easily recognized, the partition layer 753 and the second substrate 759 are actually provided as shown in FIG. 7A.

Materials for forming the first electrode 752 and the second electrode 755 are not particularly limited; however, it is preferable that the first electrode 752 and the second electrode 755 be formed using a transparent conductive material so that one of the electrodes or both of the electrodes can transmit visible light. In addition, materials for the first substrate 751 and the second substrate 759 are not particularly limited, and each of the first substrate 751 and the second substrate 759 may be formed using a material having flexibility with a resin such as plastic, in addition to a glass substrate. A material for the partition layer 753 is not particularly limited either, and the partition layer 753 may be formed using either an inorganic substance or an organic substance, or both of the inorganic substance and the organic substance. Besides, the partition layer 753 may be formed using siloxane.

Further, the layers 754 may be formed separately for each light-emitting element exhibiting a different emission color. For example, by separately providing the layers 754 for a light-emitting element emitting red light, a light-emitting element emitting green light, and a light-emitting element emitting blue light, a light-emitting device capable of multicolor display can be obtained.

As this embodiment mode, by having a light-emitting layer containing the anthracene derivative of the present invention, a passive light-emitting device with low power consumption and light emission with high luminance can be obtained.

Embodiment Mode 7

As a light-emitting device and an electronic device of the present invention, there are a video camera, a digital camera, a goggle type display (a head mount display), a navigation system, an audio reproducing device (e.g., a car stereo or an audio component system), a notebook personal computer, a game machine, a mobile information terminal (e.g., a mobile computer, a mobile phone, a mobile game machine, or an electronic book), an image reproducing device equipped with a recording medium (specifically, a device for reproducing a recording medium such as Digital Versatile Disc (DVD) and provided with a display for displaying the image), and the like. FIGS. 8A to 8D and 9 show specific examples of the electronic devices.

Figure 8A:
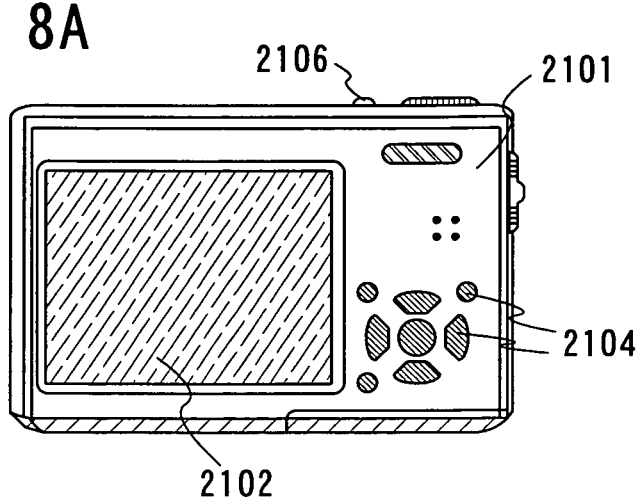
FIGS. 8A to 8D show examples of an electronic device of the present invention.

FIG. 8A shows a digital camera, which includes a main body 2101, a display portion 2102, an imaging portion, operating keys 2104, a shutter 2106, and the like. Note that FIG. 8A is a diagram from a display portion 2102 side and the imaging portion is not shown. By the present invention, a digital camera having a display portion that can display favorable images for a long time and having high reliability can be realized. In addition, low power consumption can also be achieved.

Figure 8B:
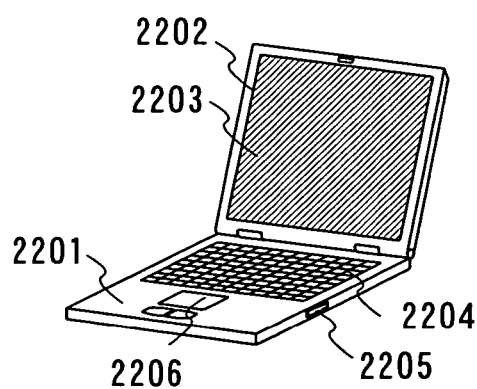

FIG. 8B shows a notebook personal computer, which includes a main body 2201, a chassis 2202, a display portion 2203, a keyboard 2204, an external connection port 2205, a pointing mouse 2206, and the like. By the present invention, a notebook personal computer having a display portion that can display favorable images for a long time and having high reliability can be achieved. In addition, low power consumption can also be achieved.

Figure 8C:
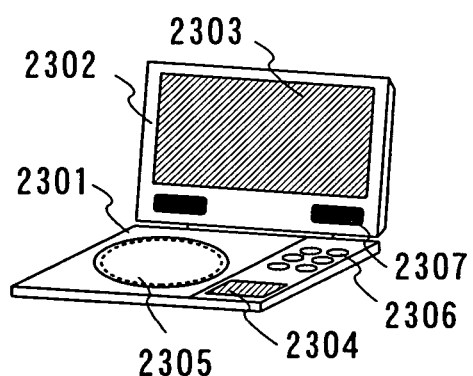

FIG. 8C shows a mobile image reproducing device equipped with a recording medium (specifically a DVD reproducing device), which includes a main body 2301, a chassis 2302, a display portion A 2303, a display portion B 2304, a recording medium (e.g., a DVD) reading portion 2305, operating keys 2306, a speaker portion 2307 and the like. The display portion A 2303 mainly displays image information and the display portion B 2304 mainly displays character information. Note that the image reproducing device equipped with a recording medium also includes a home game machine or the like. By the present invention, an image reproduction device having a display portion that can display favorable images for a long time and having high reliability can be achieved. In addition, low power consumption can also be achieved.

Figure 8D:
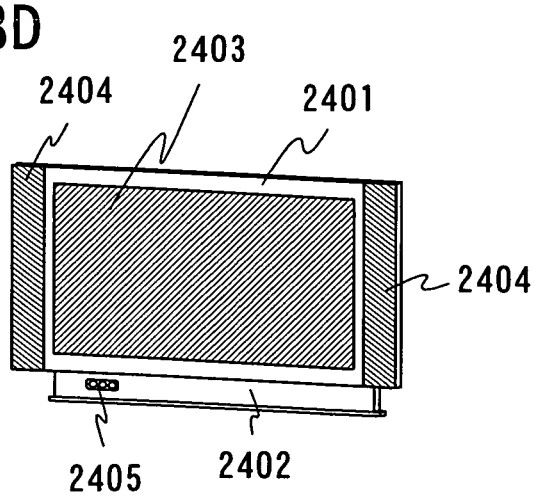

FIG. 8D shows a light-emitting device, which includes a chassis 2401, a support 2402, a display portion 2403, speakers 2404, a video input terminal 2405, and the like. The light-emitting device has a light-emitting element of the present invention in the display portion 2403. Note that as the light-emitting device, there includes all kinds of display devices for displaying information, such as devices for a computer, for receiving TV broadcasting, for displaying an advertisement and the like. By the present invention, a light-emitting device having a display portion that can display favorable images for a long time and having high reliability can be achieved. In addition, low power consumption can also be achieved.

A mobile phone shown in FIG. 9 includes a main body (a) 3001 provided with operating switches 3004, a microphone 3005 and the like, and a main body (b) 3002 provided with a display panel (a) 3008, a display panel (b) 3009, a speaker 3006 and the like, and both of the main bodies are connected with a hinge 3010 so as to open and fold the mobile phone. The display panel (a) 3008 and the display panel (b) 3009 are incorporated into a chassis 3003 of the main body (b) 3002 together with a circuit substrate 3007. Pixel portions of the display panel (a) 3008 and the display panel (b) 3009 are arranged so as to be seen from an open window formed in the chassis 3003.

The specifications of the display panel 3008 (a) and the display panel (b) 3009 such as the number of pixels can be appropriately set in accordance with the function of a mobile phone 3000. For example, the display panel (a) 3008 and the display panel (b) 3009 can be used in combination as a main display screen and a sub-display screen respectively.

In addition, by receiving a signal such as a video signal or an audio signal with an antenna 3011, the display panel (a) 3008 may serve as a display medium such as a television receiver.

By the present invention, a mobile information terminal having a display portion that can display favorable images for a long time and having high reliability can be achieved. In addition, low power consumption can also be achieved.

The mobile phone of this embodiment mode can be changed into various modes in accordance with the function or application. For example, by incorporating an imaging device into the hinge 3010, a mobile phone equipped with a camera can be provided. In addition, in the case where the operating switches 3004, the display panel (a) 3008 and the display panel (b) 3009 are incorporated into one chassis, the aforementioned operating effect can be obtained. Further, in the case where the structure of this embodiment mode is applied to an information display terminal provided with a plurality of display portions, a similar effect can be obtained.

As described above, various electronic devices, with high reliability, on which a light-emitting device having a light-emitting element of the present invention is mounted can be completed. In addition, low power consumption of the electronic devices can also be achieved.

Embodiment 1

Synthesis Example 1

Described is a synthesis method of a compound represented by a structural formula (17) as an example of the anthracene derivative of the present invention, 9-phenyl-10-[(4-[N-phenyl]-4-[3-(9-phenylcarbazolyl)])amino]anthracene (abbreviation: PCAPA).

Step 1: Synthesis method of
9-phenyl-10-(4-bromophenyl)anthracene
(abbreviation: PA)

(1) Synthesis of 9-phenylanthracene.

5.4 g (21.1 mmol) of 9-bromoarthracene, 2.6 g (21.1 mmol) of phenylboronic acid, 60 mg (0.21 mmol) of palladium acetate (abbreviation: Pd(OAc)$_2$), 10 mL (20 mmol) of potassium carbonate solution (2 mmol), 263 mg (0.84 mmol) of tris(ortho-tolyl)phosphine (abbreviation: P(o-tolyl)$_3$), and 20 mL of 1,2-dimethoxyethane (abbreviation: DME) were put in a 200 mL three neck flask, and then stirred for 9 hours at 80° C. in a nitrogen gas stream. After reaction, a precipitated solid was collected by suction filtration. Then, the solid was dissolved in toluene and then filtered through florisil®, celite, and alumina. After a filtrate was washed with water and saturated saline, it was dried with magnesium sulfate. After a mixed solution was naturally filtered and concentrated, 21.5 g of 9-phenylanthracene which was a target substance and was a light brown solid was obtained in a yield of 85% (Synthesis Scheme (b-1))

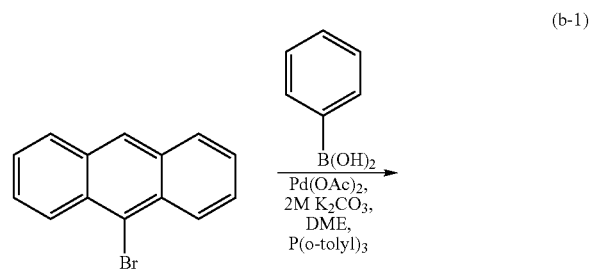

(b-1)

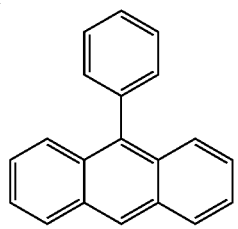

(2) Synthesis of 9-bromo-10-phenylanthracene.

6.0 g (23.7 mmol) of 9-phenylanthracene was dissolved in 80 mL of carbon tetrachloride, and then in the reaction solution thereof, a solution in which 3.80 g (21.1 mmol) of bromine dissolved in 10 mL of carbon tetrachloride was dropped with a dropping funnel. After dropping, it was stirred for 1 hour at room temperature. After reaction, a sodium thiosulfate solution was added and stirred. Then an organic layer was washed with aqueous sodium hydroxide and saturated saline, and then dried with magnesium sulfate. After a mixed solution was naturally filtered, a filtrate was concentrated and dissolved in toluene, and then filtration was carried out through florisil®, celite, and alumina. When a filtrate was concentrated and then recrystallized with a mixture of dichloromethane and hexane, 7.0 g of 9-bromo-10-phenylanthracene that was a target substance and was a light yellow solid was obtained in a yield of 89% (Synthesis Scheme (b-2)).

(b-2)

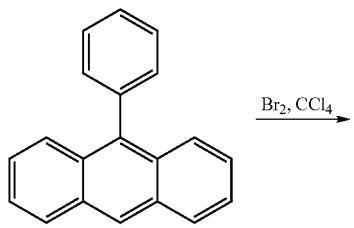

(3) Synthesis of 9-iodo-10-phenylanthracene.

3.33 g (10 mmol) of 9-bromo-10-phenylanthracene was dissolved in 80 mL of tetrahydrofuran (abbreviation: THF), and cooled to −78° C. Then, in a reaction solution thereof, 7.5 mL (12.0 mmol) of n-butyllithium (abbreviation: n-BuLi) (1.6 mol/L hexane solution) was dropped with a dropping funnel and then stirred for 1 hour. A solution in which 5 g (20.0 mmol) of iodine was dissolved in 20 mL of THF was dropped therein, and further stirred for 2 hours at −78° C. After reaction, a sodium thiosulfate solution was added and stirred. An organic layer was washed with a sodium thiosulfate solution and saturated saline, and then dried with magnesium sulfate. A mixed solution was naturally filtered, a filtrate was concentrated, and then an obtained solid was recrystallized with ethanol. Then, 3.1 g of 9-iodo-10-phenylanthracene that was a target substance and was a light yellow solid was obtained in a yield of 83% (Synthesis Scheme (b-3)).

(b-3)

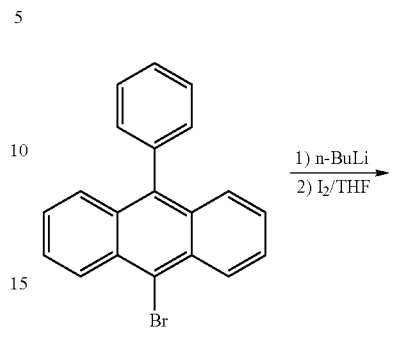

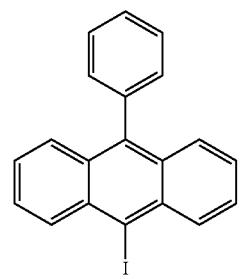

(4) Synthesis of 9-phenyl-10-(4-bromophenyl)anthracene (abbreviation: PA).

A mixture of 1.0 g (2.63 mmol) of 9-iodo-10-phenylanthracene, 542 mg (2.70 mmol) of p-bromo phenylboronic acid, 46 mg (0.03 mmol) of tetrakis(triphenylphosphine)palladium (abbreviation: Pd(PPh$_3$)$_4$ ), 3 mL (6 mmol) of potassium carbonate solution (2 mol/L), and 10 mL of toluene was stirred for 9 hours at 80° C. After reaction, toluene was added and filtration was carried out using florisil®, celite, and alumina. A filtrate was washed with water and saturated saline, and then dried with magnesium sulfate. After a mixed solution was naturally filtered and a filtrate was concentrated, an obtained solid was recrystallized with a mixture of chloroform and hexane. Then, 562 mg of 9-phenyl-10-(4-bromophenyl)anthracene (PA) that was a target substance and was a light brown solid was obtained in a yield of 45% (Synthesis Scheme (b-4)).

(b-4)

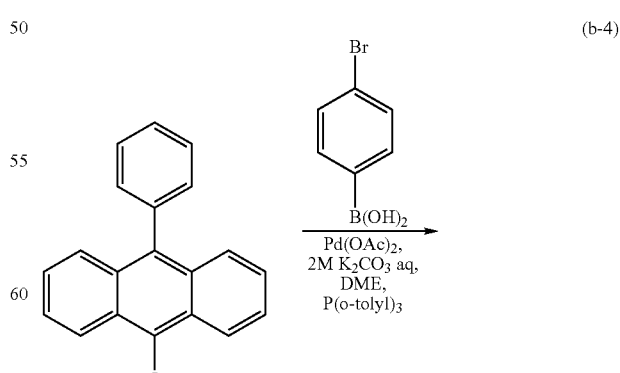

-continued

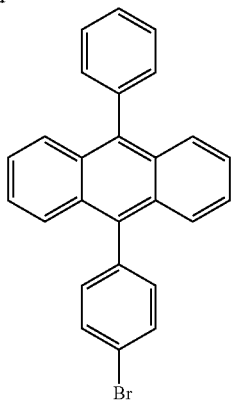

Step 2: Synthesis method of 3-(N-phenylamino)-9-phenylcarbazole (abbreviation: PCA)

(1) Synthesis of 3-bromo-9-phenylcarbazole.

24.3 g (100 mmol) of N-phenylcarbazole was dissolved in 600 mL of glacial acetic acid, and 17.8 g (100 mmol) of N-bromosuccinimide was slowly added thereto. The mixture was stirred for about 12 hours at a room temperature. This glacial acetic acid solution was dropped into 1 L of ice water while stirring it. A precipitated white solid was washed with water three times. This solid was dissolved in 150 mL of diethyl ether, and washed with a saturated sodium hydrogen carbonate solution and water. This organic layer was dried with magnesium sulfate. A mixture is filtered and a filtrate was concentrated. When an obtained residue was recrystallized with methanol, 28.4 g of 3-bromo-9-phenylcarbazole that was a target substance and was white powder was obtained in a yield of 88% (Synthesis Scheme (c-1)).

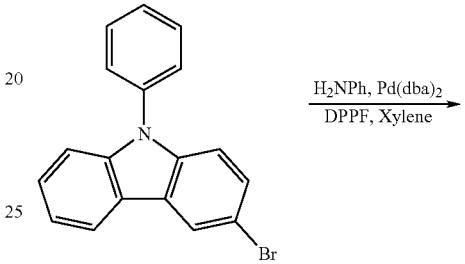

(c-1)

(2) Synthesis of 3-(N-phenylamino)-9-phenylcarbazole (abbreviation: PCA).

19 g (60 mmol) of 3-bromo-9-phenylcarbazole, 340 mg (0.6 mmol) of bis(dibenzylideneacetone)palladium(0) (abbreviation: Pd(dba)$_2$), 1.6 g (3.0 mmol) of 1,1-bis(diphenylphosphino)ferrocene (abbreviation: DPPF), and 13 g (180 mmol) of t-butoxysodium (abbreviation: t-BuONa) were put in a 500 mL three neck flask. After nitrogen was substituted for air in the flask, 110 mL of dehydrated xylene and 7.0 g (75 mmol) of aniline were added. This was stirred while heating for 7.5 hours at 90° C. After the termination of the reaction, about 500 mL of hot toluene having a temperature of 50° C. was added to a reaction solution and this reaction solution was filtered through florisil®, alumina, and celite. The filtrate was concentrated. When an obtained solid was recrystallized with a mixture of hexane and ethyl acetate, 15 g of 3-(N-phenylamino)-9-phenylcarbazole (PCA) that was a target substance and was cream-colored powder was obtained in a yield of 75% (Synthesis Scheme (c-2)).

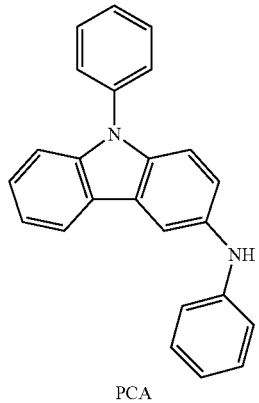

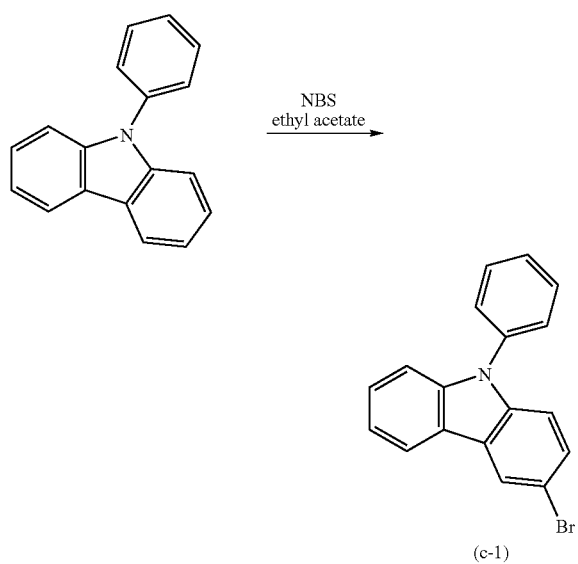

(c-2)

Figure 28A:
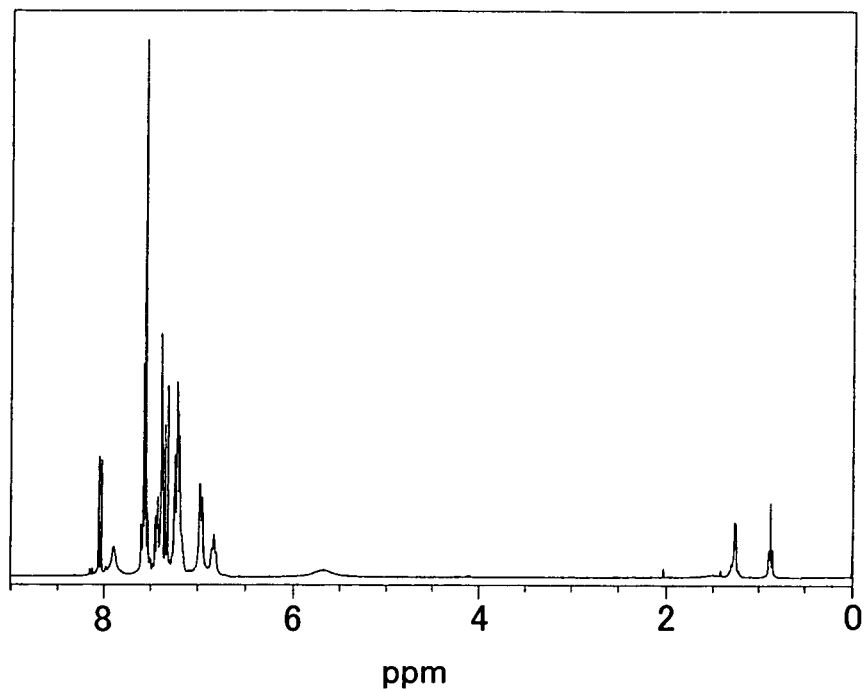
FIGS. 28A and 28B are $^1$H-NMR charts of PCA.
Figure 28B:
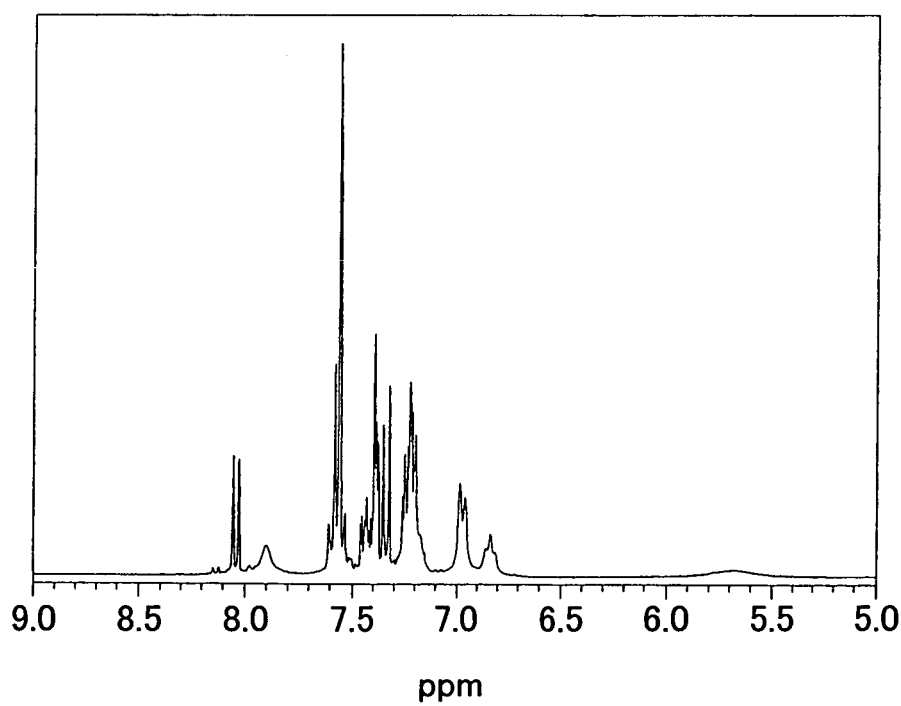

$^1$H-NMR of the obtained PCA is shown below. In addition, a $^1$H-NMR chart is shown in FIG. 28A, and an enlarged chart of a portion of 5.0 to 9.0 ppm in FIG. 28A is shown in FIG. 28B.

$^1$H-NMR (300 MHz, CDCl$_3$); δ=6.84 (t, j=6.9, 1H), 6.97 (d, j=7.8, 2H), 7.20-7.61 (m, 13H), 7.90 (s, 1H), 8.04 (d, j=7.8, 1H)

Figure 29A:
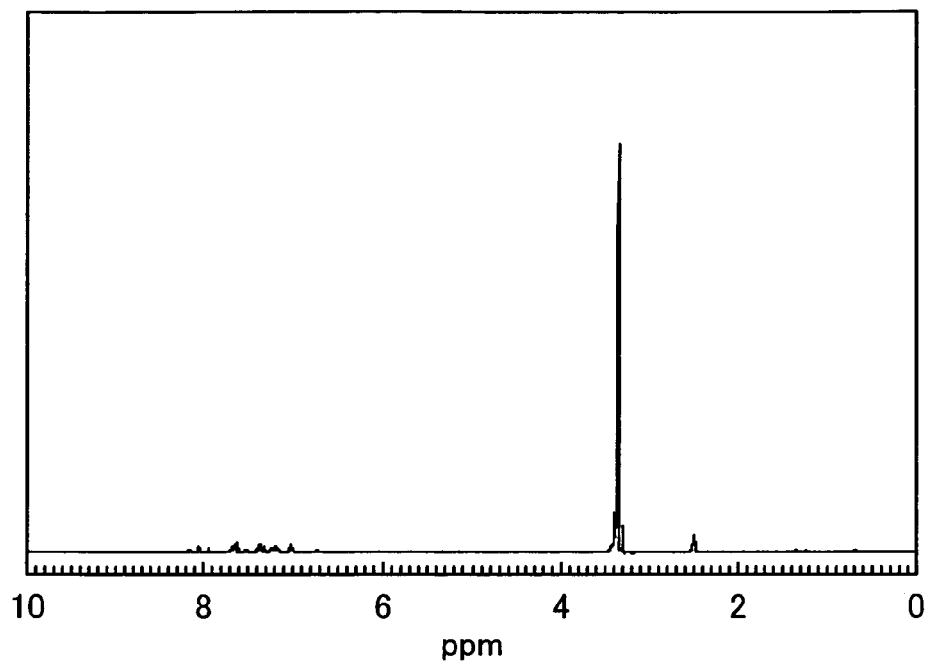
FIGS. 29A and 29B are $^1$H-NMR charts of PCA.
Figure 29B:
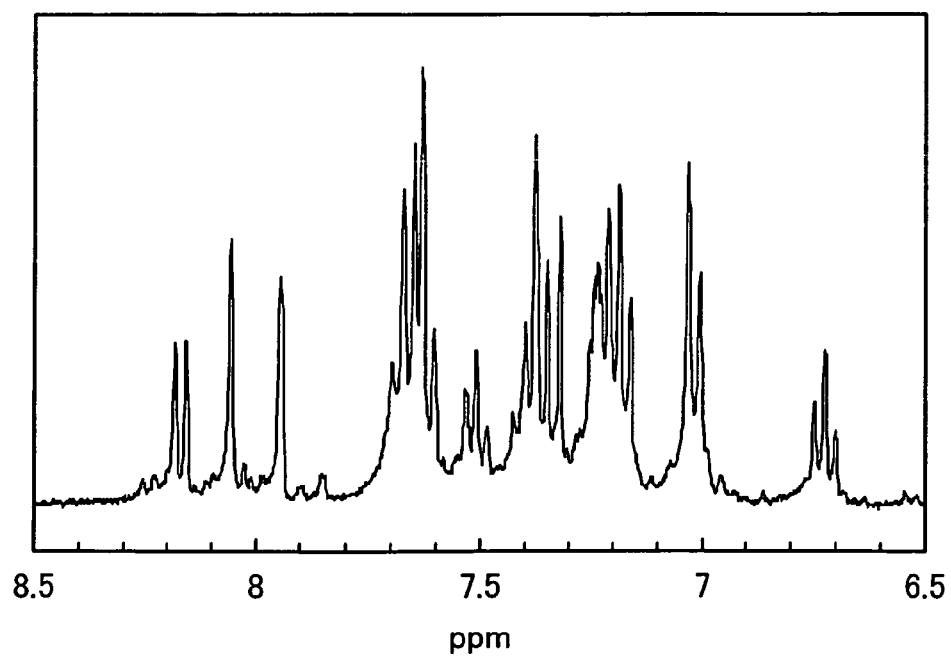

$^1$H-NMR in a case of using DMSO for a heavy solvent of the obtained PCA is shown below, and a $^1$H-NMR chart is shown in FIG. 29A, and an enlarged chart of a portion of 6.5 to 8.5 ppm in FIG. 29A is shown in FIG. 29B.

$^1$H-NMR (300 MHz, DMSO-d); δ=6.73 (t, j=7.5, 1H), 7.02 (d, j=8.1, 2H), 7.16-7.70 (m, 12H), 7.95 (s, 1H), 8.06 (s, 1H), 8.17 (d, j=7.8, 1H)

Figure 30A:
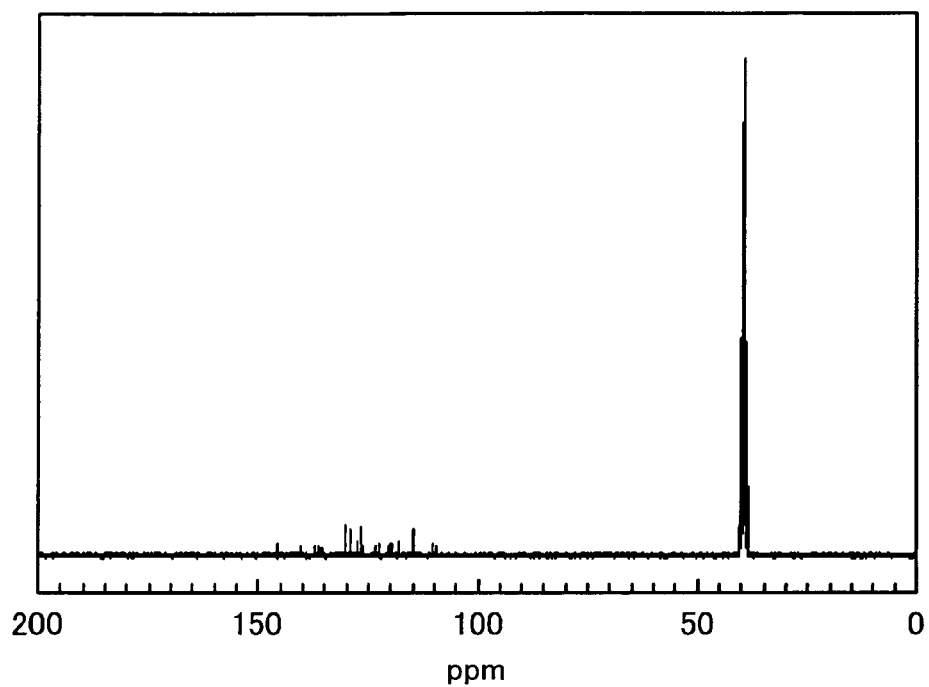
FIGS. 30A and 30B are $^{13}$C-NMR charts of PCA.
Figure 30B:
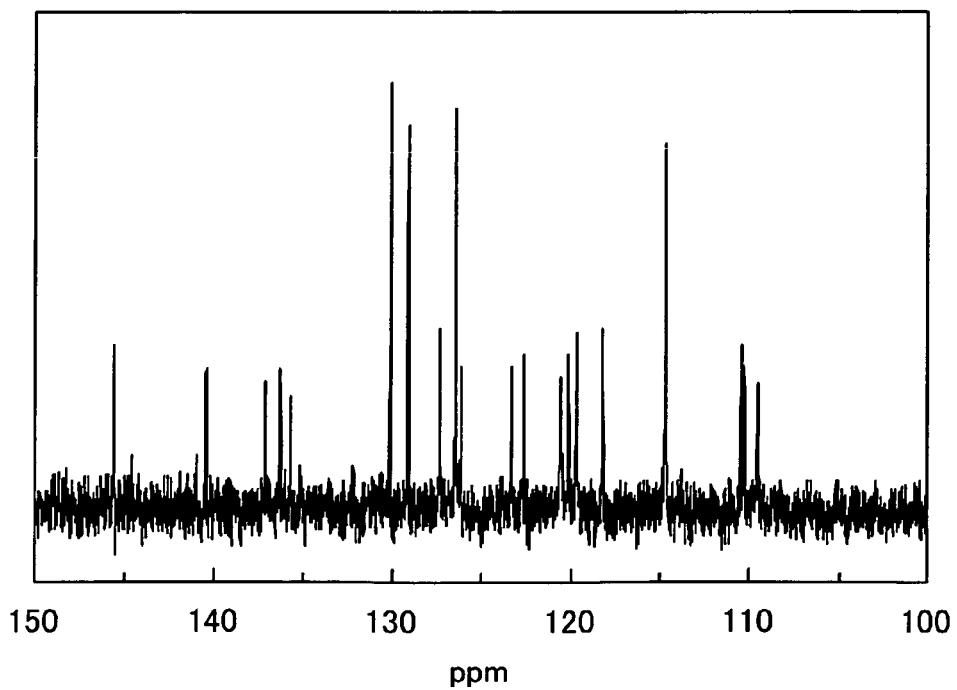

Next, $^{13}$C-NMR in a case of using DMSO for a heavy solvent of the obtained PCA is shown below, and a $^{13}$C-NMR chart is shown in FIG. 30A and an enlarged chart of a portion of 100 to 150 ppm in FIG. 30A is shown in FIG. 30B.

$^{13}$C-NMR (75.5 MHz, DMSO-d); δ=109.55, 110.30, 110.49, 114.71, 118.22, 119.70, 120.14, 120.61, 122.58, 123.35, 126.18, 126.48, 127.37, 129.15, 130.14, 135.71, 136.27, 137.11, 140.41, 145.61

Step 3: Synthesis method of 9-phenyl-10-[(4-[N-phenyl]-4-[3-(9-phenylcarbazolyl)])amino]anthracene (PCAPA)

409 mg (1.0 mmol) of 9-phenyl-10-(4-bromophenyl)anthracene (PA), 339 mg (1.0 mmol) of 3-(N-phenylamino)-9-phenylcarbazole (PCA), 6 mg (0.01 mmol) of Pd(dba)$_2$, 500 mg (5.2 mol) of t-butoxysodium (abbreviation: t-BuONa), 0.1 mL of tri(t-butyl)phosphine (10 wt % hexane solution) (abbreviation: P(tBu)$_3$), and 10 mL of toluene were put in a 100 mL three neck flask and stirred for 4 hours at 80° C. After reaction, a solution was washed with water, an aqueous layer was extracted with toluene, and it was washed together with the organic layer using saturated saline, and then dried with magnesium sulfate. An oily product obtained by filtering a mixture naturally and concentrating a filtrate was purified with silica gel column chromatography (hexane:toluene=7:3), and recrystallized using a mixture of dichloromethane and hexane to obtain 534 mg of a yellow powder-like solid that was a target substance in a yield of 81% (Synthesis Scheme (d-1)). When this compound was measured by a nuclear magnetic resonance (NMR) method, it was confirmed that the compound was 9-phenyl-10-[(4-[N-phenyl]-4-[3-(9-phenylcarbazolyl)])amino]anthracene (PCAPA).

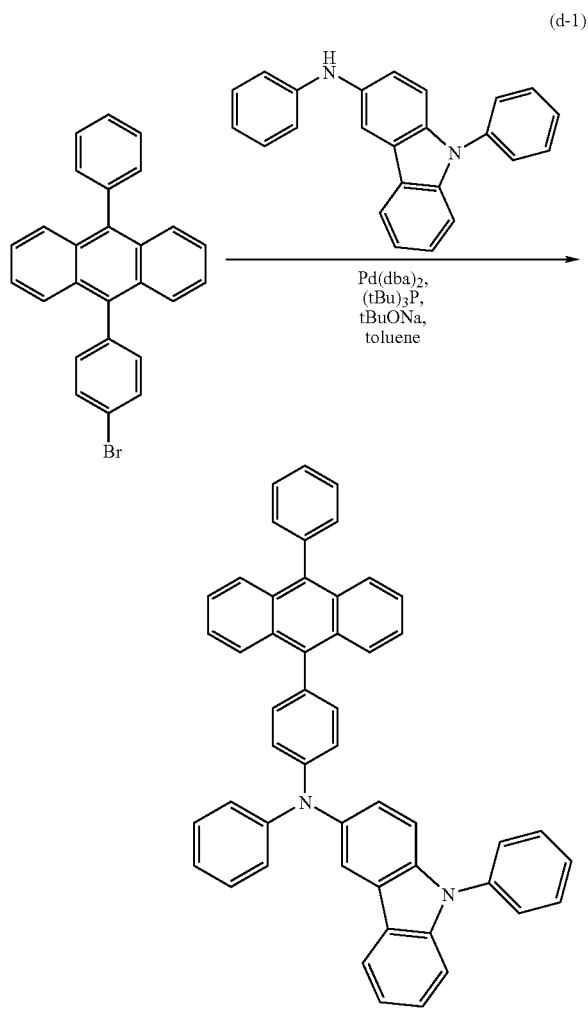

(d-1)

Figure 10A:
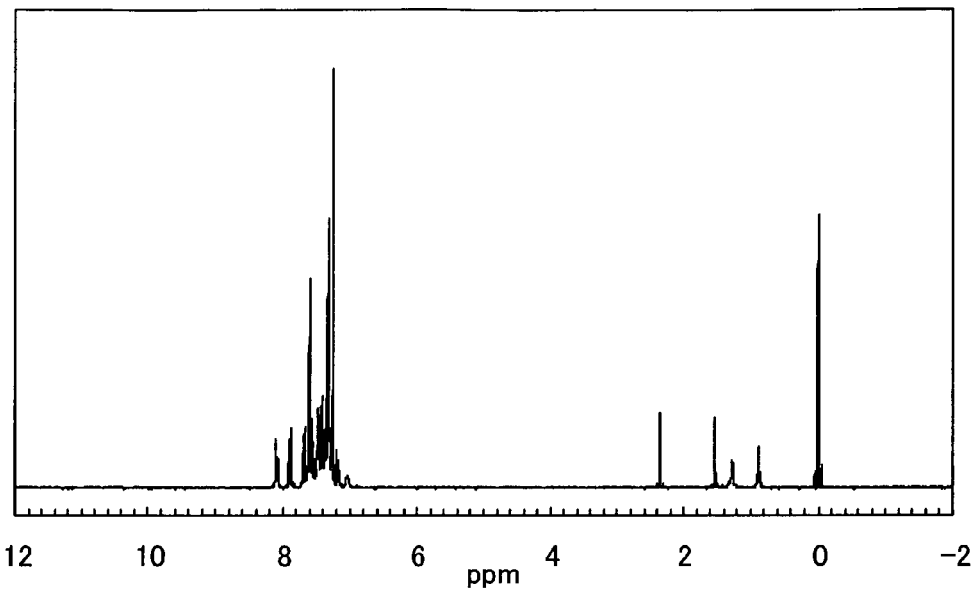
FIGS. 10A and 10B are $^1$H-NMR charts of PCAPA.
Figure 10B:
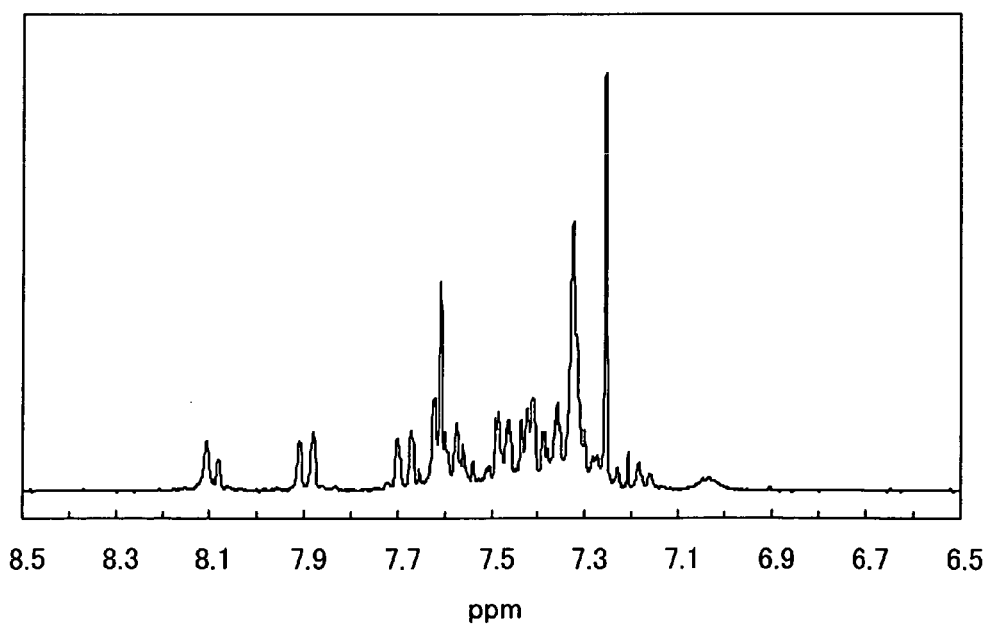

$^1$H-NMR of this compound is shown below. In addition, $^1$H-NMR charts are shown in FIGS. 10A and 10B. Note that FIG. 10B is a chart showing an enlarged part in the range of 6.5 to 8.5 ppm of FIG. 10A.

$^1$H-NMR (300 MHz, CDCl$_3$); δ=8.11-8.08 (m, 2H), 7.91-7.88 (m, 2H), 7.70-7.67 (m, 2H), 7.63-7.30 (m, 28H)

Figure 11:
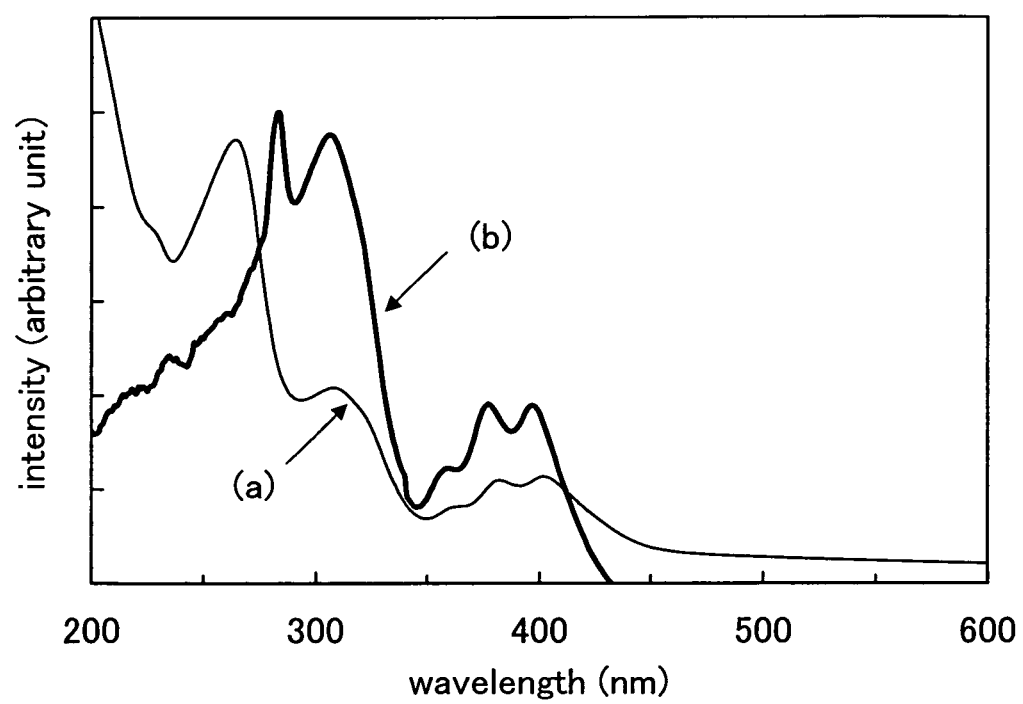
FIG. 11 shows absorption spectra of PCAPA.
Figure 12:
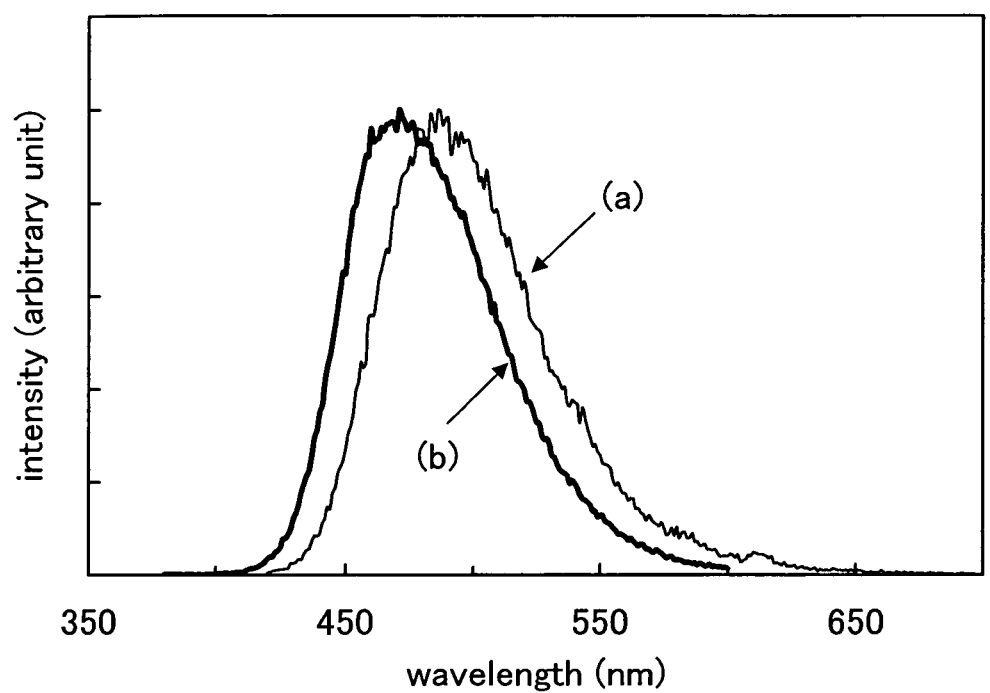
FIG. 12 shows emission spectra of PCAPA.

The absorption spectra of the PCAPA are shown in FIG. 11. The ultraviolet-visible spectrophotometer (V-550, manufactured by JASCO Corporation) was used for the measurement. In FIG. 11, the horizontal axis represents a wavelength (nm) and the vertical axis represents intensity (arbitrary unit). Further, in FIG. 11, a line (a) indicates the absorption spectrum in a state where the PCAPA is in a single film whereas a line (b) indicates the absorption spectrum in a state where the PCAPA is dissolved in a toluene solution. The light emission spectra of the PCAPA are shown in FIG. 12. In FIG. 12, the horizontal axis represents a wavelength (nm) and the vertical axis represents intensity (arbitrary unit). A line (a) indicates the light emission spectrum (an excited wavelength: 402 nm) in a state where the PCAPA is in a single film and a line (b) indicates the light emission spectrum (an excited wavelength: 370 nm) in a state where the PCAPA is dissolved in a toluene solution. It is found from FIG. 12 that light emission from the PCAPA has a peak at 486 nm in the single film state and has a peak at 471 nm in the dissolved state in the toluene solution. Moreover, the light emission was recognized as blue light. Thus, it is found that the PCAPA is suitable as a light-emitting substance exhibiting blue light particularly.

When a film was formed with the obtained PCAPA by an evaporation method and the ionization potential of the PCAPA in the thin film state was measured by using a photoelectron spectrometer (AC-2, manufactured by RIKEN KEIKI CO., LTD.), the ionization potential was 5.29 eV This result showed that the HOMO level was −5.29 eV. The absorption spectrum of the PCAPA in the thin film state was measured by using an ultraviolet-visible spectrophotometer (V-550, manufactured by JASCO Corporation), and a wavelength of an absorption edge at a longer wavelength side of the absorption spectrum (the line (a) in FIG. 11) was set to be an energy gap (2.74 eV). Under these conditions, when the LUMO level was measured, it was −2.55 eV.

Further, when a decomposition temperature $T_d$ of the obtained PCAPA was measured by a thermo-gravimetric/differential thermal analyzer (TG/DTA 320, manufactured by Seiko Instruments Inc.), the $T_d$ was 402° C. or more. Therefore, it was understood that the PCAPA had a favorable heat resistant property.

In addition, an oxidation reduction reaction characteristic of the PCAPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF) was used as a solvent. Tetra-n-butylammonium perchlorate (n-Bu$_4$NClO$_4$), which was a supporting electrolyte, was dissolved in the solvent such that the concentration of the tetra-n-butylammonium perchlorate became 100 mmol/L. Moreover, the PCAPA, which was a target to be measured, was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode.

The oxidation reaction characteristic was measured as follows. The scan in which the electric potential of the work electrode with respect to the reference electrode was changed from −0.27 V to 0.70 V, and then changed from 0.70 V to −0.27 V, was referred to as one cycle. The oxidation reaction characteristic for 100 cycles was measured. Note that the scanning speed of the CV measurement was set to be 0.1 V/s.

The reduction reaction characteristic was measured as follows. The scan in which the electric potential of the work electrode with respect to the reference electrode was changed from −0.36 V to −2.60 V, and then changed from −2.60 V to −0.36 V, was referred to as one cycle. The reduction reaction characteristic for 100 cycles was measured. Note that, the scanning speed of the CV measurement was set to be 0.1 V/s.

Figure 13A:
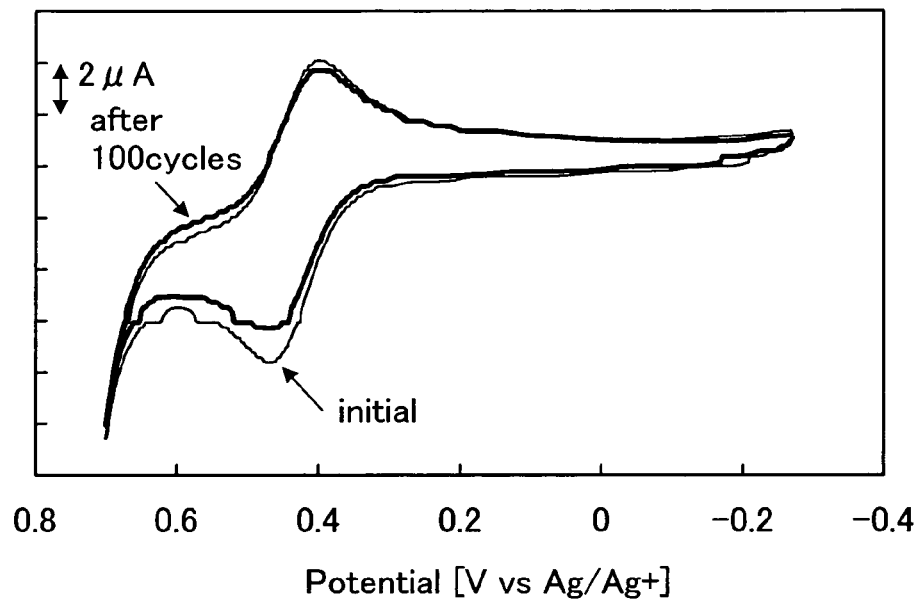
FIGS. 13A and 13B are diagrams showing a test result by cyclic voltammetry (CV) on PCAPA.
Figure 13B:
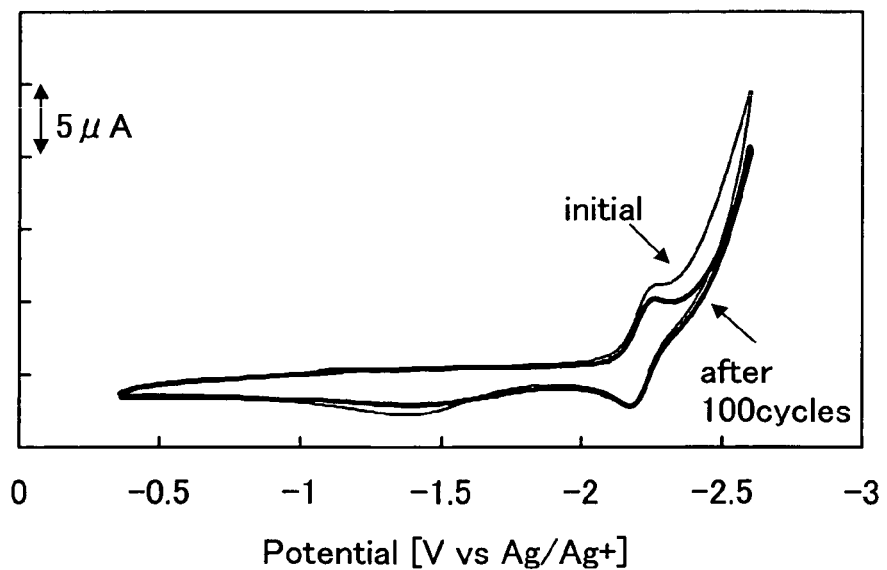

Results of measuring the oxidation reaction characteristic of the PCAPA are shown in FIG. 13A. Moreover, results of measuring the reduction reaction characteristic of the PCAPA are shown in FIG. 13B. In FIGS. 13A and 13B, the horizontal axis represents an electric potential (V) of the work electrode with respect to the reference electrode, while the vertical axis represents the amount of current flowing between the work electrode and the auxiliary electrode ($1\times10^{-5}$ A).

It was found from FIG. 13A that an oxidation potential was 0.47 V (vs. Ag/Ag$^+$ electrode). It was found from FIG. 13B that a reduction potential was −2.26 V (vs. Ag/Ag$^+$ electrode). Although the scan was repeated for 100 cycles, a peak of a CV curve was clearly observed in each of the oxidation reaction and the reduction reaction. Thus, it is found that the anthracene derivative of the present invention is a substance showing favorable reversibility with respect to an oxidation reduction reaction, and particularly shows excellent reversibility with respect to an oxidation reaction.

Note that when the PCAPA is synthesized by a method described in this embodiment mode, the PCAPA can be synthesized in high yield.

Embodiment 2

Synthesis Example 2

Described is a synthesis method of a compound represented by a structural formula (20) as an example of the anthracene derivative of the present invention, 9-phenyl-10-{4'-[N-phenyl-N-(9-phenylcarbazole-3-yl)amino]biphenyl-4-yl}anthracene (abbreviation: PCAPBA).

Step 1: Synthesis method of
9-[4-(4-bromophenyl)phenyl]-10-phenylanthracene
(abbreviation: PBA)

(1) Synthesis of 4-(4-bromophenyl)phenylboronic acid.

10.0 g (0.032 mol) of 4,4'-dibromobiphenyl was put in a 500 mL three neck flask, and nitrogen was substituted for air in the flask, and then 200 mL of tetrahydrofuran was added and stirred at −80° C. 20 mL (0.032 mol) of n-butyllithium (1.60 M hexane solution) was dropped into a reaction solution, and stirred for 1 hour at −80° C., and 40 mL (0.060 mol) of trimethyl borate was added and stirred for 1 hour while returning to room temperature. After 200 mL (1.0 mol/L) of hydrochloric acid water was added to the reaction solution, and stirred for about 12 hours, an organic layer was washed with a saturated sodium hydrogen carbonate solution and saturated saline, and then dried with magnesium sulfate. After the reaction solution was naturally filtered, a solid which was obtained by concentrating a filtrate, was recrystallized with a mixture of ethyl acetate and hexane. 3.7 g of 4-(4-bromophenyl)phenylboronic acid that was a target substance and was a white solid was obtained in a yield of 41% (Synthesis Scheme (e-1)).

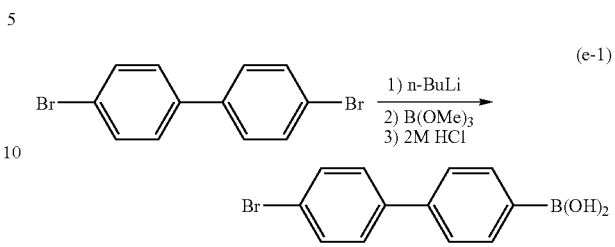

(2) Synthesis of 9-[4-(4-bromophenyl)phenyl]-10-phenylanthracene (abbreviation: PBA)

1.0 g (2.63 mmol) of 9-iodo-10-phenylanthracene, 542 mg (2.70 mmol) of 4-(4-bromophenyl)phenylboronic acid, 46 mg (0.03 mmol) of tetrakis(triphenylphosphine)palladium, 3 mL (6 mmol) of potassium carbonate solution (2.0 mol/L), and 10 mL of toluene were stirred for 9 hours at 80° C. After reaction, toluene was added, and it was filtered through florisil®, celite, and alumina. The filtrate was washed with water and saturated saline, and then dried with magnesium sulfate. After natural filtering, the filtrate was concentrated, and when recrystallization was performed with a mixture of chloroform and hexane, 562 mg of 9-[4-(4-bromophenyl)phenyl]-10-phenylanthracene (PBA) that was a target substance and was a light brown solid was obtained in a yield of 45% (Synthesis Scheme (e-2)).

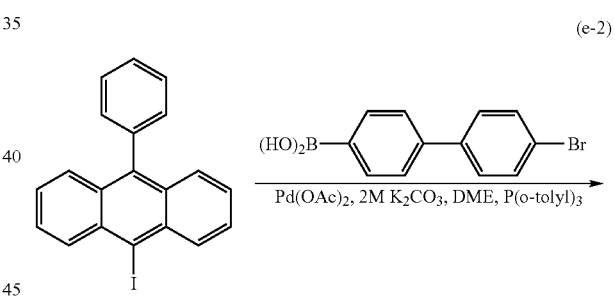

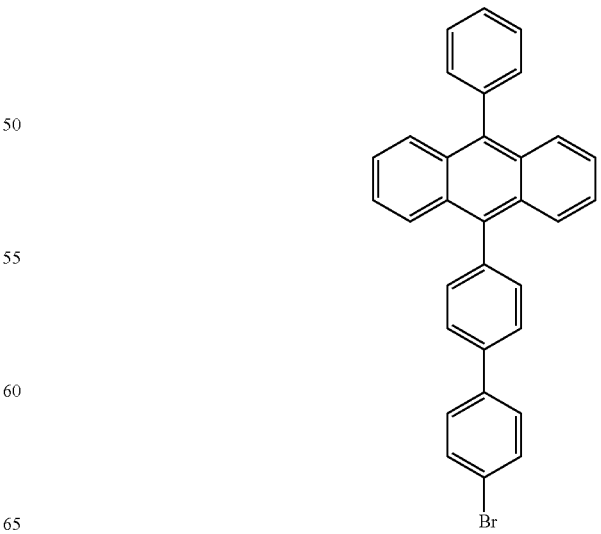

Step 3: Synthesis method of 9-phenyl-10-{4'-[N-phenyl-N-(9-phenylcarbazole-3-yl)amino]biphenyl-4-yl}anthracene (abbreviation: PCAPBA)

15 mL of dehydration xylene was added to a mixture including 730 mg (1.5 mmol) of 9-[4-(4-bromophenyl)phenyl]-10-phenylanthracene (PBA), 500 mg (1.5 mmol) of 3-(N-phenylamino)-9-phenylcarbazole (PCA), 58 mg (0.1 mmol) of bis(dibenzylideneacetone)palladium(0), 1 mL (0.5 mmol) of tri(t-butyl)phosphine (10 wt % hexane solution), and 400 mg (4.0 mmol) of t-butoxysodium (t-BuONa). This was stirred while heating at 110° C. under a nitrogen atmosphere for 5.5 hours. After the termination of the reaction, this suspension was added with about 200 mL of toluene, and this was filtered through florisil® and celite. An obtained filtrate was concentrated and recrystallized, so that 9-phenyl-10-{4'-[N-phenyl-N-(9-phenylcarbazole-3-yl)amino]biphenyl-4-yl}anthracene (abbreviation: PCAPBA) that was a target substance and was a light yellow powder solid was obtained. In addition, a mixture which was obtained by concentrating the recrystallized filtrate was purified with silica gel column chromatography (toluene:hexane=1:1). When the obtained compound was recrystallized with hexane, a light yellow powder solid of PCAPBA that was a target substance was obtained. 700 mg of PCAPBA in combined with the first-obtained target substance was obtained in a yield of 63% (Synthesis Scheme (f-i)). This compound was measured by a nuclear magnetic resonance (NMR) method and confirmed to be 9-phenyl-10-{4'-[N-phenyl-N-(9-phenylcarbazole-3-yl)amino]biphenyl-4-yl}anthracene

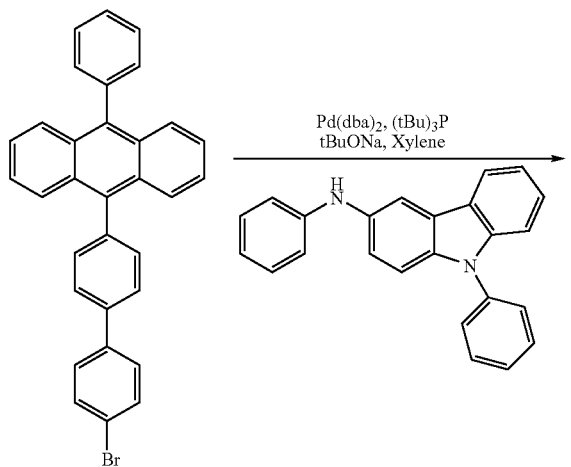

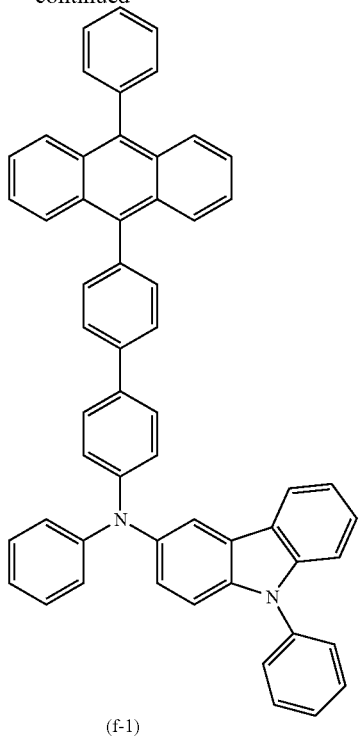

(f-1)

Figure 14A:
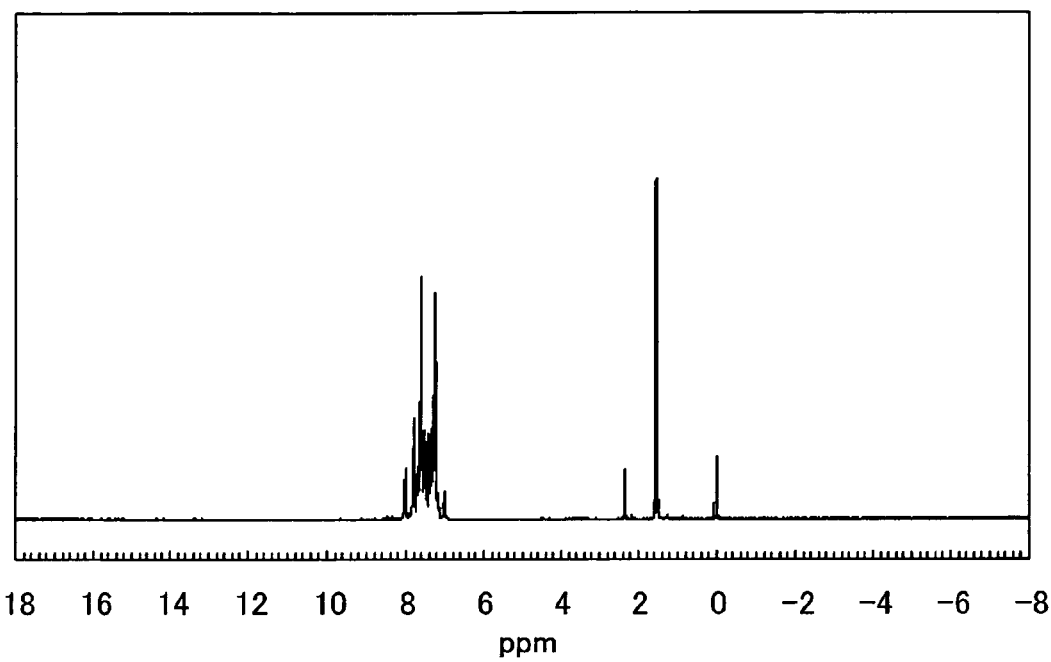
FIGS. 14A and 14B are $^1$H-NMR charts of PCAPBA.
Figure 14B:
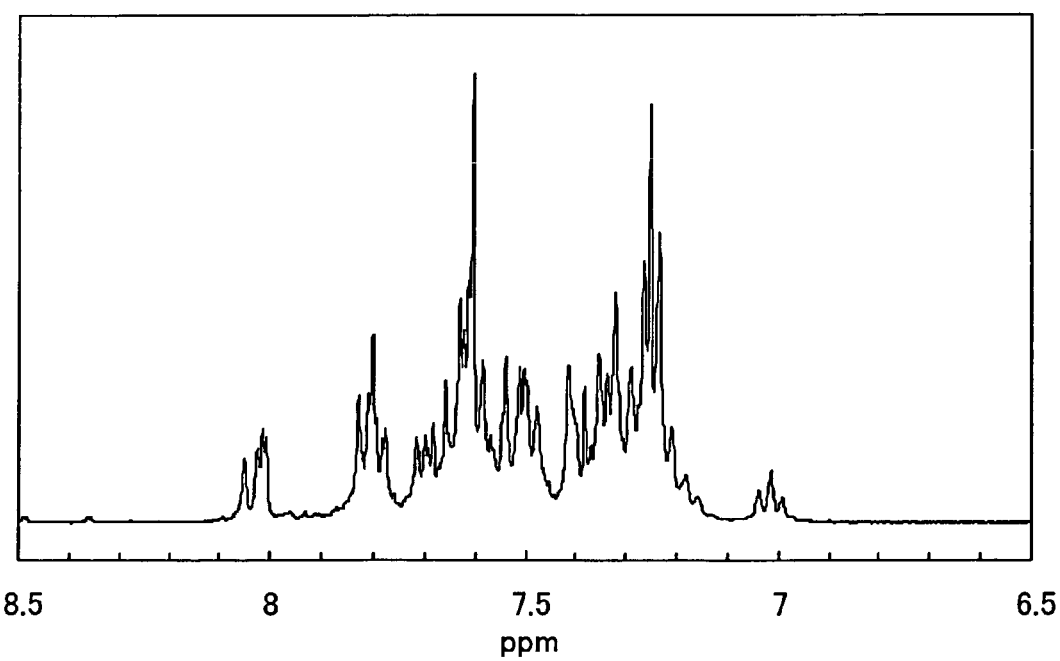

The $^1$H-NMR of this compound is shown below. In addition, $^1$H-NMR charts are also shown in FIGS. 14A and 14B. Note that FIG. 14B is a chart showing an enlarged part in the range of 6.5 to 8.5 ppm of FIG. 14A.

$^1$H-NMR (300 MHz, CDCl$_3$); δ=8.51-8.00 (m, 2H), 7.83-7.78 (m, 4H), 7.72-7.48 (m, 16H), 7.41-7.23 (m, 16H)

Figure 15:
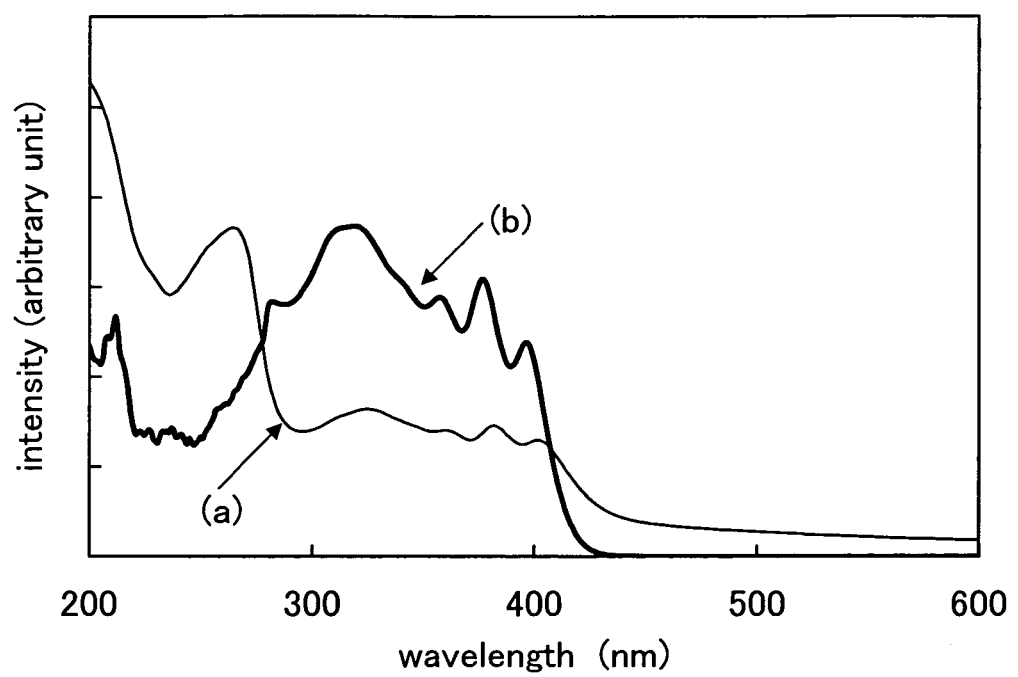
FIG. 15 shows absorption spectra of PCAPBA.
Figure 16:
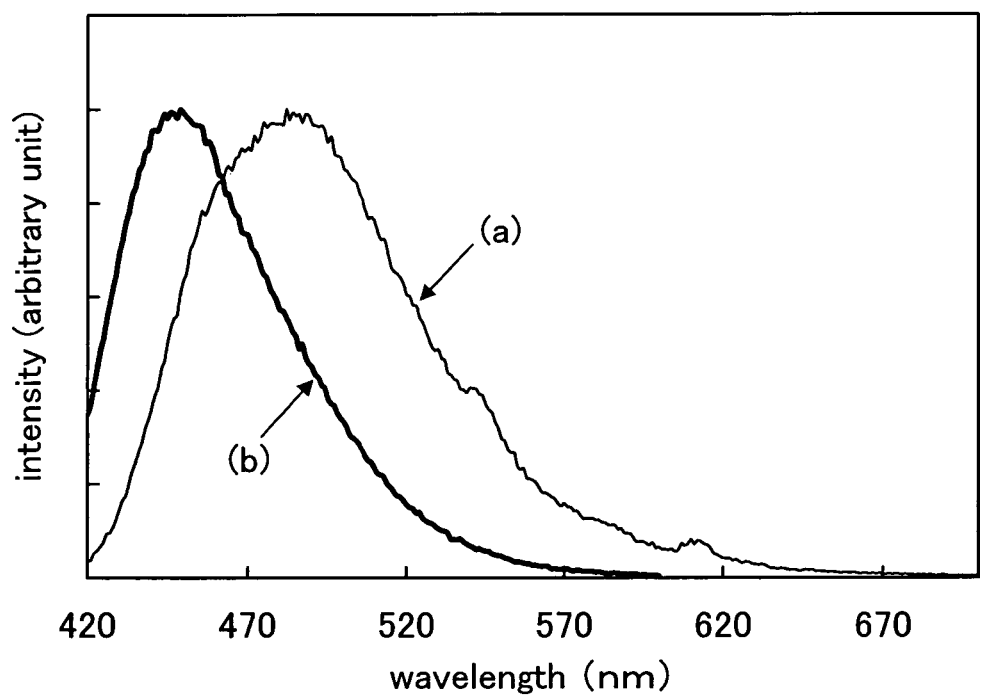
FIG. 16 shows emission spectra of PCAPBA.

The absorption spectra of the PCAPBA are shown in FIG. 15. The ultraviolet-visible spectrophotometer (V-550, manufactured by JASCO Corporation) was used for the measurement. In FIG. 15, the horizontal axis represents a wavelength (nm) and the vertical axis represents intensity (arbitrary unit). Further, in FIG. 15, a line (a) indicates the absorption spectrum in a state where the PCAPBA is in a single film whereas a line (b) indicates the absorption spectrum in a state where the PCAPBA is dissolved in a toluene solution. The light emission spectra of the PCAPBA are shown in FIG. 16. In FIG. 16, the horizontal axis represents a wavelength (nm) and the vertical axis represents intensity (arbitrary unit). In FIG. 16, a line (a) indicates the light emission spectrum (an excited wavelength: 402 nm) in a state where the PCAPBA is in a single film and a line (b) indicates the light emission spectrum (an excited wavelength: 395 nm) in a state where the PCAPBA is dissolved in a toluene solution. It is found from FIG. 16 that light emission from the PCAPBA has a peak at 482 nm in the single film state and has a peak at 448 nm in the dissolved state in the toluene solution. Moreover, the light emission was recognized as blue light. Thus, it is found that the PCAPBA is suitable as a light-emitting substance exhibiting blue light.

When a film was formed with the obtained PCAPBA by an evaporation method and the ionization potential of the PCAPBA in the thin film state was measured by using a photoelectron spectrometer (AC-2, manufactured by RIKEN KEIKI CO., LTD.), the ionization potential was 5.29 eV. This result showed that the HOMO level was −5.29 eV. The absorption spectrum of the PCAPBA in the thin film state was measured by using a ultraviolet-visible spectrophotometer (V-550, manufactured by JASCO Corporation), and a wavelength of an absorption edge at a longer wavelength side of the absorption spectrum ((a) in FIG. 15) was set to be an energy gap (2.82 eV). Under these conditions, when the LUMO level was measured, it was −2.47 eV.

Further, when a decomposition temperature $T_d$ of the obtained PCAPBA was measured by a thermo-gravimetric/differential thermal analyzer (TG/DTA 320, manufactured by Seiko Instruments Inc.), the $T_d$ was 430° C. or more. Therefore, it was understood that the PCAPBA has a favorable heat resistant property.

Note that when the PCAPBA is synthesized by a method described in this embodiment mode, the PCAPBA can be synthesized in high yield.

Embodiment 3

Synthesis Example 3

Described is a synthesis method of a compound represented by a structural formula (30) as an example of the anthracene derivative of the present invention, 9-{4-[N-(1-naphthyl)-N-(9-phenylcarbazole-3-yl)amino]phenyl}-10-phenylanthracene (abbreviation: PCNPA).

Step 1: Synthesis method of 3-[N-(1-naphthyl)amino]-9-phenylcarbazole (abbreviation: PCN)

Under nitrogen, 12 mL of dehydration xylene was added to a mixture of 3.7 g (10 mmol) of 3-iodo-9-phenylcarbazole, 1.6 g (5 mmol) of 1-aminonaphthalen, 60 mg (0.1 mmol) of bis(dibenzylideneacetone)palladium(0), 200 μL (0.5 mmol) of tri(t-butyl)phosphine (49 wt % hexane solution), 3 g (30 mmol) of t-butoxysodium (abbreviation: t-BuONa). This was stirred while heating at 90° C. under a nitrogen atmosphere for 7 hours. After the termination of the reaction, this suspension was added with about 200 mL of hot toluene and was filtered through florisil®, alumina, and celite. The obtained filtrate was concentrated and this residue was separated by silica gel column chromatography (toluene:hexane=1:1). When an obtained solid was recrystallized with a mixture of ethyl acetate and hexane, 1.5 g of 3-[N-(1-naphthyl)amino]-9-phenylcarbazole (PCN) that was a target substance and was cream-colored powder was obtained in a yield of 79% (Synthesis Scheme (g-1)).

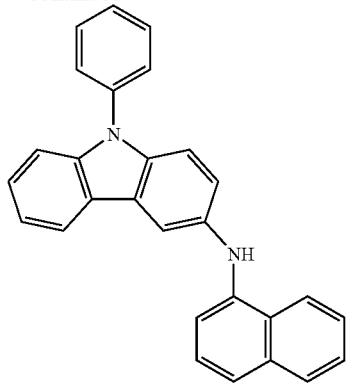

Figure 31A:
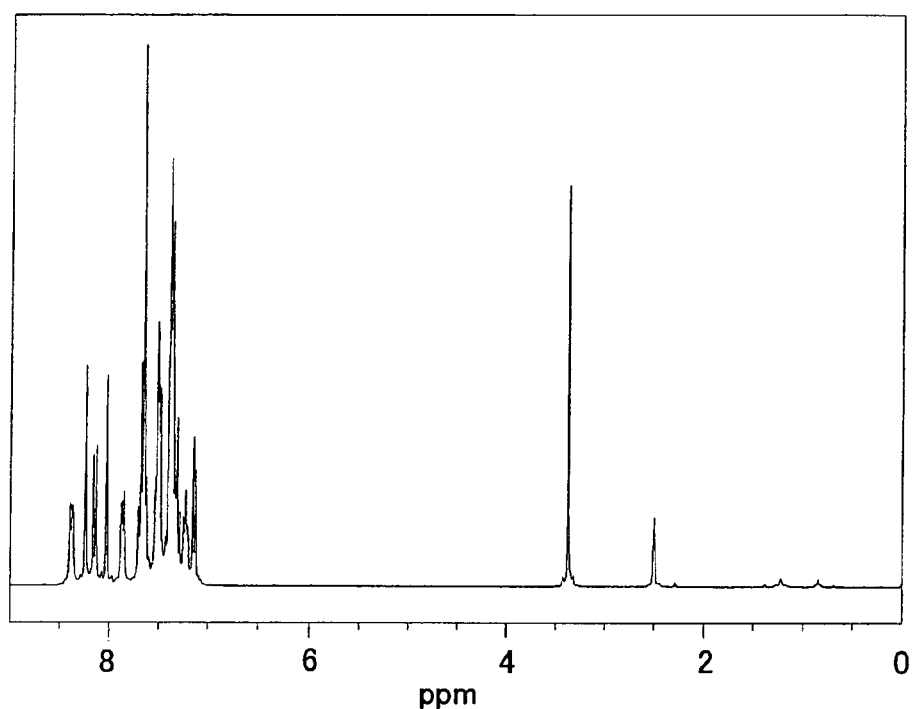
FIGS. 31A and 31B are $^1$H-NMR charts of PCN.
Figure 31B:
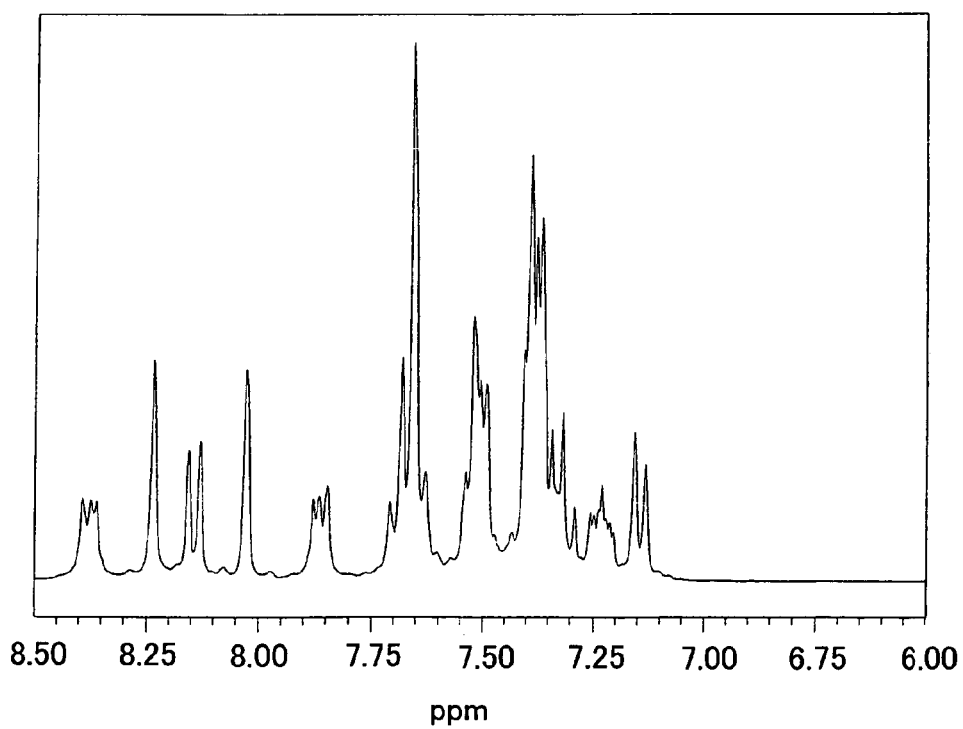

The $^1$H-NMR of the obtained PCN is shown below, and a $^1$H-NMR chart is shown in FIG. 31A, and an enlarged chart of a portion of 6.5 to 8.5 ppm in FIG. 31A is shown in FIG. 31B.

$^1$H-NMR (300 MHz, DMSO-d); δ=7.13-7.71 (m, 15H), 7.85-7.88 (m, 1H), 8.03 (s, 1H), 8.15 (d, J=7.8, 1H), 8.24 (s, 1H), 8.36-8.39 (m, 1H)

Step 2: Synthesis method of 9-{4-[N-(1-naphthyl)-N-(9-phenylcarbazole-3-yl)amino]phenyl}-10-phenylanthracene (abbreviation: PCNPA)

2.0 g (5.0 mmol) of 9-phenyl-10-(4-bromophenyl)anthracene (PA), 1.9 g (5.0 mmol) of 3-[N-(1-naphthyl)amino]-9-phenylcarbazole (PCN), 2.1 g (20 mmol) of t-butoxysodium (abbreviation: t-BuONa) were put in a 100 mL three neck flask, and nitrogen was substituted for air in the flask, and then 40 mL of toluene and 0.1 mL of tri(t-butyl)phosphine (10 wt % hexane solution) (abbreviation: P(tBu)$_3$) were added, and the 100 mL three neck flask was depressurized and degassed. After degassing, 30 mg (0.05 mmol) of bis(dibenzylideneacetone)palladium(0) was added, and stirred for 3 hours at 80° C. After reaction, a reaction solution was washed with water and saturated saline in this order, and then an organic layer was dried with magnesium sulfate. After natural filtration, a solid which was obtained by concentrating the filtrate was purified with silica gel column chromatography (hexane:toluene=7:3). When a target substance was recrystallized with dichloromethane hexane, 1.5 g of a yellow-solid target substance was obtained in a yield of 43% (Synthesis Scheme (g-2)). This compound was measured by a nuclear magnetic resonance (NMR) method and confirmed to be was PCNPA.

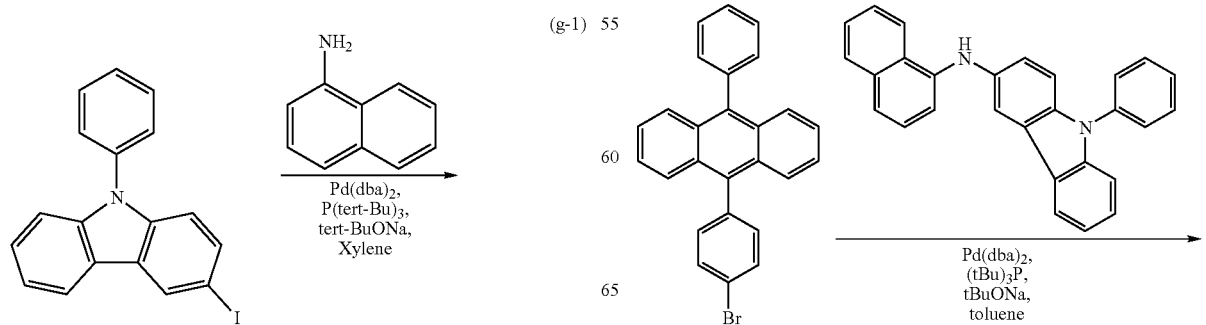

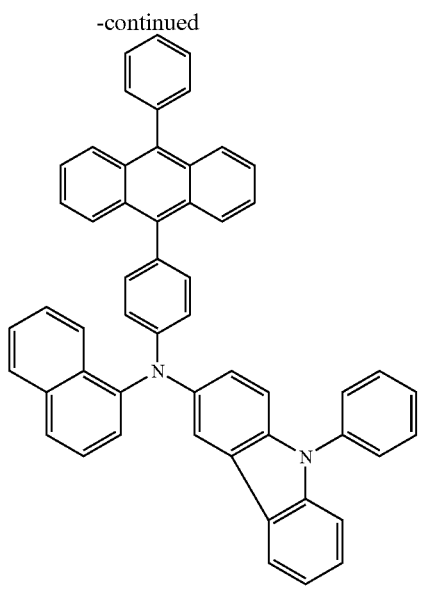

Figure 32A:
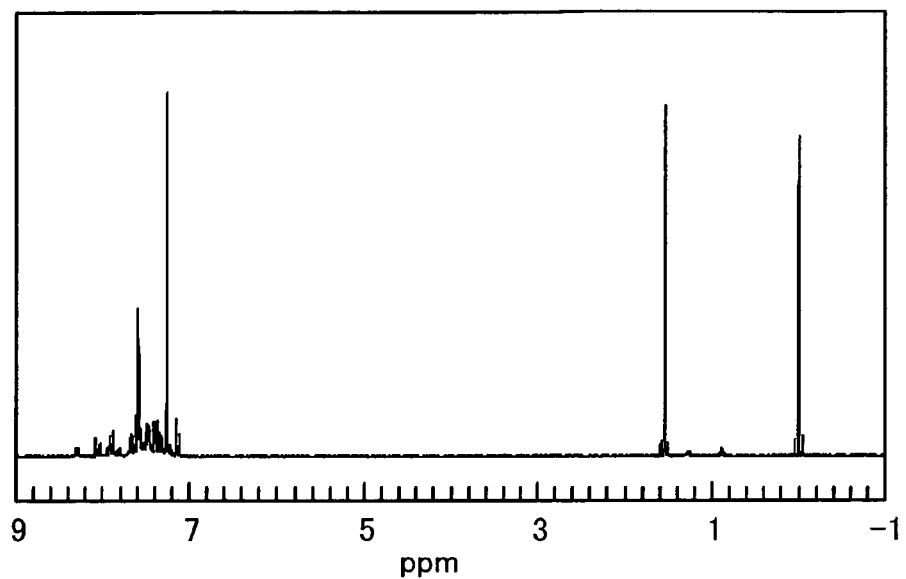
FIGS. 32A and 32B are $^1$H-NMR charts of PCNPA.
Figure 32B:
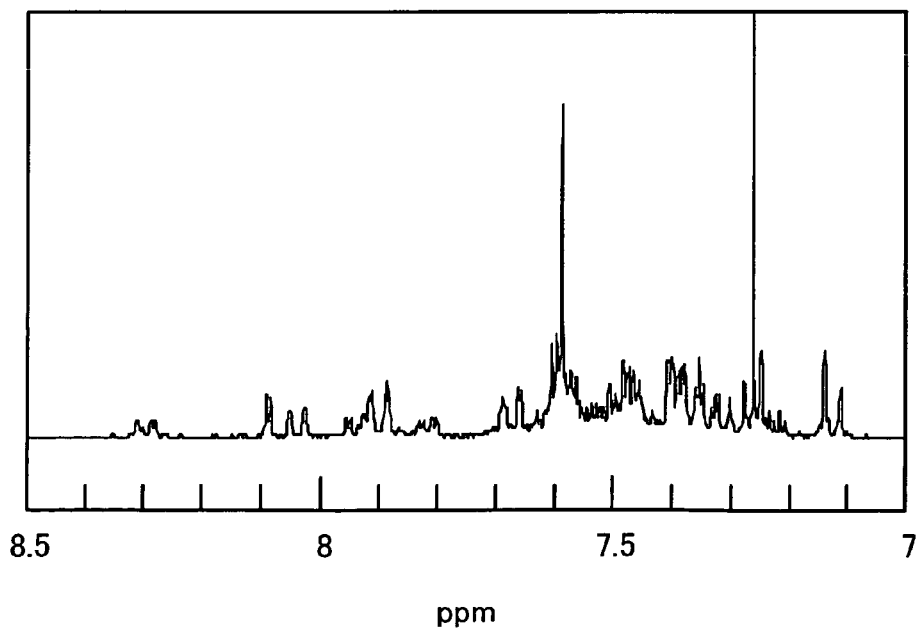

The $^1$H-NMR of the obtained PCNPA is shown below. In addition, a $^1$H-NMR chart is shown in FIG. 32A. Note that FIG. 32B is a chart showing an enlarged part in the range of 7.0 to 8.5 ppm of FIG. 32A.

$^1$H-NMR (300 MHz, CDCl$_3$-d); δ=7.13 (d, J=8.7Hz, 2H), 7.21-7.23 (m, 1H) 7.30-7.69 (m, 26H), 7.80-7.83 (m, 1H), 7.87-7.96 (m, 3H), 8.04 (d, J=7.5Hz, 1H), 8.09 (d, J=2.4Hz, 1H), 8.28-8.31 (m, 1H)

Figure 33:
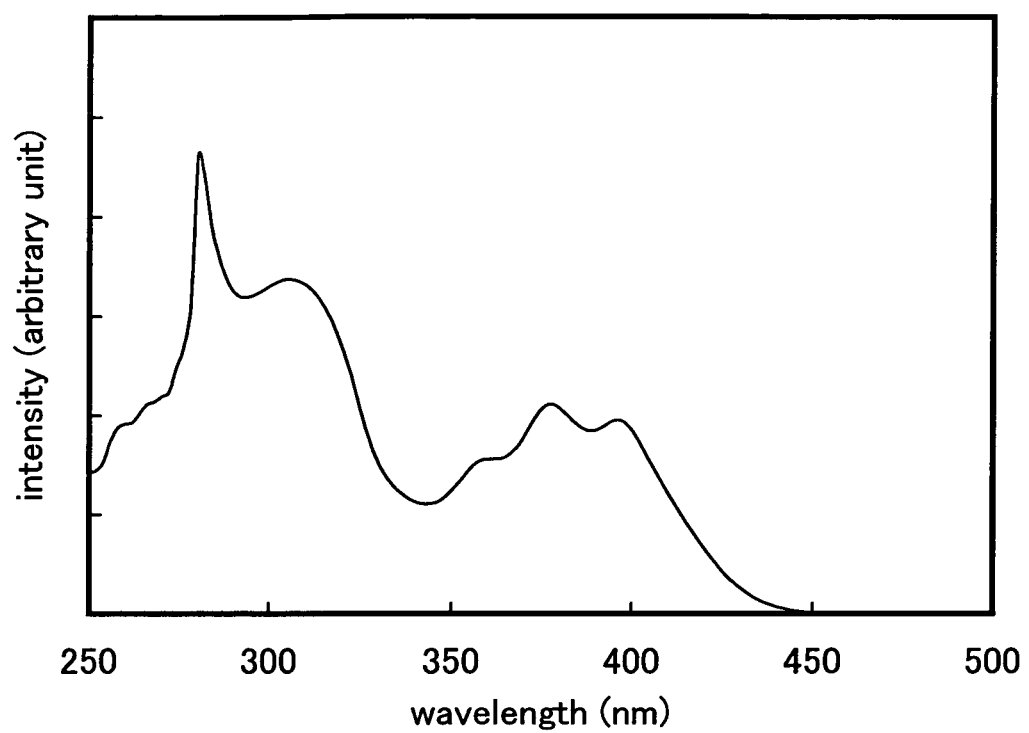
FIG. 33 shows an absorption spectrum of PCNPA.
Figure 34:
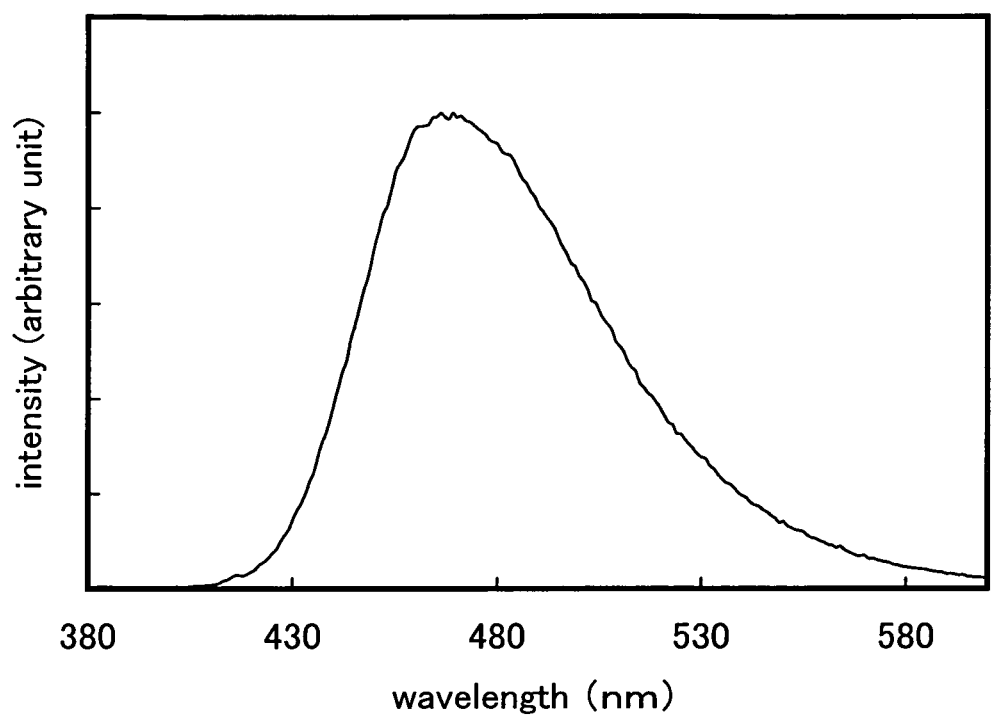
FIG. 34 shows an emission spectrum of PCNPA.

The absorption spectrum of the PCNPA is shown in FIG. 33. The ultraviolet-visible spectrophotometer (V-550, manufactured by JASCO Corporation) was used for the measurement. In FIG. 33, the horizontal axis represents a wavelength (nm) and the vertical axis represents intensity (arbitrary unit). Further, in FIG. 33, a line indicates the absorption spectrum in a state where the PCNPA is dissolved in a toluene solution. The light emission spectrum of the PCNPA is shown in FIG. 34. In FIG. 34, the horizontal axis represents a wavelength (nm) and the vertical axis represents intensity (arbitrary unit). In FIG. 34, a line indicates the light emission spectrum (an excited wavelength: 370 nm) in a state where the PCNPA is dissolved in a toluene solution. It is found from FIG. 34 that light emission from the PCNPA has a peak at 470 nm in the toluene solution. Moreover, the light emission was recognized as blue light. Thus, it is found that the PCNPA is suitable as a light-emitting substance exhibiting blue light.

Embodiment 4

In this embodiment, an example of the light-emitting element in which the anthracene derivative of the present invention is used and a manufacturing method thereof is described. In addition, a property of a manufactured light-emitting element is described.

First, a first electrode was formed over a glass substrate by depositing indium tin oxide added with silicon oxide (ITSO) with a thickness of 110 nm by a sputtering method and etching the indium tin oxide so as to have a square shape having a size of 2 mm×2 mm.

Next, a glass substrate was fixed to a holder provided inside a vacuum evaporation apparatus so that the surface over which the first electrode was formed faced downward.

Next, the vacuum apparatus was evacuated to decrease pressure so as to be $10^{-4}$ Pa, and thereafter a hole injecting layer was formed over the first electrode by performing co-evaporation so that a weight ratio of 4,4'-bis{N-[4-(N,N-di-m-tolylamino)phenyl]-N-phenylamino}biphenyl (abbreviation: DNTPD) to molybdenum trioxide was 4:2 with a thickness of 50 nm.

Next, a hole transporting layer was formed over the hole injecting layer using 4,4'-bis[N-(1-naphthyl)-N-phenylamino]biphenyl (abbreviation: NPB) to have a thickness of 10 nm by an evaporation method.

Next, a light-emitting layer was formed over the hole transporting layer by forming a layer containing 9-[4-(N-carbazolyl)]phenyl-10-phenylanthracene (abbreviation: CzPA) and PCAPA which was an anthracene derivative of the present invention to have a thickness of 40 nm by a co-evaporation method.

Then, an electron transporting layer was formed over the light-emitting layer using tris(8-quinolinolato) aluminum (abbreviation: Alq3) to have a thickness of 20 nm by an evaporation method.

Next, an electron injecting layer was formed over the electron transporting layer using lithium fluoride (LiF) to have a thickness of 1 nm by an evaporation method.

Next, a second electrode was formed over the electron injecting layer using aluminum (Al) to have a thickness of 200 nm by an evaporation method.

As for the light-emitting element manufactured as described above, current flows when voltage is applied so that potential of the first electrode is higher than that of the second electrode, excitation energy is generated when electrons and holes are recombined in the light-emitting layer, and light is emitted when excited PCAPA returns to a ground state.

Note that, a light-emitting element 1 was formed so that a mass ratio of CzPA to PCAPA contained in the light-emitting layer is CzPA: PCAPA=1:0.025; a light-emitting element 2 was formed so that CzPA: PCAPA=1:0.05, and a light-emitting element 3 was formed so that CzPA: PCAPA=1:0.1.

Note that as for the light-emitting element manufactured as described above, current flows when voltage is applied so that potential of the first electrode is higher than that of the second electrode. Then, excitation energy is generated when holes injected from the first electrode side and electrons injected from the second electrode side are recombined in a third layer functioning as a light-emitting layer, and light is emitted when excited PCAPA returns to a ground state.

After the light-emitting elements 1 to 3 were sealed so as not to be exposed to the air under a nitrogen atmosphere in a glove box, operation characteristics of the light-emitting elements were measured.

Figure 17:
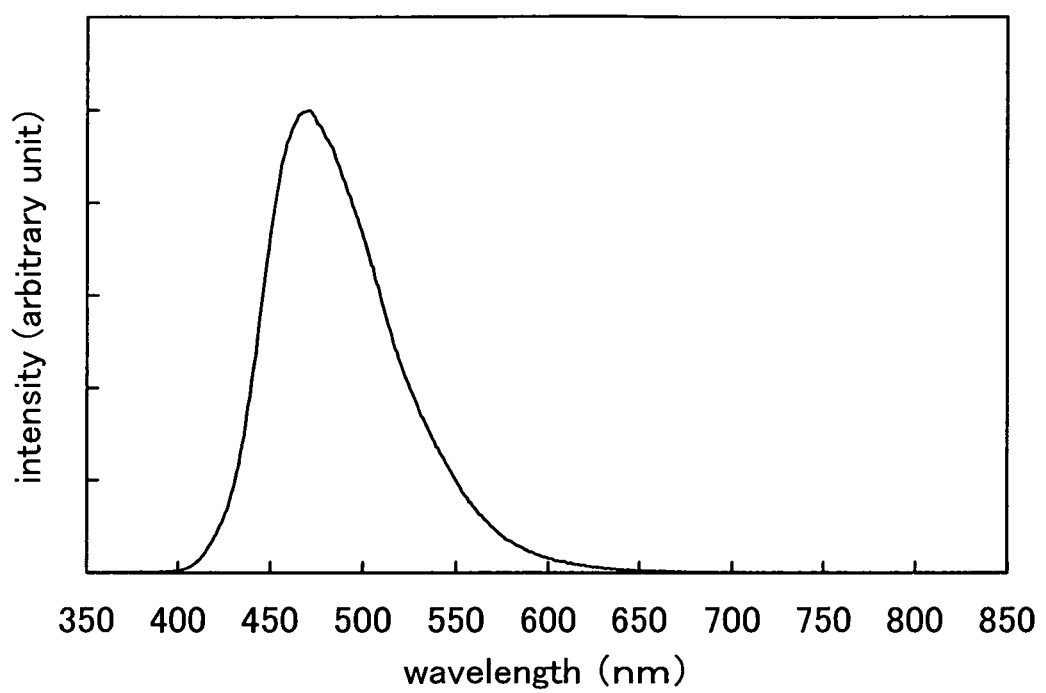
FIG. 17 shows an emission spectrum of a light-emitting element 1.
Figure 18:
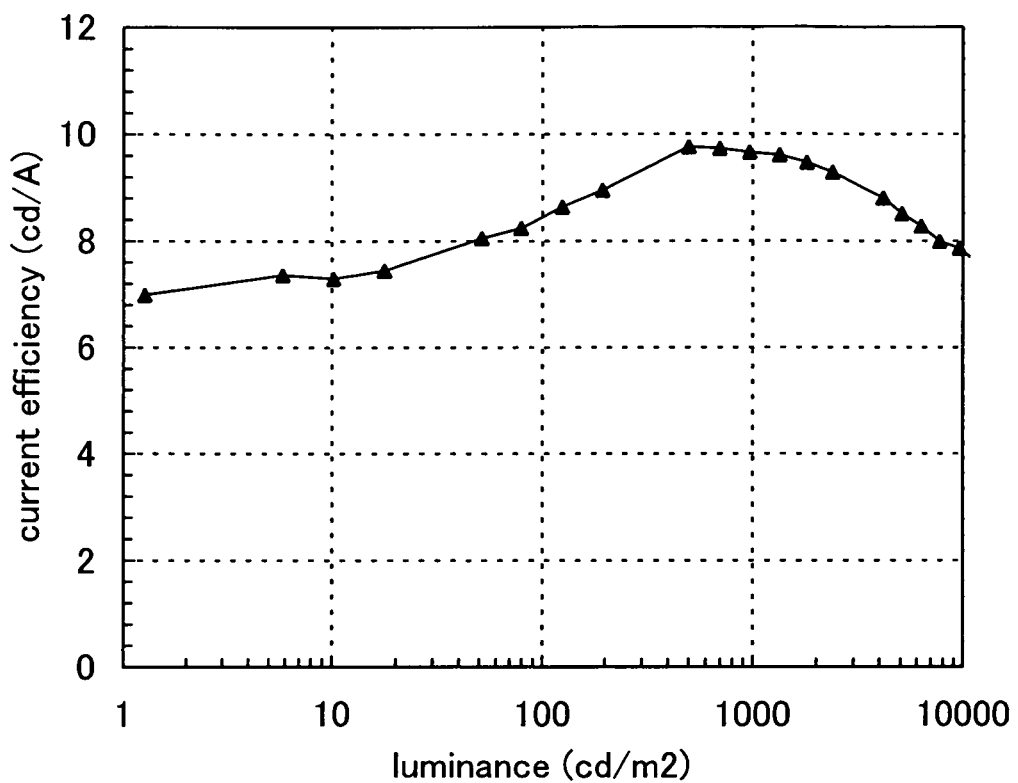
FIG. 18 shows a luminance-current efficiency property of a light-emitting element 1.
Figure 19:
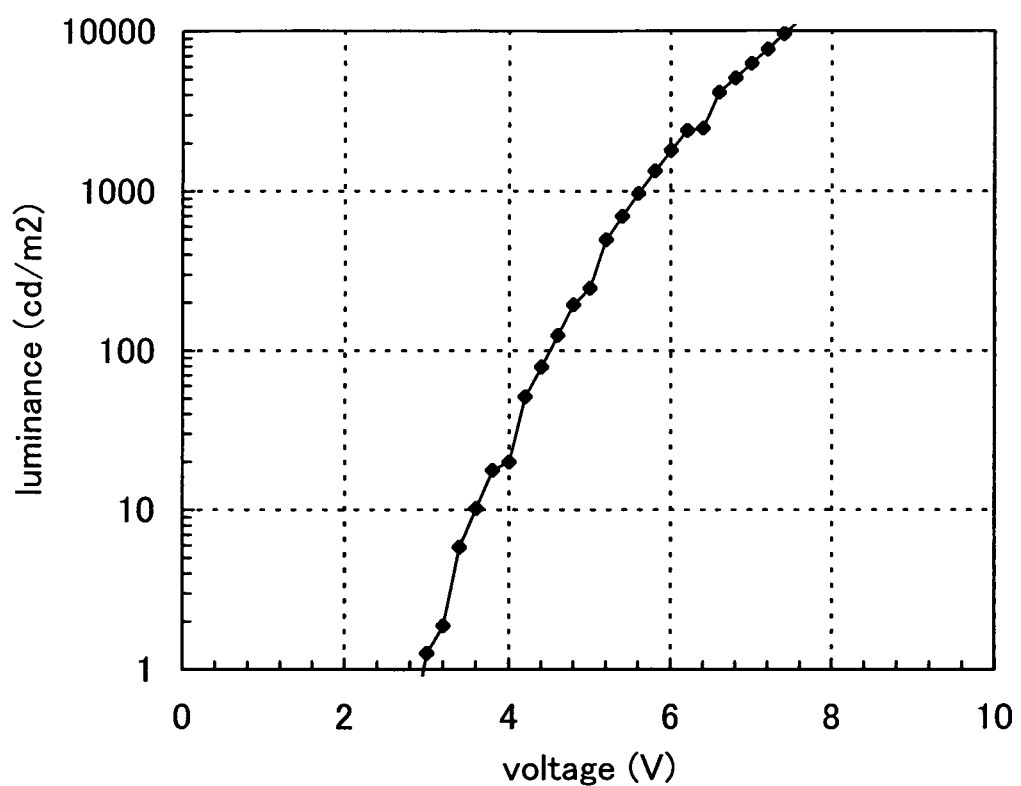
FIG. 19 shows a voltage-luminance characteristic of a light-emitting element 1.
Figure 20:
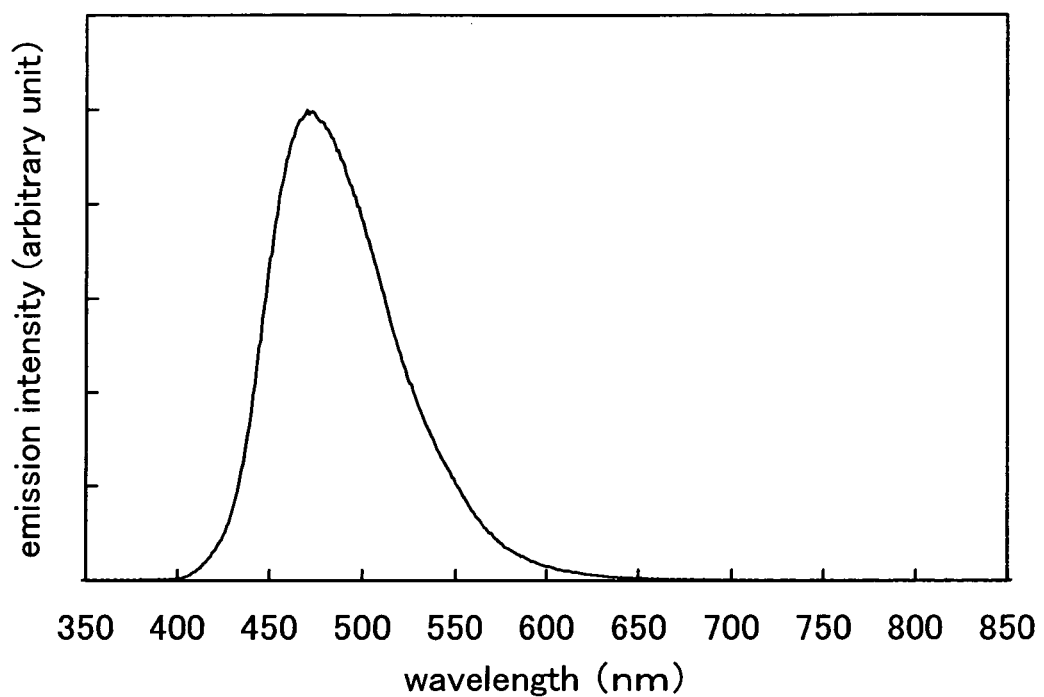
FIG. 20 shows an emission spectrum of a light-emitting element 2.
Figure 21:
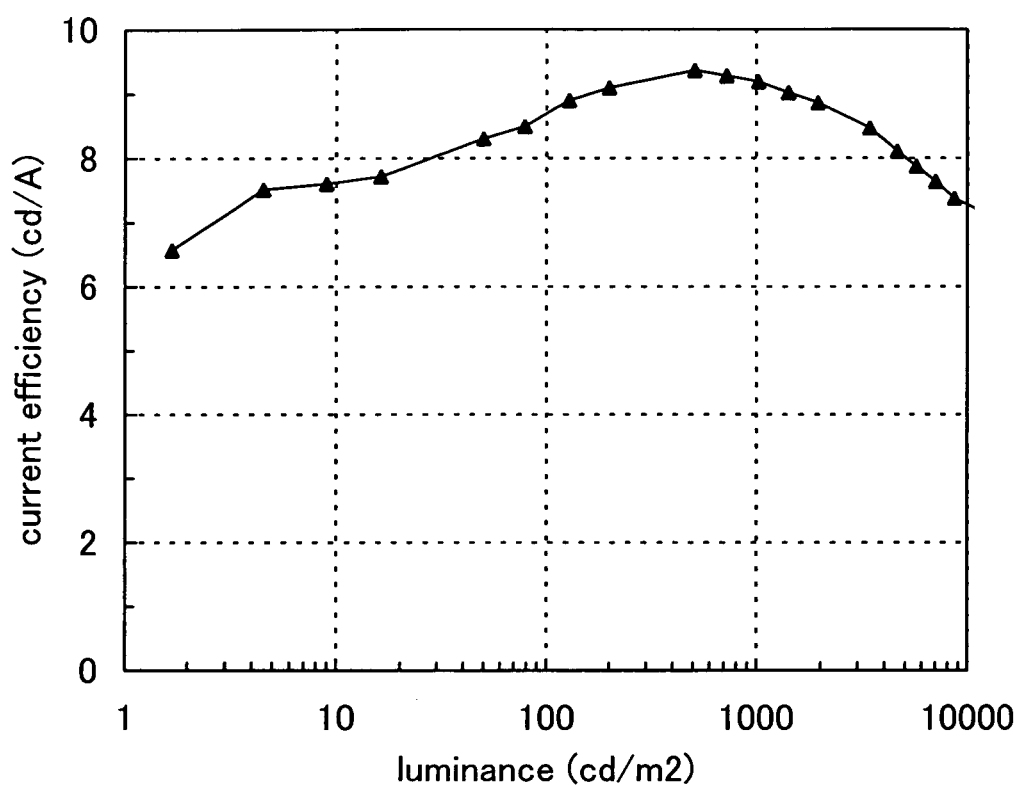
FIG. 21 shows a luminance-current efficiency property of a light-emitting element 2.
Figure 22:
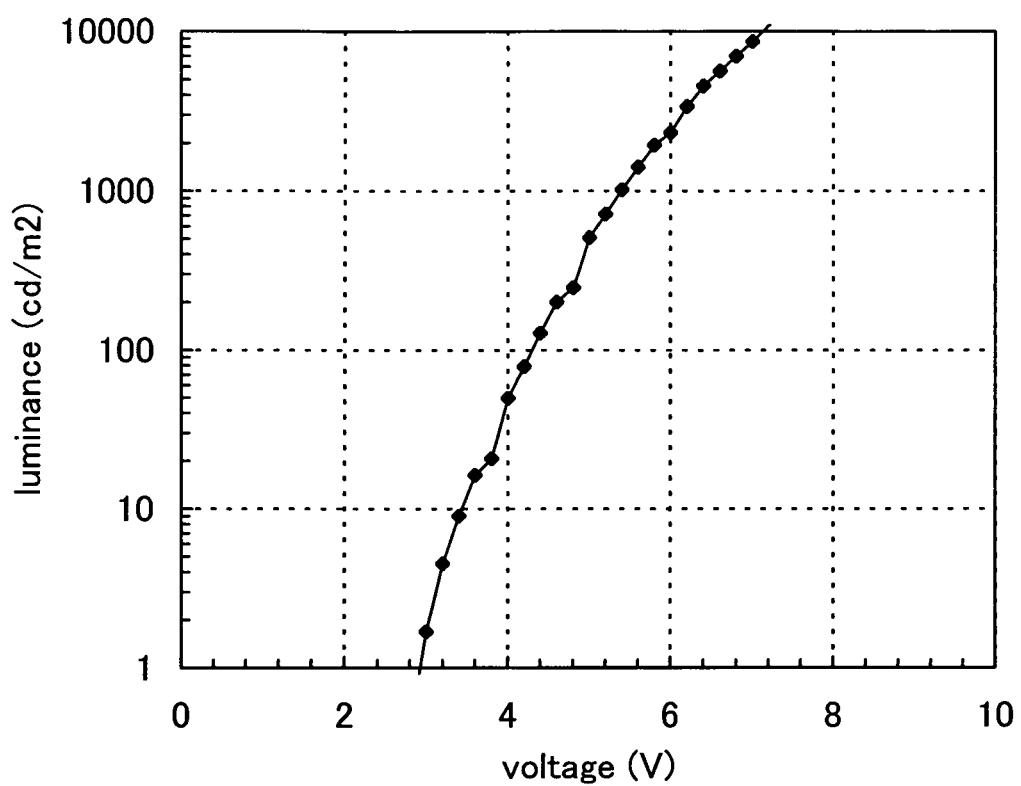
FIG. 22 shows a voltage-luminance characteristic of a light-emitting element 2.
Figure 23:
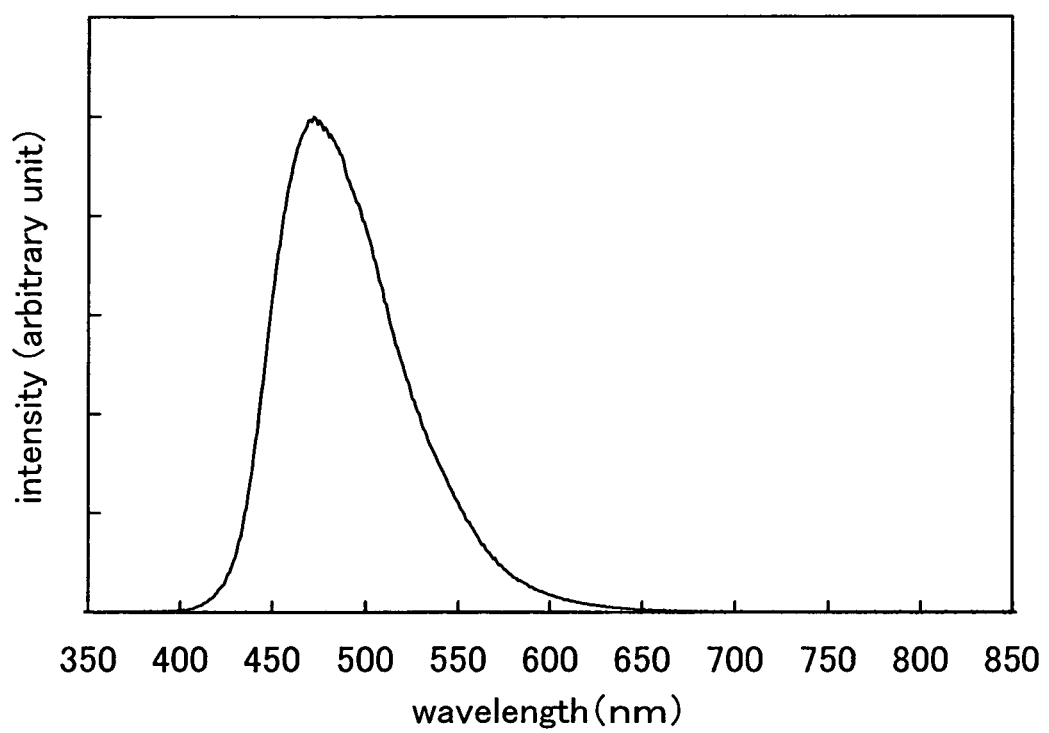
FIG. 23 shows an emission spectrum of a light-emitting element 3.
Figure 24:
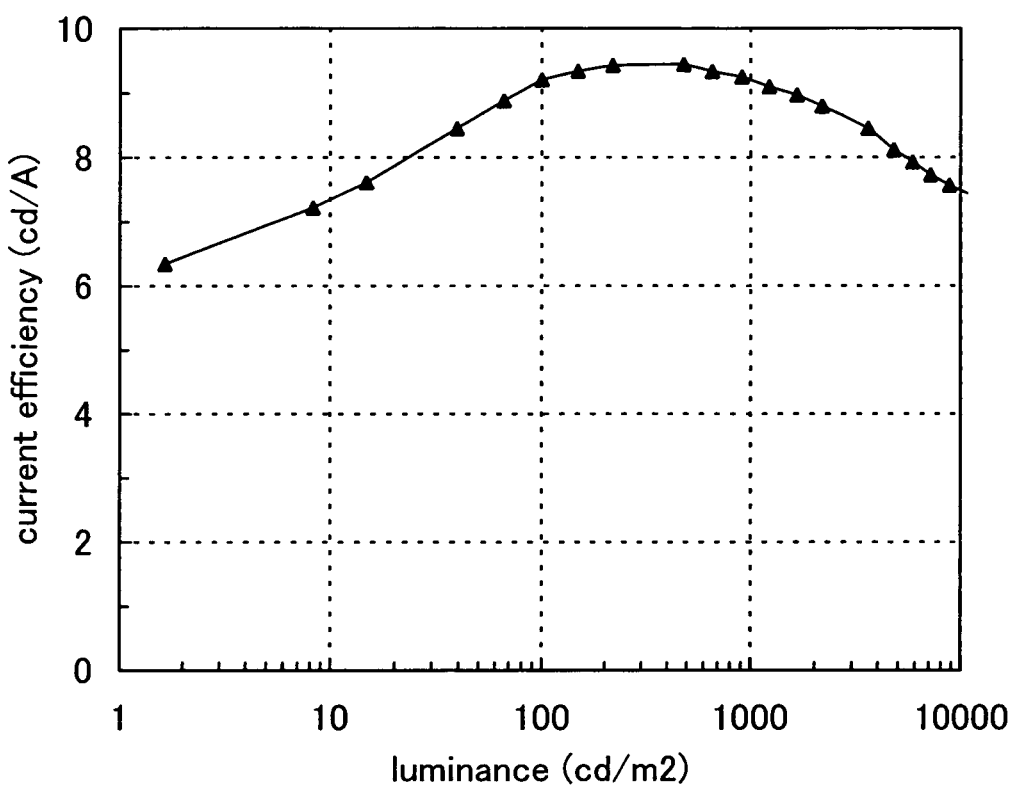
FIG. 24 shows a luminance-current efficiency property of a light-emitting element 3.
Figure 25:
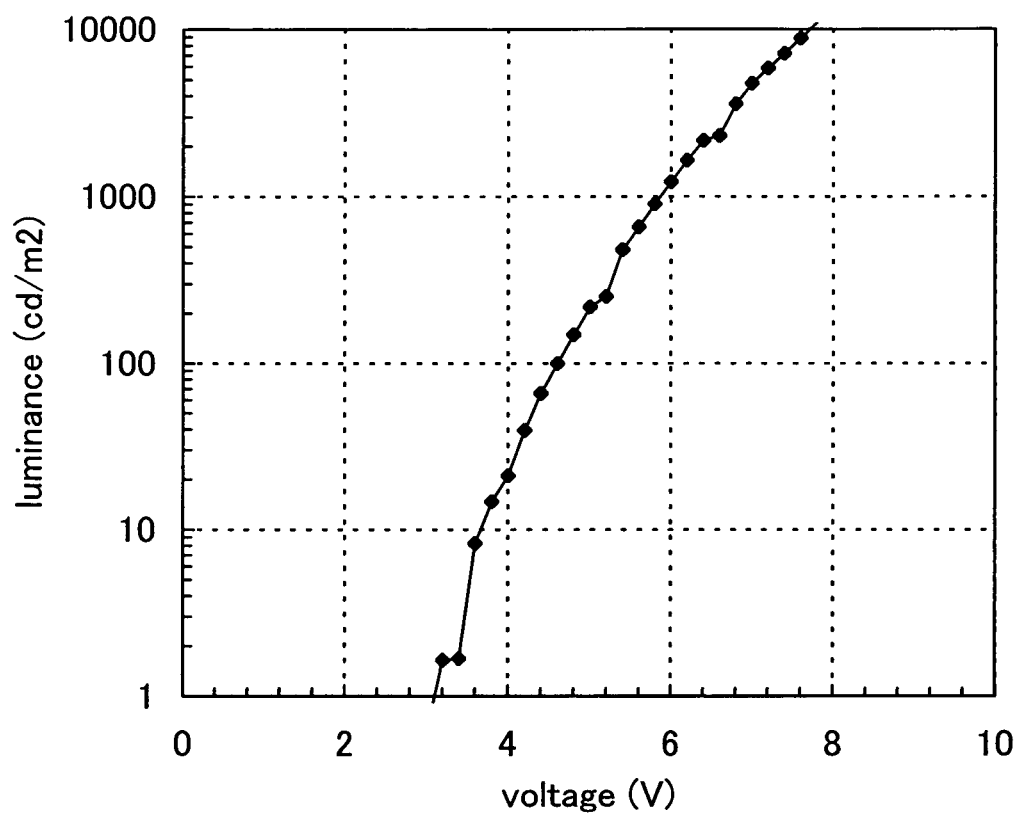
FIG. 25 shows a voltage-luminance characteristic of a light-emitting element 3.

An emission spectrum of the light-emitting element 1, a luminance-current efficiency characteristic thereof, and a voltage-luminance characteristic thereof are shown in FIG. 17, FIG. 18, and FIG. 19 respectively. An emission spectrum of the light-emitting element 2, a luminance-current efficiency characteristic thereof, and a voltage-luminance characteristic thereof are shown in FIG. 20, FIG. 21, and FIG. 22 respectively. An emission spectrum of the light-emitting element 3, a luminance-current efficiency characteristic thereof, and a voltage-luminance characteristic thereof are shown in FIG. 23, FIG. 24, and FIG. 25 respectively.

The light-emitting elements 1 to 3 of the present invention each have maximum emission wavelength of 470 to 472 nm. Further, the light-emitting elemetns 1 to 3 emit blue light with color purity as follows: chromaticity coordinate in a CIE color coordinate system of the light-emitting element 1 is (x, y)=(0.16, 0.24), chromaticity coordinate in the CIE color coordinate system of the light-emitting element 2 is (x, y)=

(0.16, 0.25), and chromaticity coordinate in the CIE color coordinate system of the light-emitting elemen 3 is (x, y)= (0.16, 0.26).

Figure 26:
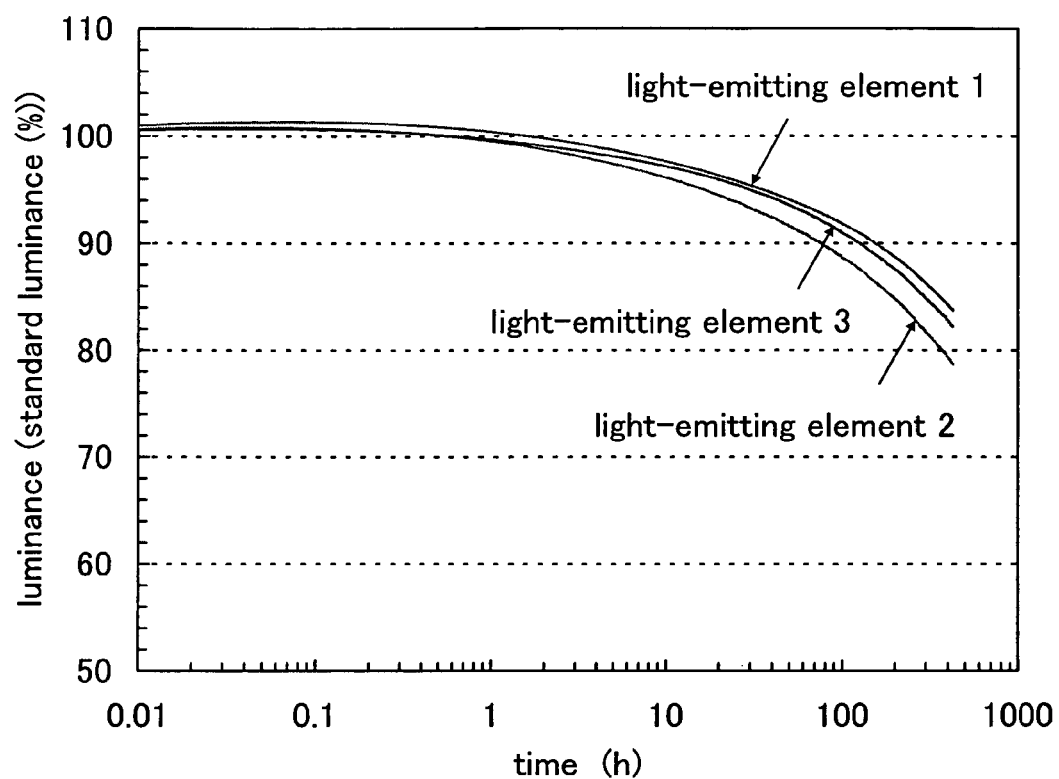
FIG. 26 shows the reliability of light-emitting elements 1 to 3.

Further, measurement results of change in lumiance with respect to driving time of the light-emitting elements 1 to 3 are shown in FIG. 26. A graph of FIG. 26 shows change in lumiance when the light-emitting elements 1 to 3 were driven under a condition of initial luminance of 500 cd/m² and constant current density. In FIG. 26, the horizontal axis represents a driving time (h), and the vertical axis represents luminance (standard luminance (%)) in the case where an initial luminance of 500 cd/m² is set at 100. As a result of this, it was found that it took 430 hours until the luminance of the light-emitting element 1 decreased to 84% of the initial luminance, it took 430 hours until the luminance of the light-emitting element 2 decreased to 79% of the initial luminance, and it took 430 hours until the luminance of the light-emitting element 3 decreased to 82% of the initial luminance. Accordingly, it is found that the light-emitting element of the present invention has a favorable life since the light-emitting elements 1 to 3 had little reduction in luminance with accumulation of the light-emitting time.

Figure 27:
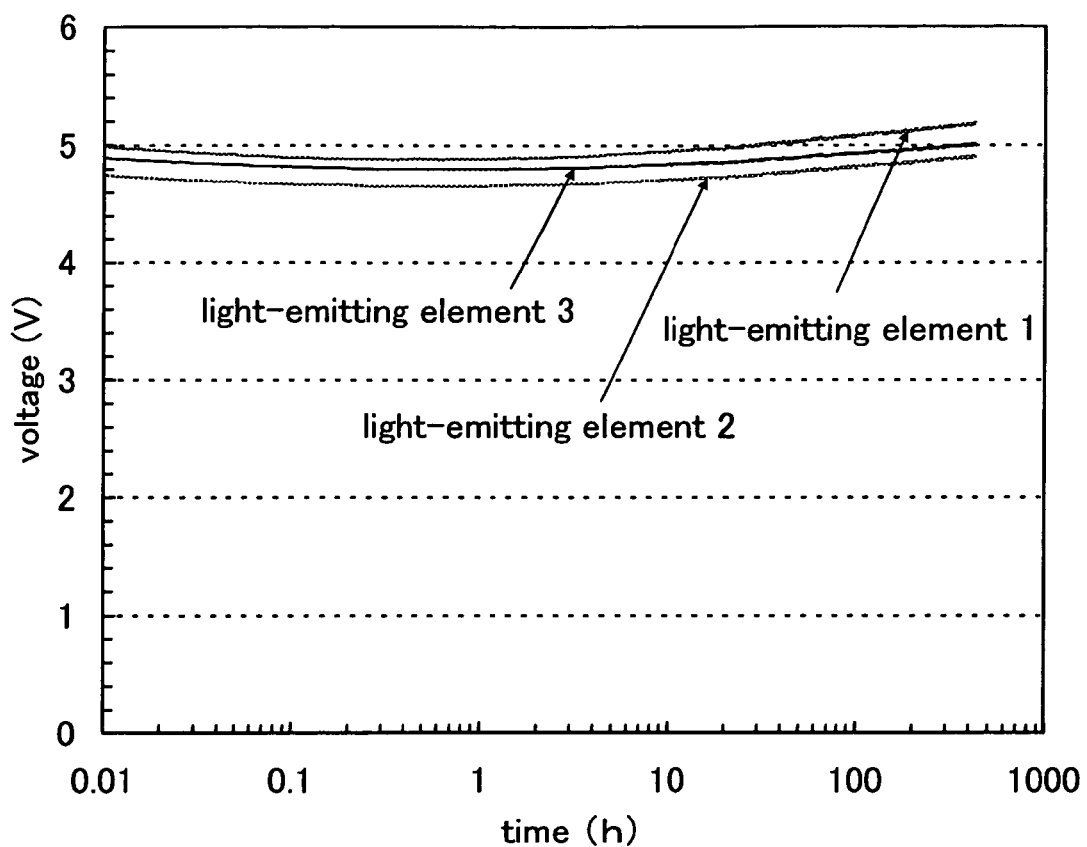
FIG. 27 shows the reliability of light-emitting elements 1 to 3.

Further, measurement results of change in driving voltage with respect to driving time of the light-emitting elements 1 to 3 are shown in FIG. 27. A graph of FIG. 27 shows change in driving voltage when the light-emitting elements 1 to 3 were driven under a condition of initial luminance of 500 cd/m² and constant current density. Accordingly, as for the light-emitting elements 1 to 3, it is found that the light-emitting element of the present invention is a good element having small increase of resistance with accumulation of the light-emitting time since increase of voltage with accumulation of the light-emitting time is small.

In addition, table 1 shows a result obtained by measuring power efficiencies [1 m/W] of the light-emitting elements 1 to 3 when the light-emitting elements were made to emit light at 1000 cd/m².

|  | light-emitting element 1 | light-emitting element 2 | light-emitting element 3 |
| --- | --- | --- | --- |
| power efficiencies (lm/W) | 4.9 | 5.3 | 5.4 |

It is found from table 1 that the light-emitting elements 1 to 3 have high power efficiency, and the light-emitting element of the present invention can be driven with low voltage.

This application is based on Japanese Patent Application serial No. 2005-254363 field in Japan Patent Office on Sep. 2, 2005, the entire contents of which are hereby incorporated by reference.

The invention claimed is:

1. An organic compound represented by formula (1):

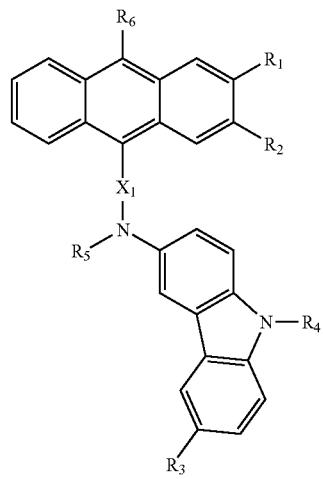

(1)

wherein $R_1$ and $R_2$ each represent either hydrogen or an alkyl group having 1 to 4 carbon atoms, wherein $R_3$ represents any one of hydrogen, an alkyl group having 1 to 4 carbon atoms or an aryl group having 6 to 25 carbon atoms, wherein $R_4$ represents either an alkyl group having 1 to 4 carbon atoms or an aryl group having 6 to 25 carbon atoms, wherein $R_5$ represents an aryl group having 6 to 25 carbon atoms, wherein $R_6$ represents any one of formulae (2) to (7),

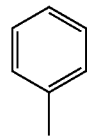

(2)

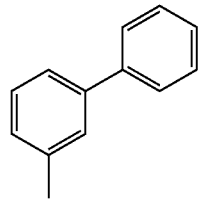

(3)

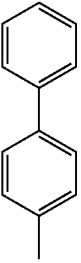

(4)

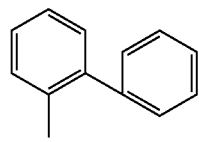

(5)

(6)
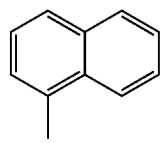

(7)
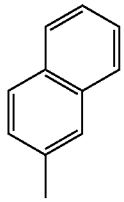

and wherein $X_1$ represents an arylene group having 6 to 25 carbon atoms.

2. The organic compound according to claim 1, wherein $R_4$ represents a phenyl group.

3. The organic compound according to claim 1, wherein $R_5$ represents a phenyl group or a naphthyl group.

4. The organic compound according to claim 1, wherein $X_1$ represents a phenylene group.

5. An organic compound represented by formula (1):

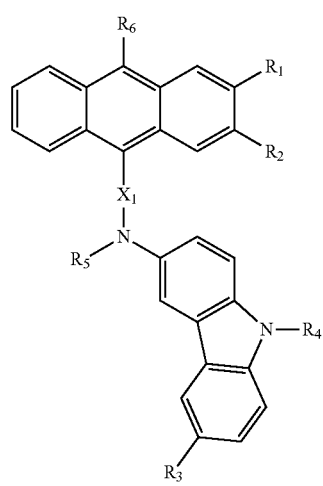

(1)

wherein $R_1$ and $R_2$ each represent hydrogen,
wherein $R_3$ represents any one of hydrogen, an alkyl group having 1 to 4 carbon atoms or an aryl group having 6 to 25 carbon atoms,
wherein $R_4$ represents either an alkyl group having 1 to 4 carbon atoms or an aryl group having 6 to 25 carbon atoms,
wherein $R_5$ represents an aryl group having 6 to 25 carbon atoms,
wherein $R_6$ represents any one of formulae (2) to (7), (2)
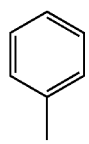

(3)
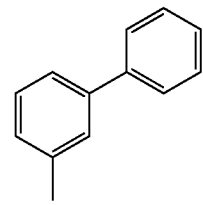

(4)
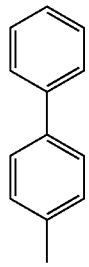

(5)
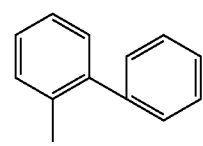

(6)
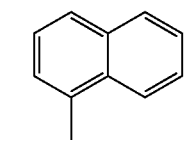

(7)
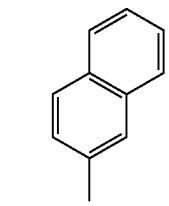

and wherein $X_1$ represents an arylene group having 6 to 25 carbon atoms.

6. The organic compound according to claim 5, wherein $R_4$ represents a phenyl group.

7. The organic compound according to claim 5, wherein $R_5$ represents a phenyl group or a naphthyl group.

8. The organic compound according to claim 5, wherein $X_1$ represents a phenylene group.

9. An organic compound represented by formula (1):

(1)

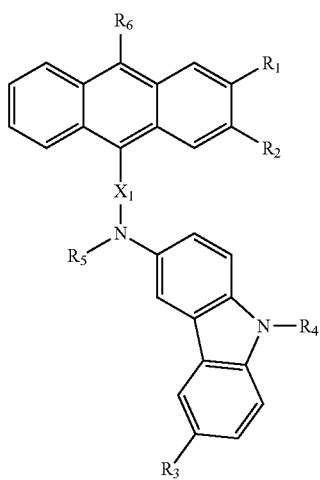

wherein either $R_1$ or $R_2$ represent an alkyl group having 1 to 4 carbon atoms, wherein $R_3$ represents any one of hydrogen, an alkyl group having 1 to 4 carbon atoms or an aryl group having 6 to 25 carbon atoms, wherein $R_4$ represents either an alkyl group having 1 to 4 carbon atoms or an aryl group having 6 to 25 carbon atoms, wherein $R_5$ represents an aryl group having 6 to 25 carbon atoms, wherein $R_6$, represents any one of formulae (2) to (7),

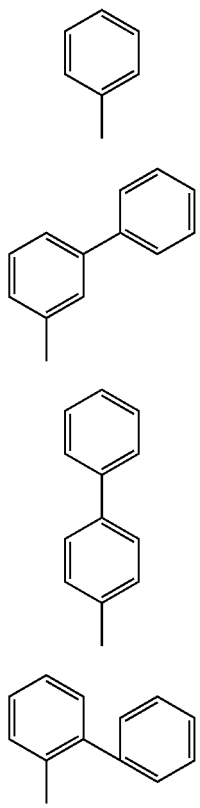

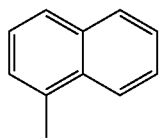

(6)

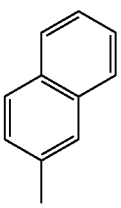

(7)

and wherein $X_1$ represents an arylene group having 6 to 25 carbon atoms.

10. The organic compound according to claim 9, wherein either $R_1$ or $R_2$ represent a tertiary butyl group.

11. The organic compound according to claim 9, wherein $R_4$ represents a phenyl group.

12. The organic compound according to claim 9, wherein $R_5$ represents a phenyl group or a naphthyl group.

13. The organic compound according to claim 9, wherein $X_1$ represents a phenylene group.

14. A light-emitting element comprising a layer containing an organic compound between a pair of electrodes, wherein the organic compound is represented by formula (1):

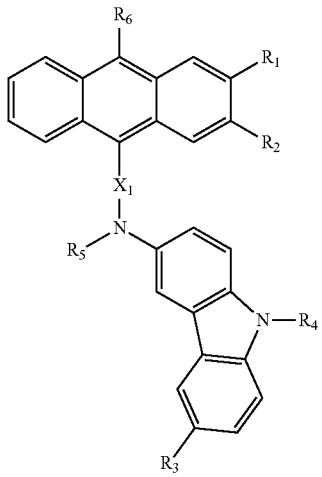

(1)

wherein $R_1$ and $R_2$ each represent either hydrogen or an alkyl group having 1 to 4 carbon atoms, wherein $R_3$ represents any one of hydrogen, an alkyl group having 1 to 4 carbon atoms or an aryl group having 6 to 25 carbon atoms, wherein $R_4$ represents either an alkyl group having 1 to 4 carbon atoms or an aryl group having 6 to 25 carbon atoms, wherein $R_5$ represents an aryl group having 6 to 25 carbon atoms, wherein $R_6$ represents any one of formulae (2) to (7), (2)

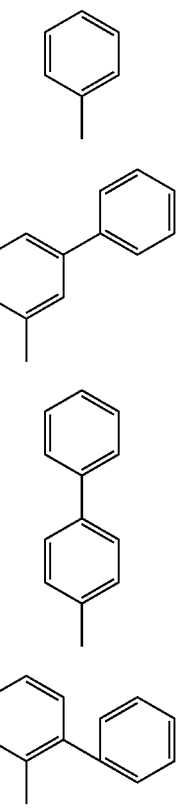

(3)

(4)

(5)

(6)

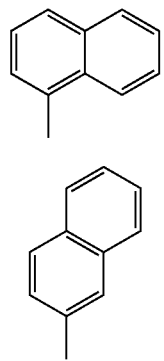

(7)

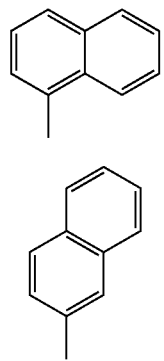

and wherein $X_1$ represents an arylene group having 6 to 25 carbon atoms.

15. The light-emitting element according to claim 14, wherein $R_4$ represents a phenyl group.

16. The light-emitting element according to claim 14, wherein $R_5$ represents a phenyl group or a naphthyl group.

17. The light-emitting element according to claim 14, wherein $X_1$ represents a phenylene group.

18. An electronic device comprising:
   a display portion comprising the light-emitting element according to claim 14.

\* \* \* \* \*